(12) United States Patent
Drancourt et al.

(10) Patent No.: US 7,601,822 B2
(45) Date of Patent: Oct. 13, 2009

(54) **MOLECULAR IDENTIFICATION OF BACTERIA OF GENUS *STREPTOCOCCUS* AND RELATED GENERA**

(75) Inventors: Michel Drancourt, Marseilles (FR); Didier Raoult, Marseilles (FR)

(73) Assignees: Universite de la Mediterranee (AIX-Marsille II), Marseille (FR); Centre National de la Recherche Scientifque (CNRS), Paris (FR)

( * ) Notice: Subject to any disclaimer, the term of this patent is extended or adjusted under 35 U.S.C. 154(b) by 32 days.

(21) Appl. No.: 10/529,319

(22) PCT Filed: Nov. 4, 2003

(86) PCT No.: PCT/FR03/03293

§ 371 (c)(1),
(2), (4) Date: Feb. 17, 2006

(87) PCT Pub. No.: WO2004/041841

PCT Pub. Date: May 21, 2004

(65) Prior Publication Data

US 2006/0199182 A1 Sep. 7, 2006

(30) Foreign Application Priority Data

Nov. 5, 2002 (FR) .................................. 02 13792

(51) Int. Cl.
*C07H 21/04* (2006.01)
*C12Q 1/68* (2006.01)
*C12P 19/34* (2006.01)

(52) U.S. Cl. ...................... 536/23.1; 536/24.3; 435/6; 435/91.2

(58) Field of Classification Search ........................ None
See application file for complete search history.

(56) References Cited

U.S. PATENT DOCUMENTS

| 6,420,135 B1 | 7/2002 | Kunsch et al. |
| 6,583,275 B1 * | 6/2003 | Doucette-Stamm et al. ............. 536/23.1 |
| 6,617,156 B1 * | 9/2003 | Doucette-Stamm et al. ............. 435/320.1 |
| 2002/0061569 A1 * | 5/2002 | Haselbeck et al. .......... 435/183 |

FOREIGN PATENT DOCUMENTS

WO   WO 02/077021 A2   10/2002

OTHER PUBLICATIONS

Mark Enright et al; "Molecular Evolution of Rifampicin Resistance in *Streptococcus pneumoniae*"; Microbial Drug Resistance; vol. 4; No. 1; 1998; pp. 65-70; XP009017720.
Database EMBL 'Online!; XP002255355; Apr. 16, 2001.
Database EMBL 'Online!; XP002255356; Mar. 28, 2002.
Database EMBL 'Online!; XP002255357; Sep. 7, 2001.
Database EMBL 'Online!; XP002255358; Sep. 2, 2002.
Database EMBL 'Online!; XP002255359; Oct. 27, 2002.
Database EMBL 'Online!; XP002255360; Sep. 28, 1999.
Database EMBL 'Online!; XP002255361; Oct. 3, 2000.

* cited by examiner

*Primary Examiner*—Teresa E Strzelecka
*Assistant Examiner*—David C Thomas
(74) *Attorney, Agent, or Firm*—Oliff & Berridge, Plc

(57) ABSTRACT

The invention concerns a method for detecting by molecular identification a bacterium of one of the species of genus *Streptococcus* and four related genera *Enterococcus, Gemella, Abiotrophia* and *Granulicatella* which consists of using as probe or primer:
  the rpoB gene or gene fragment of one said bacterium of sequences SEQ ID no 1 to 3, or
  an oligonucleotide or mixture of oligonucleotides derived from sequences SEQ ID no 8 to 35, or in particular the oligonucleotides of sequences SEQ ID no 6 and 7.

14 Claims, 1 Drawing Sheet

SEQUENCE LISTING

```
<160> NUMBER OF SEQ ID NOS: 52

<210> SEQ ID NO 1
<211> LENGTH: 4523
<212> TYPE: DNA
<213> ORGANISM: Streptococcus anginosus
<220> FEATURE:
<221> NAME/KEY: misc_feature
<222> LOCATION: (266)..(2087)
<223> OTHER INFORMATION: n represents a, t, c, g or i
<220> FEATURE:
<221> NAME/KEY: misc_feature
<222> LOCATION: (266)..(4430)
<223> OTHER INFORMATION: n represents a, t, c, g or i
<220> FEATURE:
<221> NAME/KEY: misc_feature
<222> LOCATION: (4430)..(4503)
<223> OTHER INFORMATION: n represents a, t, c, g or i

<400> SEQUENCE: 1
tcatactttt agagtcagat ttagctgctc tttttgtgcc tgttttggga ttttttgtcgt      60 ttgtcatcaa aattaaagat tctgaaaatt actcaaaaag gataaatgaa aattgctact     120
ctattccatt aatagagaat gtagaaagaa gaaggagtaa aaaacttggc aggacatgaa     180
gttcaatacg ggaaacaccg tactcgtcgt agtttttcaa gaatcaagga agttcttgat     240
ttaccaaatt tgattgaaat ccaganggat tcgttcaaag attttcttga ccatggtttg     300
aaagaagtat ttgaagatgt acttcctatc tcaaactttg cagatacaat ggagctagag     360
```

```
tttgttggtt atgaaattaa aggatctaaa tacactttag aagaagcacg tatccatgat    420
gccagctatt ctgcacctat ttttgtgact ttccgtttga ttaataaaga aactggtgaa    480
atcaaaaccc aagaagtgtt ctttggcgat ttcccaatca tgacagaaat gggaactttc    540
attatcaatg gtggtgagcg gattatcgta tctcagctcg ttcgttctcc aggtgtttac    600
ttcaacgata aagtaracaa aaatggtaaa gttggttatg gttcaactgy cattcctaac    660
cgtggagctt ggttagagct ggaaacagac tcaaaagata ttgcttatac tcggattgac    720
cgtactcgta agattccgtt tacgacactt gttcgtgcgc ttggttttc tggcgatgat     780
gaaatctttg acattttcgg cgacagcgat ctcgttcgca acacgattga aaaggatatt    840
cataaaaatc caatggattc acgtacggat gaagcgctta agaaatcta tgaacgtctt     900
cgtccaggtg agcctaaaac agctgatagt tcacgtagtc tattggtcgc tcgtttcttt    960
gatccacatc gttacgactt ggcggcagtt ggtcgttata aaatcaataa aaaattaaac   1020
attaaaacac gtttgttaaa tcaaacgatt gcagagcctt ggtagatcc agaaacaggt    1080
gaaatcttgg ttgaagctgg aacggttatg acgcgtagtg tcattgatag cattgcagaa   1140
tacttggacg gtgatttgaa taaaatcact tatattccaa atgatgcagc tgtgttaaca   1200
gagccagttg ttcttcaaaa attcaaagtg gtggcgccaa ctgatccaga tcgtgtggtg   1260
actattattg gtaatgccaa cccaggagat cgagttcata cgattacgcc agcagatatt   1320
ttggctgaga tgaattactt cttgaacctc gctgaaggac ttggtcgtgt ggacgatatt   1380
gaccacttgg gaaatcgtcg gattcgtgcc gttggtgaat tgcttgctaa ccaagtacgt   1440
cttggcttgt ctcgtatgga gcgaaacgtt cgggagcgca tgagtgtgca agataatgaa   1500
gtgttgacac cgcaacaaat cattaacatc cgcccagtca cagcagctat caaagaattc   1560
tttggttcat ctcaattgtc tcaatttatg gaccaacata atccactgtc tgarttgtct   1620
cacaaacgyc gtttgtccgc cttgggacct ggtggtttga ctcgtgaycg tgctggatat   1680
gaargtgcgt gacgtgcact acacncacta tggtcgtatg tgtccgattg aaacnnctga   1740
vggaccaaac atcggtttga tcaayaactt gtcttcttat ggtcanttga ataaatatgg   1800
ctttatccaa acgccgtatc gtaaagtgra tcgtgaaaca ggtctggtca chaatgaaat   1860
cgtttggttg acagcggang aagaagatga atttattgta gcgcaagcaa attctaaatt   1920
aacagaagat ggtcgttttg cagaagcgat tgtcatggga cgtcaccaag gaacaaccaa   1980
agaatttcct tcagatcarg trgatttcat ggatgtgtcg cctaagcagg tagttgccgt   2040
tgcgacagca tgtantccnk ttccytgaaa aygnacgact caarccntgn tstcatgggt   2100
gccaacatgc aacgtcaagc sgtaccgttg attgatccgc atgcaccata ygywggtana   2160
tggtatggaa taccaagcag antsaygamt ctggtgcggc tgattantgc mcaacacgac   2220
ggtaaagttg tmtattytga tgcagccaaa gttgaagttc gtcgtgaaga tggctcactt   2280
gtatgtntat catagntgac gaaattccgc cgttnaaact gstggtacgt tgmttacaac   2340
acaacgtagc ggstggtaaa agattggcga tacagntgta aaaggtgta stttatcgca    2400
gacggacctt ctatggaaaa aggtgaaatg gcrcttggac aaaayccaat cgttgcttat   2460
atgacatggg aaggttacaa ctttgaagat gccgttatca tgagtgagcg httagtgaaa   2520
gacgatgttt acacatctgt tcacttggag gaattcgaat cagaaacacg tgatacwaag   2580
cttaggmcct gaagaaatca ckcgcgaaat tccaaacgty ggtgaagatg ccnttygasa   2640
gaccttggac gaaayggggra ttataccgya ttggtgcyga rgttaaagag ggcgacattc   2700
ttgttggtaa agtcacacca aaaggtgaaa aagatctttc tgctgaagag cgtctcttgc   2760
```

| | | | | |
|---|---|---|---|---|
| acgcaatctt | cggtgacaag | tcacgtgaag | tacgtgatac | ytcycttcgt | gtaccwcayg | 2820 |
| gtgsygcatg | gkgyygtycg | tgatgtgaaa | atcttwactc | gtgcsaacgg | tgatgaattg | 2880 |
| caatcwggtg | tcaacatgtt | ggtacgtgtt | wcacntcgct | caaaaacgka | araycamgtg | 2940 |
| tyggrgataa | gatggcyggw | cgtcacggaa | acaaaggggt | tgtttcccgc | attgttccag | 3000 |
| ttgaggatat | gccgtatctt | ccagatgaaa | caccagttga | tattatgttg | aacccacttg | 3060 |
| gggtgccatc | tcgtatgaat | attggtcaag | ttatggagct | tcacctcggt | atggctgctc | 3120 |
| gcaaccttgg | cattcacatt | gcaacaccag | tatttgacgg | ggctagctca | gatgatcttt | 3180 |
| gggaaaccgt | tcgtgaagct | ggcatggata | gcgatgctaa | gacaatcctt | tatgatggcc | 3240 |
| gtactggtga | gccatttgat | aatcgtgtat | ccgttggtgt | catgtacatg | atcaaactcc | 3300 |
| accatatggt | tgatgataag | ctccatgccc | gttccgttgg | tccttattca | accgttacgc | 3360 |
| aacaacctct | tggtggtaaa | gcgcagtttg | gtggacaacg | ttttggagaa | atggaagttt | 3420 |
| gggctcttga | agcctacggt | gcttctaacg | tccttcaaga | aatcttgact | tacaagtcag | 3480 |
| atgacatcaa | tggtcgtttg | agagcttatg | aagccattac | caaaggtaag | ccaattccaa | 3540 |
| aaccaggtgt | tccagaatcc | ttccgtgtcc | ttgtaaaaga | attgcaatca | cttggtcttg | 3600 |
| acatgcgtgt | ccttgatgaa | gacgacaatg | aagtcgaact | tcgtgacttg | gacgaaggca | 3660 |
| tggatgatga | tgtgattcat | gtagacgatc | ttgaaaaagc | acgtgaaaaa | gcagcacaag | 3720 |
| aagcaaaagc | cgcttttgat | gctgaaggga | agaataaga | actgattcaa | tagataataa | 3780 |
| agaaaggtaa | gaaatagtgg | ttgatgtaaa | tcgttttcaa | agtatgcaaa | tcaccctagc | 3840 |
| ttctcctagt | aaagtccgct | cttggtctta | tggagaagtg | aagaaacctg | aaacaattaa | 3900 |
| ctaccgcaca | ctaaaaccag | aacgcgaagg | gcttttgat | gaagtcatct | ttggtcctac | 3960 |
| gaaagactgg | gaatgtgcgt | gtggaaaata | taaacggatt | cgttataaag | gaatcatttg | 4020 |
| tgaccgttgt | ggtgttgaag | taactcgtac | taaagttcgt | cgtgaacgta | tgggacatat | 4080 |
| tgagttgaaa | gccccagtct | cctcatattt | ggtattttaa | aggaattcca | antcgcatgg | 4140 |
| gcntgacctt | ggacatgagc | cctcgtgctc | ttgaagaagt | catntantt | gcagcttatg | 4200 |
| tggtgantga | ccctaaagat | acnccacttg | agcacaaatc | cattatgaca | gagcgggatg | 4260 |
| gttngtgaac | gctgacntga | atatggccaa | ggctcttttg | ttgcaaaaat | gggtgytgaa | 4320 |
| gcaatccaag | atctnntgaa | acangtagac | ntggaaaaag | aaattgcaga | gctcaaagat | 4380 |
| gaattaaaaa | cggcaagtgg | gcaaaagcgc | gtaaamgcta | anttcgtcgn | tnngactctt | 4440 |
| ttcgatnctt | tccaaaaatc | atggtacaca | aaaccagaac | tggatggtct | taaaccatcn | 4500 |
| ntntcaccgc | tcattccaga | cac | | | | 4523 |

```
<210> SEQ ID NO 2
<211> LENGTH: 4118
<212> TYPE: DNA
<213> ORGANISM: Streptococcus equinus

<400> SEQUENCE: 2
```

| | | | | |
|---|---|---|---|---|
| cacgcgtggt | cgacggcccg | ggctggtgaa | ttgtcataag | ttgtgtagta | gtaaattccc | 60 |
| ttatcagtgt | tgatgcatga | gctataaata | gtgtactcat | atttgccact | ttcatcgaca | 120 |
| tagcaaagtc | cttttgttg | ttcaacggat | tttaaaatgt | ggaagaattg | attaacactg | 180 |
| ctttcttctg | tttcttccagc | cacagaattt | aattttgtaa | aagtaacttt | tacataacgt | 240 |
| gacattgatg | ataaatcacc | aggcaagcca | agtccaccca | tgccacggct | ataagtttca | 300 |

```
agttctaact ctttagcaaa acgattttct gaaacctttg gagatagatg acgatagtta    360
ttcaaattga ataattgttt atcaaaagtt ggattattag tcaaaacacc tgttgagtta    420
ttcgtaaact tatagggcac gcgtggtcga cggcccgggc tggtaaagac ttcttggata    480
acggattaam agaagttttt gaagatgtac ttccgattac aaactttacg gatactatgg    540
agcttgaatt tgttggttac gaattgaaag agcctaagta tacgcttgaa gaagctcgta    600
tccacgatgc atcttattca gcacctattt ttgtaacctt ccgtttgatt aataaagaaa    660
caggagaaat caaaactcaa gaagttttct tcggtgattt cccaattatg actgaaatgg    720
gtacattcat catcaacggt ggtgaacgta ttatcgtttc tcagttggtt cgttctcctg    780
gtgtttattt caacgataaa gttgataaaa acggtaaagt tggttacggt tcaactgtaa    840
tccctaaccg tggagcatgg cttgaattag aaacagattc aaaagatatt gcttacacac    900
gtatcgaccg tacacgtaaa attccattta caactcttgt acgtgcgctt ggtttctcag    960
gtgatgatga atcatggat atctttggtg atagcgaact tgttcgtaac acaatcgaaa   1020
aagatattca caaaaaccca gcagactcac gtactgacga agctcttaaa gaaatttacg   1080
aacgccttcg tccaggtgaa ccaaaaacag ctgatagctc acgtagcttg cttgtagctc   1140
gtttctttga cccacgtcgt tatgacttgg cagctgttgg tcgttacaaa atcaacaaaa   1200
aacttaacat caagactcgt cttttgaacc aaacaatcgc tgaaaacttg gttgatgctg   1260
aaactggtga atccttgtt gaagctggta cagtaatgac acgtgacgtg attgattcaa   1320
tcgctgatca attggatggt gaccttaaca aatttgttta cacaccaaat gattacgctg   1380
ttgtcactga acctgttgtt cttcaaaaat caaagttgt tgcaccaaac gatccagacc   1440
gcgttgttac aatcgttggt aacgcaaatc ctgatgacaa agcgcgtgcg cttacaccag   1500
ctgatatctt ggcagaaatg tcttacttcc ttaaccttgc tgaaggtcta ggtaaagttg   1560
atgatatcga ccaccttggg aatcgtcgta ttcgtgccgt tggtgaattg cttgctaacc   1620
aattccgtat tggtcttgct cgtatggaac gtaacgttcg ggaacgtatg tcagttcaag   1680
acaacgaagt gttgacacca caacaaatca tcaacattcg tcctgttact gcagccgtta   1740
aagaattctt cggttcatct caattgtcac agttcatgga ccaacacaac ccactttctg   1800
agttgtctca caaacgtcgt ttgtcagcct taggacctgg tggtttgact cgtgaccgtg   1860
ctggttatga agttcgtgac gtgcactaca ctcactatgg tcgtatgtgt ccgattgaaa   1920
ctcctgaagg acctaacatc ggtttgatca ataacttgtc aacatacgga caccttaata   1980
aatatggttt catccaaaca ccatatcgta agttgaccg cgctacaggt gtgattacaa   2040
acgaaatcgt ttggttgact gccgatgaag aagatgaata cacagtagca caggctaact   2100
caaaacttaa cgaagatgga acatttgctg aagacatcgt tatgggacgt caccaaggta   2160
ataaccaaga gttcccagca agcgttgttg acttcgtaga cgtttcacct aaacaagtag   2220
ttgccgttgc gacagcatgt attcctttcc ttgaaaacga tgactctaac cgtgcccttc   2280
tgggtgccaa catgcaacgt caagcggtgc cattgattga tccacacgca ccatatgttg   2340
gtactggtat ggaatatcaa gcagcccacg actcaggtgc tgcagttatc gctaaacacg   2400
atggacgcgt tatcttctct gatgctgaaa agttgaagt tcgtcgcgaa gatggttcac   2460
ttgatgttta ccacattact aaattccgtc gttctaactc aggtacagct tataaccaac   2520
atacacttgt taaagttggc gatatcgttg aaaaggtga cttcatcgct gatggtcctt   2580
caatggaaaa aggtgaaatg gcccttggtc aaaaaccaat cgtcgcttac atgacktggg   2640
aaggttacaa cttcgaggat gcggttatca tgtctgaacg ccttgtgaaa gatgatgtct   2700
```

```
atacatctgt tcacttggaa gaatacgaat cagaaacacg tgatactaag ttaggccctg    2760
aagaaatcac tcgcgaaatt ccaaacgttg gtgaagatgc ccttcgcaac ttggacgaaa    2820
tggggattat ccgtattggt gccgaagtta agagggcga cattcttgtt ggtaaagtca    2880
caccaaaagg tgaaaaagat cttctgctg aagagcgtct cttgcacgca atcttcggtg    2940
acaagtcacg tgaagtacgt gatacctctc ttcgtgtacc tcacggtgcc gatggtgtcg    3000
ttcgtgatgt gaaaatcttt actcgtgcca acggtgatga attgcaatca ggtgttaaca    3060
tgttggttcg tgtttcacat cgctcaaaaa cgtaagatca aggtcggaga taagatggcc    3120
ggtcgtccac ggtaacaagg gtgtcgtttc acgtaywgta cctgttgagg atatgccata    3180
tcttccagat ggaacaccag ytgacawcat gttgaaccca ctsggggtgc catcwcgtat    3240
gaacatcgga caagttatgg agcttcacct tggtatggct gctcgtaacc ttggtattca    3300
cattgcaaca ccagtctttg atggggcaac ttctgaagac cttttgggata cagttaacga    3360 agctggtatg gctagcgacg ctaagacagt tctttacgat ggacgtactg gtgaaccatt    3420
tgataaccgt gtgtcagttg gtgtcatgta catgattaaa cttcaccaca tggttgatga    3480
taaacttcac gcacgttcag ttggtcctta ctcacttgtt acgcaacaac ctcttggtgg    3540
taaagcacaa tttggtggac aacgtttcgg tgaaatggaa gtttgggctt tggaagctta    3600
cggtgcatca aatgttcttc aagaaatctt gacttacaaa tcagatgatg tcaacggtcg    3660
tcttaaagct tatgaagcca tcactaaagg taaaccaatt ccaaaaccag tgttccaga    3720 atcattccga gttcttgtaa agaattgca atcacttggt cttgacatgc gcgtgcttga    3780
tgaagatgac aatgaagtag aacttcgtga tcttgatgaa ggtgaagatg acgatgttat    3840
gcacgttgat gatcttgaaa agctcgtca aaaacaagaa gcagaagaag cggaaaaagc    3900
agaagtttct gcagaagaaa acaaataata ggaaagaaca ttcagacatg agagaggcaa    3960
gacctgcttc tcttggtcag attgtttgat tgagtcctat aacgataaat gatgtcttac    4020
gaatcatgaa tttgtaagtc atgacagtta gaaagtagcg cagctatttc aaagtcataa    4080
gaaggtatca tggtgacgta atcgttacag ccggcgtc                           4118
```

<210> SEQ ID NO 3
<211> LENGTH: 3425
<212> TYPE: DNA
<213> ORGANISM: Abiotrophia defectiva

<400> SEQUENCE: 3

```
atatagggca cgcgtggtcg acggcccggg ctggtcctaa acaacatgta acgtcactcc      60
gatgagttgg ttctgttgtc ttttttttgc gcttcaaaga ccgaaaaatg tcatttgtca     120
acaattatta ataattgtaa ccttaatgta aagtggtgtt cttagattat attatagggg     180
tgaatcgctt gagtcatatc gtgaaatacg gtaaaaaagc tgagcgtcga agctatgcgc     240
gtatcgacga agtcttagag ttgccgaact tgattgaaat ccaaacggat tcctacaaat     300
ggttcttgga tgaagggcta aaagtgatgt tcgaggacat ttcgccgatt gtcgaccatt     360
cggagaactt ggaacttcat tttgtagact atgagttcaa ggaagctaag tatagcttag     420
aagaagctcg tagccatgac gctaactact caaaaccaat ctatgtaacc ttgcgcctgt    480
tcaacaaaga gacaggtgaa gtcaaagaac aagaagtctt cttcggggac ttcccaatca    540
tgaccgaaat ggggaccttc attatcaacg gggcggaacg ggttatcgtt tcccagttgg    600
tacgttctcc aggtgtctac ttccacgacc gtatggacaa gaaaggccgc cacagctata    660
```

```
cttctacggt tattcctaac cgtggggctt ggttggaatt tgaatcagat gctaagggga     720
ttgcctacgt ccgcattgac cggacccgga agattccatt gactgtcttg atgcgtgcct     780
taggttttgg ttcagatgac gagatttatg atatcttcgg ccaatctgag ctcttagact     840
taactatcga gaaggatgtt cacaaaaaca ttcaagactc tcgtacggaa gaagccttga     900
aggacattta cgagcgtctc cgtccaggtg aacctaagac cgcagaaagc tcacgtaacc     960
tcttggttgc gcgcttcttc gacccacgtc gctatgactt agcacctgta ggtcgttata    1020
agatcaataa aaagctccac ctcaagaacc gtttggttgg cttgactttg gctgaaacct    1080
tggttaaccc agaaacaggc gaagtgctct ttgaagaagg aacggtcttg gatcaagaac    1140
gtgttcaagc cctgattcca tacttagagg ctggcttgaa taaggtaacc ctctatcctt    1200
ctgaagatag tgtggtagct caaccaattg atttacaaat catcaaagtt tattcaccta    1260
agaacgccga gcaagtgatt aacatcatcg gtaacgggaa cattgagaag attaagtgct    1320
tgacgccagc tgacattatt gcgtcaatga actactatct ctatttagac caaggaattg    1380
gtgtgacaga tgatatcgac cacttggcta accgtcgtat tcgttcagtc ggtgaattat    1440
tgcaaaacca attccgtatc gggctatccc ggatggaacg ggtagtgcgt gaacgtatgt    1500
cgctccaaga tgttgcgacc atcacaccgc aacaattgat taacattcgt ccagtagtgg    1560
cggctattaa ggaattcttc ggttcatccc agttgtcaca attcatggac caagttaacc    1620
cactcgggga attgacccac aaacgtcgtc tgtcagcctt agggcctggt ggtttgacgc    1680
gggaccgtgc cggctatgaa gtgcgggacg ttcactactc tcactacggc cgtatgtgtc    1740
caatcgagac gccagaaggt cctaacatcg ggttgattaa cagcttgtct tcttatgcca    1800
agattaacaa gtatggtttt attgagacgc cttaccgtaa agtggacaaa tcggttacgc    1860
cacaccgtgt cacgaccgaa attgactacc tagcagcgga cgaggaagac ttgtacgtag    1920
tagcccaagc caactctaaa ctcaacgaag acgggacctt cgccaatgac ctagttatgg    1980
cgcgtttccg ttcacaaaac attgaggtta acgttgacca agtagactac atggacgtat    2040
cgccaaaaca ggttgtcgct gtcgcgactg ctagcattcc gttcttggaa aacgacgact    2100
ccaaccgggg cttgatgggt gccaacatgc aacgtcaagc tgtgccactt attaatccac    2160
aatccccact gattgggact gggatggaat ataaggcagc acacgactct ggggctgcgc    2220
tcttatgtaa gcgcgccggt gaagtggttt atgtcgatgc taacaaggtg cgcgtgcgca    2280
ctccagaagg tgaagttgac gaataccgtt taaccaagtt tgcacgttct aacgctggga    2340
cctgttacaa ccaacgtcca atcgtagaat taggcgacca agttgatgcc ttggaaatct    2400
tagcagatgg tccatctatg caaaatgggg agatggccct cggtcaaaac ccactggtag    2460
ccttcatgac ttgggaaggg tataactatg aggacgcggt tatcatgtct gaacgtctgg    2520
tcaaagacga tgtttatacc tctatccaca ttgaagaata tgaatcagag tcccgtgaya    2580
cyaagttagg ccctgaagaa attacacgcg aaattccaaa cgtgtccgaa gatgccctca    2640
agtacttaga caaagacggg attatctgta tcggggcgga agtaaaagac ggcgatatct    2700
tagttggtaa ggtaacacca aaaggtgtga ccgagttgtc tgcggaagaa cgcttgctcc    2760
atgctatctt cggtgagaag gcgcgtgaag tacgtgatac ttccttgcgt gtgccacacg    2820 gcggggggcgg gattgtccac gacgttaaaa tctttacccg cgaagctggc gacgaattgg    2880
caccaggtgt caacaagcta gtccgcgtct acatcgtaca aaaacgtaaa atcaatgaag    2940
gggataagat ggccggtcgt cacgtaacaa aaggggttgt ctcccttatc atgccggaag    3000
aagatatgcc attcttacca gatggtaccc cagttgatat catgttgaac ccattagggg    3060
```

```
ttccatcccg tatgaacatc gggcaagtcc tagagttaca cttggggatg gctgctcgcg    3120
aaatgggcat caagattgca acacctgtct tgacggtgc tagtgaagaa gatgtctggg    3180
aaacagttaa ggaagccggc ttagaagctg acgctaagac tatcttatat gatggtcgaa    3240
ccggtgaacc atttgaccgt aaagtctctg ttggggttat gtacatgatt aagttggccc    3300
acatggtcga tgacaagttg cacgcccgtt caacaggtcc atactctctg gttacccaac    3360
aaccattggg tggtaaagct caatttggtg ggcaacgttt cggggagatg gaggtttggg    3420
cccta                                                                3425
```

```
<210> SEQ ID NO 4
<211> LENGTH: 3198
<212> TYPE: DNA
<213> ORGANISM: Streptococcus mutans
<220> FEATURE:
<221> NAME/KEY: misc_feature
<222> LOCATION: (619)..(3193)
<223> OTHER INFORMATION: n represents a, t, c, g or i

<400> SEQUENCE: 4
```

```
ggacccttttt atgacttctt ggatacaggt ctgaaggaag ttttgaaga tgtgcttcca     60 atttccaatt tcacagacac tatggaatta gagtttgtgg gttatgagtt gaaagagcct    120
aagtatacat tggaagaagc acgtgctcat gatgcacatt attctgcccc catctttgtt    180
actttccgtc tcatcaataa agaaactggt gaaattaaga cacaagaagt attttttggt    240
gattttccct tgatgactga aatgggtact tttattatta atggtgctga acgtattatc    300
gtttctcagt tggtacgttc accaggtgtt tattttaatg ataaagtgga taaaaatggg    360
aaaattggct atggttcaac tgttatccct aaccgcggtg cttggcttga gcttgaaacg    420
gactctaagg atattgctta tactcgtatt gatcgtactc gtaaaattcc ttttacgacg    480
ctggttcgtg cactcggttt ttccggggat gatgagatta ttgatatttt tggtgatagc    540
gaattggttc gtaataccat tgaaaaagat atccataaaa atcctaatga ctctcgtaca    600
gatgaagctc tcaaggaant tatgaacgtc ttcgtccggg tgaacctaaa acggcagatt    660
cntcacgcag tcttctgatt gcacgtttct tgatgcgcg ccgttatgat tagcagctgt    720
tggccgctat agataataag aagttaaacg tcaaaacggg tctttgaatc aagtcattgg    780
ctgaaaanna gtagatctga aacaggcgaa attcttgttg aaagctggga ctgaaatgac    840
acgcagtgta attgattcga ttgcagatta tcttgatgga gatctcaata aaattgttta    900
tacgccaaat gaatacgctg ttttgacaga acctgttgtt cttcaaaaat tcaaagttat    960
ggctccaaat gatccagacc gcacggttac tgttattggt aatgccagtc caagatgaca   1020
aagtacgtca cttgacacca gccgatacgt attagctgaa atgtcttatt tccttaactt   1080
ggctgagggt ntaggtaaag ttgatgatat tgaccattta gcaaccgac gtattcgtgc    1140 tgttggtgaa ttgcttgcta atcaatttcg tattggtttg gcacgtatgg aacgcaatgt   1200
tcgtgaacgc atgtccgttc aagataatga agtcttaacg ccacaacaga ttattaacat   1260
tcgccctgta acagcggcaa ttaaagagtt ttttggttct tctcaattgt cacagttcat   1320
ggaccaacac aatccactgt ctgaattgtc tcataaacgc cgtttgtcag ctttaggtcc   1380
tggtggttta acacgcgacc gtgctggtta tgaagtccgt gatgtgcact atacgcatta   1440
tggtcgtatg tgtccaattg aaacgcctga aggaccaaat attggattga ttaataactt   1500
gtcttcctat ggtcatctta ataaatatgg atttatccaa acaccatacc gtaaagttga   1560
```

```
ccgtgagaca ggtaaagtaa ccaatgaaat cgaatggctt actgctgatg aagaagatga   1620
attcactgta gctcaggcta actcaaaact caatgaagat ggaagctttg ctgaagaaat   1680
cgtcatggga cgtcatcaag ggaataacca agagtttcca gcaagttctg ttaatatat    1740 ggatgtttct cctaagcagg tagttgcggt agcgacagca tgtattcctt tccttgaaaa   1800
tgatgactcc aaccgtgccc ttatgggagc taacatgcag cgccaagctg tgccattgat   1860
tgatcctaaa gcacctttg ttggaactgg tatggaatat caagcagccc atgattctgg    1920
agccgctatt atcgctcaac ataatgggaa agtggtttat tccgatgcag ataagattga   1980
agttcgccgt gaagatggct cactagatgt ttatcatgtt accaaattcc gtcgttctaa   2040
ctctggaact gcctacaatc aacgtactct tgtagggta ggcgatagtg ttgagaaggg    2100
ggactttatt gcagatggtc cttctatgga aaagggtgag atggctcttg acaaaatcc    2160 agtggttgct tacatgactt gggagggtta caactttgaa gatgctgtta tcatgagcga   2220
gcgtcttgtc aaggatgatg tttatacttc tgtccattta gaagaatttg aatctgaaac   2280
tcgtgataca aagcttggac ctgaagaaat tacgcgtgaa atcccaaatg ttggtgaaga   2340
tgccctgaaa gaccttgatg aaatgggaat tattcgcatt ggtgctgagg ttaaagaagg   2400
tgatattcta gttggtaaag tgactcctaa aggagaaaaa gatctttctg cagaagaacg   2460
cctcttgcat gccattttg gtgacaaatc acgtgaagtt cgtgatactt ctcttcgtgt    2520
acctcatggt ggcgacggtg ttgtttgtga tgtgaaaatc tttacacgtg ctaatggaga   2580
tgaacttcaa tcaggtgtta acatgctggt tcgtgtttat atcgctcaaa acgtaaaat    2640 caaggtcgga gataagatgg ccggacgtca tggtaacaag ggtgtcgttt cccgtattgt   2700
accagtggaa gatatgccat atcttccaga tggaacacct gttgatatca tgcttaatcc   2760
acttggggtg ccatcacgga tgaacattgg gcaagttatg gaactccatc ttggtatggc   2820
tgctcgtaat ttgggcattc atattgcaac gcctgtcttt gacggagcaa cttctgatga   2880
tctttgggaa acagtaaaag aagccggtat ggattctgat gctaaaactg ttctttatga   2940
tggtcgcaca ggggagccgt ttgataatcg tgtatcagtt ggtgttatgt atatgattaa   3000
acttcaccac atggttgatg ayaaccattt tgtctatgca magwtcagtt ggcccttakt   3060
caaygawtam tcagasgart tcctgctwgg tgtaaaggct ncaattgtct ttagaggtta   3120
aggctggtga ataacggta tgctggtatt gatggcaatg ggcaagtgaa tantcaacac    3180
cggccgtcta cancgtgc                                                  3198
```

<210> SEQ ID NO 5
<211> LENGTH: 3096
<212> TYPE: DNA
<213> ORGANISM: Enterococcus faecalis

<400> SEQUENCE: 5

```
gacccttatc aattggtttt tagatgaggg acttcgtgaa atgtttgaag acatttacc     60 aattgatgat ttccaaggaa acttatcctt agaatttgtt gactatgaat taaaagaacc   120
aaagtacaca gtgaagaag cccgcgcaca tgatgccaac tattctgcgc cattacatgt    180
aacattacgt ttaaccaacc gtgaaacagg tgaaattaaa tcccaagaag tcttcttcgg   240
cgatttccca ttaatgacag aaatgggtac cttcatcatc aacggggcag aacgtgttat   300
cgtttcccaa ttagttcgtt ctccaggtgt ttacttccat ggaaaagtgg acaaaaacgg   360
caaagaaggt tttggctcaa cagtcattcc taaccgtggt gcatggttag aaatggaaac   420
agatgcgaaa gacatttctt atgttcggat tgaccgcaca cgtaaaattc ctttaactgt   480
```

```
gttagttcgt gctttaggtt tcggttcaga tgataccatc ttcgaaattt tcggcgacag    540
cgaaagctta cgcaacacaa ttgaaaaaga tttacacaaa aacgcaagtg attctcgtac    600
agaagaaggc ttgaaagaca tttatgaacg tcttcgccca ggcgaaccaa aaacagcaga    660
tagctcacgt agcttgttaa cttgcacgtt tctttgatcc aaaacgttat gatttggcaa    720
acgttggtcg ctacaaagtt aacaaaaaat tagacttaaa aacacgtcta ttaaacttaa    780
ccttagctga aacgctagtt gatccagaaa ctggtgtaaa tcattgtcga aaaaggcaca    840
gttttaacac actacatcat ggaaacatta aggcrataca ttgacaaacg gcttaaacag    900
cgtaacttac tatccaagtg aagatgcggt agtaactgaa ccaatgacga tccaagtgat    960
tcaagttctt tcaccaaaag atcctgaacg tatcgtaaat gtgattggta acggctatcc   1020
agacgacagc gtaaaaacag ttcgtccagc agatatcgtt gcttcaatga gctacttctt   1080
caacttaatg gaagatatcg gtaatgtcga tgacatcgac cacttaggta atcgtcgtat   1140
ccgttcagta ggcgaattat tacaaaacca attccgtatt ggtttagccc gtatggaacg   1200
tgtggttcgt gaaagaatgt ctattcaaga cacagaaaca ttgacaccac aacaattaat   1260
taacatccgt ccagtggtag caagtatcaa agaattcttt ggttcttcac agttatcaca   1320
gttcatggac caaacaaacc cattaggtga gttaacccat aaacgtcgtc tatcagcctt   1380
agggcctggt ggtttgactc gtgatcgtgc cggttatgaa gttcgtgacg ttcactactc   1440
tcactatggt cgtatgtgtc caattgaaac gcctgaggga ccaaatatcg ggttgatcaa   1500
tagcttatct agttatgcga aagtgaataa atttggtttc atcgaaacgc cttatcgccg   1560
tgttgatcgt gcgacaggcc gtgttactga tcaagtagat tacttaacag cagacatcga   1620
agaccattat atcgtagcgc aagcgaactc acttttaaat gaagatggca catttgccaa   1680
tgatgttgtt atggcgcgtc tacaaagtga aaacttagaa gttgccgtag acaaagttga   1740
ctacatggac gtttcaccaa aacaagtagt cgcagtcgca acagcatgta ttcctttctt   1800
agaaaacgat gactccaacc gtgccttgat gggtgccaac atgcagcgtc aagcggtgcc   1860
gttaattcaa ccacgctctc cgtgggtagg tacaggtatg gaatataaat cagcccatga   1920
ctcaggtgct gctttactat gtaaacatga cggtgtcgta gaattcgtcg atgcaaaaga   1980
aattcgcgtt cgtcgcgaca atggcgcatt agacaaatat atggttacaa aattccgtcg   2040
ttctaactca ggaacaagct acaaccaacg cccaattgtt cacttaggtg aaaagttgaa   2100
aaggcgatac tttaccggat ggaccttcta tggaagaagc gaaatggctt tatgcaaaa    2160
cgtcttagtt gccttcatga catgggaagg ttacaactac gaggatgcca ttatcatgag   2220
ccgtcgttta gttaaagacg atgtctacac ttctgtgcat attgaagaat atgaatcaga   2280
agcacgtgat acaaaattag gacctgaaga aattacccgt gaaattccaa acgttgggga   2340
agacgcgttg aaagacttag acgaaatggg gattatccgc attggtgctg aagttcaaga   2400
tggcgactta ctagttggga aagtcacacc taaagggtc acagaattat ctgcagaaga    2460
acgttattta cacgcaatct tcggggaaaa agcccgcgaa gttcgtgata cgtctctccg   2520
tgtacctcac ggtggcggcg gtatcgttca tgatgtgaaa atctttactc gtgaagctgg   2580
cgatgaatta tcaccaggtg tcaacatgtt agttcgtgtc tatatcgttc aaaaacgtaa   2640
aattcacgaa ggagataaaa tggcgggacg tcacggaaat aaaggggttg tttcccgtat   2700
tatgccggaa gaagatatgc cattcttacc tgacggaaca cctgttgata tcatgttgaa   2760
cccattaggg gtaccttctc gtatgaatat cggacaagta cttgaattac acttaggtat   2820
```

-continued

```
ggctgctcgc caattaggta ttcacgtcgc aacacctgtt ttcgatgggg caaccgatga    2880
agacgtttgg gaaactgttc gtgaagctgg tatggctagc gatgctaaaa cagttcttta    2940
cgatggacgt acaggtgaac catttgataa ccgtatttcc gttggtgtca tgtatatgat    3000
taaattagcc cacatggttg atgacaaatt gcatgctcgt tcaatcggac cttactctct    3060
tgttacgcaa caaccgttgg gtgtaaagct caattc                              3096
```

<210> SEQ ID NO 6
<211> LENGTH: 20
<212> TYPE: DNA
<213> ORGANISM: primer
<220> FEATURE:
<221> NAME/KEY: misc_feature
<222> LOCATION: (6)..(6)
<223> OTHER INFORMATION: n represents  a, t, c or g or i

<400> SEQUENCE: 6

```
aarytnggmc ctgaagaaat                                                  20
```

<210> SEQ ID NO 7
<211> LENGTH: 23
<212> TYPE: DNA
<213> ORGANISM: primer
<220> FEATURE:
<221> NAME/KEY: misc_feature
<222> LOCATION: (3)..(3)
<223> OTHER INFORMATION: n represents i
<220> FEATURE:
<221> NAME/KEY: misc_feature
<222> LOCATION: (3)..(3)
<223> OTHER INFORMATION: n represents a, t, c or g or i

<400> SEQUENCE: 7

```
tgnartttrt catcaaccat gtg                                              23
```

<210> SEQ ID NO 8
<211> LENGTH: 709
<212> TYPE: DNA
<213> ORGANISM: Streptococcus suis

<400> SEQUENCE: 8

```
cgcgaaattc caaacgttgg tgaagatgcc cttcgcaact tggacgaaat ggggattatc      60
cgtattggtg ccgaagttaa agagggcgac attcttgttg gtaaagtcac accaaaaggt     120
gaaaaagatc tttctgctga agagcgtctc ttgcacgcaa tcttcggtga caagtcacgt     180
gaagtacgtg atacctctct tcgtgtacct cacggtgccg atggtgtcgt tcgtgatgtg     240
aaaatcttta ctcgtgccaa cggtgatgaa ttgcaatcag gtgttaacat gttggttcgt     300
gtttacatcg ctcaaaaacg taagatcaag gtcggagata agatggccgg tcgtcacggt     360
aacaagggtg tcgtttcacg tattgtacct gttgaggata tgccatatct tccagatgga     420
acaccagttg acatcatgtt gaacccactc ggggtgccat cacgtatgaa catcggtcag     480
gttatggaac ttcacttggg tatggcggct cgcaacttgg gcatccatat cgcaacacca     540
gttttcgatg gtgcaagttc agaagacctc tggtcaactg ttaaagaagc aggtatggac     600
tcagatgcca agaccattct ttacgatgga cgtacaggtg aaccatttga caaccgtgta     660
tctgttggtg tcatgtacat gatcaagctt caccacatgg ttgatgaca               709
```

<210> SEQ ID NO 9
<211> LENGTH: 725
<212> TYPE: DNA

<213> ORGANISM: Streptococcus sanguinis

<400> SEQUENCE: 9

| | | | | | |
|---|---|---|---|---|---|
| tgtcatcaac | catgtggtga | gcttaatcat | gtacatgaca | ccgacagata | cacggttgtc | 60 |
| aaacggctca | ccggtacgtc | catcgtaaag | aatagtcttg | gcatcgctat | ccataccagc | 120 |
| ttcacggaca | gtatcccaga | ggtcttctga | gcttgctcca | tcaaagaccg | gtgtcgcaat | 180 |
| atggatgccc | aagttacgtg | ctgccatacc | aaggtgaagc | tccataacct | gaccaatgtt | 240 |
| catacgtgat | ggtaccccga | gtgggttcag | catgatatca | actggtgttc | cgtctggcaa | 300 |
| ataaggcatg | tcttccacag | gaacgatacg | ggatacaacc | ccttgtttc | cgtgacgacc | 360 |
| agccatctta | tctccgacct | tgatcttacg | tttttgagcg | atgtagacac | gaaccaacat | 420 |
| attaacgcca | gattgcaact | catcaccatt | agcacgggta | agatcttca | cgtcacgaac | 480 |
| cactccatca | gcaccgtgcg | gcacacgcag | agaggtatca | cggacttcac | gagacttgtc | 540 |
| tccgaagata | gcgtgcaaga | ggcgctcttc | agcagaaaga | tctttttcac | ccttaggggt | 600 |
| aactttacct | acaaggatat | cgccttcctt | gacttccgcc | ccgatgcgga | taatacccat | 660 |
| ttcgtccaaa | ttgcgtaggg | catcttcccc | tacgtttgga | atttcgcggg | taattcttca | 720 |
| ggtca | | | | | | 725 |

<210> SEQ ID NO 10
<211> LENGTH: 728
<212> TYPE: DNA
<213> ORGANISM: Streptococcus salivarius

<400> SEQUENCE: 10

| | | | | | |
|---|---|---|---|---|---|
| ttgtcatcaa | ccatgtgtga | agtttgatca | tgtacatgac | accaactgat | acacggttat | 60 |
| caaatggttc | acctgtacgt | ccatcgtaaa | ggattgtctt | agcatcacta | tccatacctg | 120 |
| cttcacgaac | agtatcccag | aggtcttctg | agcttgcccc | gtcaaagact | ggtgttgcga | 180 |
| tgtggatacc | caagttacga | gcagccatac | caaggtgaag | ttccataacc | tgaccgatgt | 240 |
| tcatacgtga | tggcacccca | gagggttca | acatgatatc | aactggtgta | ccgtctggaa | 300 |
| ggtaaggcat | gtcttcaaca | ggaacaatac | gagaaacaac | cctttgtta | ccgtgacgac | 360 |
| cggccatctt | atctccgacc | ttaatcttac | gttttgagc | gatgtaaaca | cgaacaagca | 420 |
| tgttaacacc | tgattgcaat | tcatcaccgt | ttgcacgtgt | gaagatttta | acatcacgaa | 480 |
| cgacaccatc | accaccgtga | ggtacacgga | gtgaggtatc | acgtacttca | cgagatttat | 540 |
| caccaaagat | agcatggaga | agacgttctt | cagcagaaag | gtcttttca | cccttaggtg | 600 |
| ttaccttacc | aacaagaatg | tcaccttctt | taacctcagc | accgatacgg | ataataccca | 660 |
| tttcgtcaag | gtctttgaga | gcttcttcac | caacgtttgg | caattcacgt | gtaatttctt | 720 |
| caggtcca | | | | | | 728 |

<210> SEQ ID NO 11
<211> LENGTH: 725
<212> TYPE: DNA
<213> ORGANISM: Streptococcus pyogenes

<400> SEQUENCE: 11

| | | | | | |
|---|---|---|---|---|---|
| tgtcatcaac | catgtggtga | agtttgatca | tatacatgac | accaacggat | acacggttgt | 60 |
| caaatggttc | accggtgcga | ccatcataaa | ggaccgtctt | agcatcgcta | tccataccag | 120 |
| cttcacgaac | agtgtcccaa | aggtcttctg | atgaagcccc | gtcaaagaca | ggtgttgcaa | 180 |
| tgtgaatacc | aagattacga | gcagccatac | caaggtgaag | ttccataacc | tgaccaatat | 240 |

```
tcatccgtga tggcacccca agagggttca acatgatgtc aactggtgtt ccgtctggaa    300
ggtatggcat gtcttcaact ggtacaatac gtgaaacgac acccttgttt ccgtgacgac    360
cggccatttt atctccgacc ttgattttac gttttttgagc gatgtaaaca cgcacaagca    420
tattaacacc tgattgcaat tcatcgccgt tagcgcgtgt aaagattttc acatcacgaa    480
cgataccatc accaccgtga gggacacgaa gtgaggtatc acgcacttca cgcgatttat    540
ccccaaagat ggcgtgaagt aaacgttctt cagcagaaag gtcttttttca cctttaggtg    600 tgactttacc tactaagatg tcgccttctt taacctcagc accgatacgg ataatgccca    660
tttcgtcaag gtctttgagg gcttcttcac caacatttgg gatttccgag tgattcttca    720
gggca                                                                725

<210> SEQ ID NO 12
<211> LENGTH: 724
<212> TYPE: DNA
<213> ORGANISM: Streptococcus pneumoniae

<400> SEQUENCE: 12
caaccatgtg gtggagtttg atcatgtaca tgactccgac agaaaacacg gttatcaaac     60
ggttcaccag tacgtccatc gtaaaggatc gttttggcat cgctatccat acctgcttct    120
ttaacagttg accaaagatc ttcagaactt gctccatcaa agactggtgt cgcgatgtga    180
ataccaagag tacgagctgc cataccaagg tgaagctcca taacctgacc gatattcata    240
cgtgatggta ccccaagtgg gttcaacatg atgtcgactg gagttccgtc tggaaggtaa    300
ggcatgtctt ctacaggaac gatacgagag acaacccctt tgtttccgtg acgtccggcc    360
attttatctc cgaccttaat cttacgtttt tgagcgatgt aaaacacgaac caacatgtta    420 acacctgatt gcaactcatc tccatttaca cgtgtaaaga tcttaacatc acgaacgaca    480
ccatcggcac cgtgtggtac acgaagagaa gtatcacgca cttcacgaga cttgtctcca    540
aagatagcgt gcaagagacg ttcttcagct gaaagatctt tctcaccctt aggtgttact    600
ttacctacaa gaatatcacc ttctttaacc tcagcaccaa tacggataat cccatttcgt    660
caaggtcttt gagggcatct tcaccaacgt tttggaattt cgcgagtgat tcttcaggt    720 ccaa                                                                 724

<210> SEQ ID NO 13
<211> LENGTH: 694
<212> TYPE: DNA
<213> ORGANISM: Streptococcus oralis

<400> SEQUENCE: 13
actcgtgaaa ttccaaacgt tggtgaagat gcccttaaag accttgacga aatgggtatt     60
atccgtattg gtgctgaggt taagaaagga gatatccttg taggtaaagt cacacctaag    120
ggtgaaaaag acctttctgc tgaagaacgt ctcttgcacg ctatcttcgg agacaagtct    180
cgtgaagtgc gtgatacttc tcttcgagta cctcacggtg ccgatggtgt cgttcgtgat    240
gttaagatct ttacacgtgc aaatggtgat gagttgcaat ctggtgtgaa tatgctggtt    300
cgtgtctaca tcgctcaaaa acgtaagatc aagtcggaga taagatggcc ggacgtcacg    360
gaaacaaagg ggttgtctct cgtatcgttc ctgtagaaga catgccttac cttccagatg    420
gaactccagt cgatatcatg ttgaacccac ttggggtgcc atcacgtatg aatatcggtc    480
aggttatgga actccacctt ggtatggcag cccgtactct tggtatccac atcgcaacac    540
```

```
cagtctttga cggagcaagt tcggaagacc tttgggacac tgttaaagaa gcaggtatgg    600
atagcgatgc caaaacaatc ctttacgatg gacgtacagg tgagccgttt gacaaccgtg    660
tatcagttgg tgtcatgtac atgatcaaac tcca                                694

<210> SEQ ID NO 14
<211> LENGTH: 728
<212> TYPE: DNA
<213> ORGANISM: Streptococcus mutans

<400> SEQUENCE: 14
tgtcatcaac catgtggtga agtttaatca tatacataac accaactgat acacgattat     60
caaacggctc ccctgtgcga ccatcataaa gaacagtttt agcatcagaa tccataccgg    120
cttcttttac tgtttcccaa agatcatcag aagttgctcc gtcaaagaca ggcgttgcaa    180
tatgaatgcc caaattacga gcagccatac caagatggag ttccataact tgcccaatgt    240
tcatccgtga tggcaccccca gtggattaa gcatgatatc aacaggtgtt ccatctggaa    300
gatatggcat atcttccact ggtacaatac gggaaacgac acccttgtta ccatgacgtc    360
cggccatctt atctccgacc ttgattttac gttttttgagc gatataaaca cgaaccagca    420
tgttaacacc tgattgaagt tcatctccat tagcacgtgt aaagattttc acatcacaaa    480 caaccgtc gccaccatga ggtacacgaa gagaagtatc acgaacttca cgtgatttgt    540
caccaaaaat ggcatgcaag aggcgttctt ctgcagaaag atcttttct cctttaggag    600 tcactttacc aactagaata tcaccttctt taacctcagc accaatgcga ataattccca    660
tttcatcaag gtctttcagg gcatcttcac caacatttgg gatttcacgc gtaatttctt    720
caggtcca                                                             728

<210> SEQ ID NO 15
<211> LENGTH: 730
<212> TYPE: DNA
<213> ORGANISM: Streptococcus mitis

<400> SEQUENCE: 15
tgtcatcaac catgtggtgg agtttgatca tgtaacatga ctccgacaga aaacacggtt     60
atcaaatggt tcacctgtac gtccatcgta aaggattgtt ttggcatcgc tatccatacc    120
agcttcttta acagttgacc aaagatcttc agaacttgct ccgtcaaaga ctggtgttgc    180
gatgtgaata ccaagagtac gagctgccat cccaaggtgg agttccataa cctgaccgat    240
attcatacgt gatggcaccc caagtgggtt caacatgata tcgactggag ttccatctgg    300
aaggtaaggc atatcttcta caggaacgat acgagagaca accctttat ttccgtgacg    360 tccggccatc ttatctccga ccttgatctt acgttttga gcgatgtaga cgcgaaccag    420
catgttgaca cctgattgca attcatctcc atttgcacgt gtaaagatct taacatcacg    480
aaccacacca tcagctccgt gtggtacacg aagagaagtg tcacgtactt cacgagattt    540
atctccgaag atagcgtgca agagccgttc ttcagctgaa aggtctttct caccccttagg    600 tgttacttta cctacaagga tatcccttc tttaacctca gcaccgatac ggataatacc    660
catttcgtca agatctttaa gggcatcttc cccaacgttt gggatttcac gagtaatttc    720
ttcaggtcca                                                           730

<210> SEQ ID NO 16
<211> LENGTH: 697
<212> TYPE: DNA
<213> ORGANISM: Streptococcus equinus
```

```
<400> SEQUENCE: 16
cactcgcgaa attccaaacg ttggtgaaga agctcttaaa gaccttgacg aaatgggtat      60
tatccgtatc ggtgctgaag ttaaagaagg tgacatcctt gtaggtaaag taacacctaa     120
aggtgaaaaa gacctttctg ctgaagagcg ccttcttcac gcaatcttcg gtgataaatc     180
acgtgaagtt cgtgatacat cacttcgtgt accacacggt ggagatggtg tcgttcgtga     240
cgttaaaatc tttacacgtg caaacggtga tgaattacaa tcaggtgtta acatgctcgt     300
tcgtgtttat atcgcacaaa aacgtaaaat caaagtcgga gataaaatgg ccggtcgtca     360
cggtaacaaa ggggttgttt ctcgtgttgt tccagttgaa gacatgcctt atcttccaga     420
cggaactcca gtcgatatca tgttgaaccc acttggggtg ccatctcgta tgaacatcgg     480
acaagttatg gagcttcacc ttggtatggc tgctcgtaac cttggtattc acattgcaac     540 accagtctttt gatggggcaa cttctgaaga ccctttgggat acagttaacg aagctggtat     600
ggctagcgac gctaagacag ttcttacga tggacgtact ggtgaaccat ttgataaccg     660
tgtgtcagtt ggtgtcatgt acatgattaa acttcac                              697

<210> SEQ ID NO 17
<211> LENGTH: 731
<212> TYPE: DNA
<213> ORGANISM: Streptococcus constellatus

<400> SEQUENCE: 17
agttgtcatc aaccatgtgt gcaatttaat catatacatg acaccgacag atacacggtt      60
gtcaaacggc tcgcccgtac gaccatcata agaatcgtc ttggcatcgc tatccatgcc     120
tgcttcacga acagtatccc aaaggtcatc tgagcttgct ccgtcaaata ctggcgttgc     180
tatgtggata ccaaggttgc gagcagccat accaaggtga agctccataa cctgtccgat     240
attcatacgt gatggcaccc caagtgggtt caacatgatg tctactggtg ttccgtctgg     300
aagataaggc atatcctcaa ctggaacgat acgggaaaca acccctttat ttccgtggcg     360
tccggccatc ttatccccaa cgcggatctt tcgtttttga gcaatgtaaa cacgcaccaa     420
catgttgaca ccagattgca attcatcacc gttcgcacga gtaaagattt tcacatcacg     480
gacaacccca gcaccaccat gtggtacacg aagagatgtg tcacgtactt cacgagattt     540
atcaccgaaa attgcatgaa gcaggcgttc ttcagcggat aagtctttttt cacctttcgg     600 cgttacttta ccgacaagaa tgtcgccctc tttcacctca gcaccaatgc ggataattcc     660
catttcgtca aggtctctta gcgcatcttc cccaacgttt ggaatttcgc gcgtaatttc     720
ttcaggtcca a                                                          731

<210> SEQ ID NO 18
<211> LENGTH: 697
<212> TYPE: DNA
<213> ORGANISM: Streptococcus anginosus

<400> SEQUENCE: 18
cacgcgcgaa attccaaacg tcggtgaaga tgctttgaga gaccttgacg aaacgggaat      60
tatccgcatt ggtgctgagg taaaagaagg cgacattctt gtcggtaaag taacaccgaa     120
aggtgaaaaa gacttatctg ctgaagaacg cctgcttcat gcaattttcg gtgataaatc     180
tcgtgaagta cgtgatactt cccttcgtgt accacatggt ggtgcagggg ttgtccgtga     240
tgtgaaaatc tttactcgtg cgaacggtga tgaattgcaa tctggtgtca acatgttggt     300
```

```
acgtgtttac atcgctcaaa aacggaaaat ccgtgttggg gataagatgg ctggacgtca    360
cggaaacaaa ggggttgttt cccgcattgt tccagttgag gatatgccgt atcttccaga    420
tggaacacca gttgatatta tgttgaaccc acttggggtg ccatctcgta tgaatattgg    480
tcaagttatg gagcttcacc tcggtatggc tgctcgcaac cttggcattc acattgcaac    540
accagtattt gacggggcta gctcagatga tctttgggaa accgttcgtg aagctggcat    600
ggatagcgat gctaagacaa tccttttatga tggccgtact ggtgagccat ttgataatcg    660
tgtatccgtt ggtgtcatgt acatgatcaa actccac                              697
```

```
<210> SEQ ID NO 19
<211> LENGTH: 728
<212> TYPE: DNA
<213> ORGANISM: Streptococcus dysgalactiae

<400> SEQUENCE: 19
tgtcatcaac catgtggtgg agtttaatca tgtacatgac accaacggat acacggttgt     60
caaatggttc gccagtacgt ccatcataaa ggaccgtctt agcatcgcta tccataccag    120
cttcacgaac agtgtcccaa aggtcttctg atgaagcccc gtcaaagaca ggtgttgcaa    180
tgtgaatacc aagattacga gcagccatac caaggtgaag ttccataacc tgaccaatgt    240
tcatccgtga tggcacccca agagggttca acatgatgtc aactggtgtt ccatctggaa    300
ggtatggcat gtcttcaact ggtacaatac gtgaaacgac accttgtttt ccgtgacgac    360
cagccatttt atctccgact ttgatcttac gttttttgagc aatgtaaaca cgcacaagca    420
tattaacacc tgattgcaat tcatcgccgt tagcgcgtgt aaagattttc acatcacgaa    480
cgataccatc accaccgtga ggtacacgaa gggacgtatc acgaacttca cgtgatttat    540
ctccaaagat ggcatgcaag agacgctctt cagcagaaag gtcttttttca cctttaggtg    600 tgactttacc tactaagatg tcgccttctt taacctcagc accgatacgg ataattccca    660
tttcgtcaag gtcttttgagc gcttcttcac caacgtttgg aatttcgcgg gtgatttctt    720
caggtcaa                                                              728
```

```
<210> SEQ ID NO 20
<211> LENGTH: 728
<212> TYPE: DNA
<213> ORGANISM: Streptococcus bovis

<400> SEQUENCE: 20
tgtcatcaac catgtggtga agtttgatca tgtacatgat accaacagag acacgattat     60
caaatggttc acctgtacga ccgtcataaa gaactgtctt agcgtcgcta tccataccag    120
cttcacgaac agtatcccaa aggtcttctg aagttgcccc gtcaaagact ggagttgcaa    180
tgtgaatacc gaggttacga gctgccatac caaggtgaag ttccataact tgtccgatat    240
tcatacgaga tggcacccca agagggttca acatgatatc aactggagtt ccgtctggaa    300
gatatggcat gtcttcaaca ggaacgatac gagaaacaac ccctttgttt ccgtgacgac    360
cggccatttt atctccgact ttgattttac gttttttgtgc aatgtaaaca cgaacgagca    420
tgttgacacc tgattgcaat tcatcaccgt tagcacgtgt aagattttta acatcacgaa    480
caacaccgtc tccaccgtgt ggcacacgaa gtgatgtatc acgtacttca cgagatttat    540
caccgaagat tgcgtgaaga aggcgttctt cagcagaaag gtcttttttca cctttaggtg    600 ttactttacc tacaaggata tcaccttctt taacttcagc accgatacgg ataatacccca    660 tttcgtcaag gtctttaaga gcttcttcac caacgtttgg aatttcgcga gtgatttctt    720
```

-continued caggtcaa                                                              728

<210> SEQ ID NO 21
<211> LENGTH: 728
<212> TYPE: DNA
<213> ORGANISM: Streptococcus acidominimus

<400> SEQUENCE: 21
ttgtcatcaa ccatgtggtg gagcttaatc atgtacatga caccaacaga cacacggtta     60
tcaaatggtt caccagtacg accatcataa agaatcgttt tagcatcgct gtccattcct    120
gcctctttaa cagttgacca gagatcctct gagctcgcac catcgaaaac cggtgttgcg    180
atatggatac ccaagttacg agcagccata cccaagtgca gttccataac ctgaccaata    240
ttcatacgag atggcacccc aagtgggttc aacatgatgt caactggtgt tccatctgga    300
agatatggca tgtcttcaac tggtacaata cgagaaacga cacccttgtt accgtgacga    360
ccggccatct tatctccgac cttaatcttg cgttttgag cgatatacac acgtaccagc     420
atattaacac cagactgtag ctcatcacca ttagcacgcg taaagatttt cacatcacga    480
acaacaccat ctgcaccgtg tggcacacgt agagaggtat cacgtacttc acgtgatttg    540
tcaccgaaga tagcatgcaa gagacgctcc tcagcagaaa gatcttttc accttttggt    600 gtcaccttac caacaagaat atcgccttct ttaacttctg caccgatacg ataataccc     660 atttcgtcaa ggtctttgag ggcttcttca ccaacgtttg gaatttcacg agtaatttct    720
tcaggtca                                                              728

<210> SEQ ID NO 22
<211> LENGTH: 733
<212> TYPE: DNA
<213> ORGANISM: Streptococcus agalactiae

<400> SEQUENCE: 22
tgagttgtca tcaaccatgt ggtgaagttt gatcatgtac atgacaccaa ctgacacacg     60
gttatcgaat ggttcaccag tacgaccatc ataaagaaca gtcttagcat ctgaatccat    120
acctgcttct tgaacagttt cccaaaggtc ttctgaagaa gccccatcaa agactggcgt    180
tgcaatatga atacctaaat tacgagcagc catacctaaa tgaagctcca taacttgtcc    240
gatattcata cgtgatggca ccccaagtgg gttcaacatg atatcaactg gcgttccatc    300
tggtaagtaa ggcatatctt caacaggaac aatacgtgag acgacacctt tgtttccgtg    360
acgaccggcc atcttatcac cgactttgat tttacgtttt tgagcgatat aaacgcggac    420
aagcatatta acacctgatt gcaattcatc accatttgca cgagtaaaga ttttaacgtc    480
acgaactact ccatcgccac cgtgaggtac acgtagtgaa gtatcacgaa cttcacgtga    540
tttatcacca aaaatggcat gcaagagacg ttcttcagca gataagtcct tttcaccctt    600
aggtgttacc ttaccaacaa gaatgtcacc ttcttttacc tcagcaccaa tgcggataat    660
tcccatttca tcgagatcac gtagtgaatc ttcaccaaca ttttggattt cacgagtaat    720
ttcttcaggt cca                                                       733

<210> SEQ ID NO 23
<211> LENGTH: 714
<212> TYPE: DNA
<213> ORGANISM: Streptococcus difficilis

<400> SEQUENCE: 23

```
ttgtcatcaa ccatgtggtg aagtttgatc atgtacatga caccaactga cacacggtta      60
tcgaatggtt caccagtatg accatcataa agaacagtct tagcatctga atccatacct     120
gcttcttgaa cagtttccca aaggtcttct gaagaagccc catcaaagac tggcgttgca     180
atatgaatac ctaaattacg agcagccata cctaaatgaa gctccataac ttgtccgata     240
ttcatacgtg atggcacccc aagtgggttc aacatgatat caactggcgt tccatctggt     300
aaataaggca tatcttcaac aggaacaata cgtgagacga cacctttgtt tccgtgacga     360
ccggccatct tatcaccgac tttgatttta cgttttttgag cgatataaac gcggacaagc     420
atattaacac ctgattgcaa ttcatcacca tttgcacgag taaagatttt aacgtcacga     480
actactccat cgccaccgtg aggtacacgt agtgaagtat cacgaacttc acgtgattta     540
tcaccaaaaa tggcatgcaa gagacgttct tcagcagata gtccttttc acccttaggc     600 gttaccttac caacaagaat gtcaccttct tttacctcag caccaatgcg ataattccc      660 atttcatcga gatcacgtag tgaatcttca ccaacatttg gaatttcacg agta           714

<210> SEQ ID NO 24
<211> LENGTH: 728
<212> TYPE: DNA
<213> ORGANISM: Streptococcus intermedius

<400> SEQUENCE: 24
tgtcatcaac catgtggtga agcttaatca tgtacatgac accaacggac acacggttat      60
caaacggttc gccagtacgt ccatcataaa ggattgtctt agcatcgcta tccatacctg     120
cttcacgaac ggtttcccaa agatcatctg agctagctcc gtcaaagact ggcgttgcaa     180
tgtggatacc aaggttgcga gcagccatac cgaggtgcaa ttccataact tgtccgatat     240
tcatacgtga cggcacccca agaggattca acatgatatc aactggtgtc ccgtctggaa     300
gatacggcat atcctcaact ggaacaatgc gggaaacaac ccctttgttt ccgtggcgtc     360
cggccatctt atctccaacg cggatttccc gttttttgagc gatataaaca cgtaccaaca     420
tgttgacacc ggattgcaat tcatcaccgt tcgcacgagt aaagatttt acatcacgga     480 caacacctgc accaccgtgt ggtacacgaa gggaggtatc acgcacttca cgagactat      540 caccaaaaat tgcatgaagc aggcgttctt cagcggataa atcttttca cctttcggcg     600 ttactttacc gacaagaatg tcgccttctt ttacctcagc accaatgcgg ataattccca     660
tctcgtcaag gtctctcaaa gcatcttccc cgacgtttgg aatttcgcgc gtgatttctt     720
caggtcca                                                              728

<210> SEQ ID NO 25
<211> LENGTH: 728
<212> TYPE: DNA
<213> ORGANISM: Streptotoccus equi

<400> SEQUENCE: 25
tgtcatcaac catgtggtga agcttaatca tatacatgac accaactgac acacgattat      60
caaacggctc accagtacgg ccatcataaa gaacagtctt agcatcgcta tccatacctg     120
cttcacgaac agtttcccaa aggtcctcag acgtagctcc gtcaaagacc ggtgttgcga     180
tatggatacc caaattacga gcagccatac ctaggtgaag ctccataacc tgtccaatgt     240
tcatacgaga cggcacccca agagggttca gcatgatgtc aacaggggtt ccgtctggca     300
gatatggcat atcctcaacc ggtacaatac gtgagacgac acccttgtta ccatgacgcc     360
cggccatttt atctccgacc ttgatttac gcttttgagc aatgtaaaca cgcaccagca     420
```

```
tattaacacc tgattgaagc tcatcaccat ttgcgcgtgt aaagatcttc acatcacgta      480
caatcccgtc accaccatga ggaacacgta acgaggtatc acgaacctca cgtgatttat      540
caccaaagat agcatgcagg agacgttctt cagcagaaag gtcttttttca cccttaggag      600 ttaccttacc aacaagaata tcgccttcct tgacctctgc accgatacgg ataatacccca     660 tttcatcaag gtccttgagg gcttcttcac caacgtttgg cacttcacgt gtgatttctt      720
caggtcca                                                               728

<210> SEQ ID NO 26
<211> LENGTH: 697
<212> TYPE: DNA
<213> ORGANISM: Enterococcus gallinarum

<400> SEQUENCE: 26
cactcgtgaa atcccgaatg tcggggaaga cgcattgaaa gatctagacg aaatgggtat       60
catccgcatt ggtgcggaag tcaaagatgg cgatctgttg gttggtaaag taacgcctaa      120
aggggtaacg gaactatctg cagaagaacg cttgcttcat gcaatctttg gtgaaaaagc      180
ccgcgaagtc cgcgatactt ctctgcgcgt acctcacggt ggtggcggaa tcgtccatga      240
tgtgaaaatc tttacccgcg aagctggcga tgaattgtca ccaggtgtca atatgctcgt      300
tcgcgtgtat atcgttcaaa aacggaaaat ccatgaaggg gataaaatgg ccggccgtca      360
cggaaataaa ggggtcgttt ctcgcattat gccagaagaa gacatgcctt tcttaccaga      420
cggtacacca gttgatatca tgttgaaccc attaggggtg ccttcacgga tgaacattgg      480
acaagtattg gaattacact taggaatggc tgcccgccaa ttaggaatcc acgtggctac      540
accagtcttt gatggtgcca gcgatgaaga tgtctgggca acagttgcag aagccggcat      600
ggctagcgac gccaaaaccg ttttgtatga tggccgtact ggagaaccat ttgatggtcg      660
aatctccgta ggtgtcatgt atatgatcaa attggcc                              697

<210> SEQ ID NO 27
<211> LENGTH: 727
<212> TYPE: DNA
<213> ORGANISM: Enterococcus casseliflavus

<400> SEQUENCE: 27
tgtcatcaac catgtgggcc aatttgatca tgtacatgac accaacggag atgcggccat       60
caaatggttc gccggtacgt ccgtcgtaaa gcactgtttt ggcatcgctg gccattcctg      120
cttcagcaac cgttgcccaa acatcttcat cgctggctcc atcaaagact ggtgttgcca      180
cgtgaatgcc taattgacgc gcagccattc ctaagtgtaa ctctaatact tgtccaatgt      240
tcatccgaga aggtacccct aatgggttca gcatgatatc gactggtgtg ccatctggta      300
agaaaggcat gtcttcttct ggcataatgc gagaaacgac ccctttgttt ccgtgacgtc      360
cggccatttt atccccttca tggatttttcc gttttttgaac gatataaacg cgaaccagca      420
tgttcacacc tggtgacaat tcatcgccag cttcgcgggt aaagattttg acatcgtgga      480
cgattccgcc gccgccgtga ggcacgcgta gagaagtgtc acgcacttcg cgggcttttt      540
caccaaagat tgcgtgcaac aaacgctctt ctgctgaaag ttccgttacc ccttttggcg      600
tgactttccc aacaagcaga tcgccatctt tgacttccgc accaatgcgg ataatgccca      660
tttcgtctag gtcttttcaac gcgtcttccc aacgttcggg atttcgcgag tgatttcttc      720
aggtcca                                                                727
```

<210> SEQ ID NO 28
<211> LENGTH: 721
<212> TYPE: DNA
<213> ORGANISM: Enterococcus saccharolyticus

<400> SEQUENCE: 28

```
tgtcatcaac catgtgggca agtttaatca tgtacattac cccaacagag atacgaccat      60
cgaatggttc acccgtacgt ccgtcataaa gaacagtttt cgcatcgcgc gccatgcccg     120
cttcgcgaac tgtttcccat acgtcatcat ctgatgcacc atcaaatact ggtgtagcta     180
catggatgcc taactgacgt gcagccatcc ctaagtgtaa ttccaatact tgtccgatgt     240
tcatacgaga tggtactcct agtgggttca acatgatatc aactggtgtg ccgtctggta     300
agaatggcat gtcttcttct ggcataatgc gagagacaac ccctttgtta ccatgacgtc     360
ccgccatttt atctccttcg tgaatcttac gttttttgcac gatataaaca cgaactaaca     420
tgttcacacc tggagataat tcgtcgcctg cttcacgggt aaagatttta acatcgtgaa     480
cgataccgcc accgccgtga ggaacacgta atgatgtatc acgtacttca cgtgcttttt     540
caccgaagat tgcgtgcaat agacgttctt ctgcagataa ttcggttacc cctttaggag     600
tgactttacc tactaataag tcgccatctt gtacttcggc accgatacgg ataatacca      660
tttcgtctaa gtctttttaat gcgtcttccc caacgttagg aatttcgcgt gtattcttca     720
g                                                                     721
```

<210> SEQ ID NO 29
<211> LENGTH: 727
<212> TYPE: DNA
<213> ORGANISM: Enterococcus faecium

<400> SEQUENCE: 29

```
tgtcatcaac catgtgagca agtttgatca tgtacatcac accgacagac acacgtccat      60
caaatggttc acctgtacgt ccgtcgtaca gaacagtttt cgcatcgctg gccataccgg     120
cttcacgaac tgtttcccat acgtcttcat cacttgcacc atcaaatact ggcgttgcta     180
cgtggatacc taactgacgt gcagccatac ccaagtgtaa ttccaatact tgcccgatgt     240
tcatacgtga aggcacccct aaaggattca gcatgatatc gattggtgtt ccatcaggta     300
ggaatggcat atcttcttcc ggcataatac gggatacaac ccctttattt ccgtgacgac     360
cggccatttt atcccttca tggattttac gttttttgaac gatataaaca cgaactaaca     420
tgtttacgcc tggtgacaat tcatctccag cttcacgagt aaagattttc acatcgtgaa     480
cgataccgcc gccgccatgt ggtacacgta atgatgtatc gcggacttca cgagcttttt     540
cgccaaagat cgcatgcaat agacgttctt ctgcagataa ttctgttacc ccttttggcg     600
tgactttccc tacaagcaaa tcgccatctt ggacttctgc accaatacgg atgatacca      660
tttcgtctaa atcttttaat gcgtcttccc gacattaggg atttcgcgtg tgatttcttc     720
aggtcca                                                                727
```

<210> SEQ ID NO 30
<211> LENGTH: 725
<212> TYPE: DNA
<213> ORGANISM: Enterococcus faecalis

<400> SEQUENCE: 30

```
tgtcatcaac catgtgggct aatttaatca tatacatgac accaacggaa atacggttat      60
caaatggttc acctgtacgt ccatcgtaaa gaactgtttt agcatcgcta gccataccag     120
```

```
cttcacgaac agtttcccaa acgtcttcat cggttgcccc atcgaaaaca ggtgttgcga    180
cgtgaatacc taattggcga gcagccatac ctaagtgtaa ttcaagtact tgtccgatat    240
tcatacgaga aggtacccct aatgggttca acatgatatc aacaggtgtt ccgtcaggta    300
agaatggcat atcttcttcc ggcataatac gggaaacaac ccctttattt ccgtgacgtc    360
ccgccatttt atctccttcg tgaattttac gttttgaac gatatagaca cgaactaaca    420
tgttgacacc tggtgataat tcatcgccag cttcacgagt aaagattttc acatcatgaa    480
cgataccgcc gccaccgtga ggtacacgga gagacgtatc acgaacttcg cgggcttttt    540
ccccgaagat tgcgtgtaat aaacgttctt ctgcagataa ttctgtgacc cctttaggtg    600
tgactttccc aactagtaag tcgccatctt gaacttcagc accaatgcgg ataatcccca    660
tttcgtctaa gtctttcaac gcgtcttccc aacgtttgga atttcacggg tatttcttca    720
ggtca                                                                725
```

<210> SEQ ID NO 31
<211> LENGTH: 570
<212> TYPE: DNA
<213> ORGANISM: Enterococcus avium

<400> SEQUENCE: 31

```
gtccatcata aagaacggtc ttagcatctg ctgccatacg agcttcacga actgtttccc     60
aaacatcgct atcttgcgca ccatcgaaga ctggtgtcgc aacatggata cctagttggc    120
gagccgccat tcccaagtgt aattccaaca cttgtccgat gttcatccga gatggcacac    180
ctaatgggtt caacatgata tcaactggcg taccgtctgg taagaaaggc atgtcttctt    240
ctggcataat gcgagaaacg acccctttat tccgtgacgg ccggccatt ttatcccctt    300
catgaatctt acgtttttgc acgatgtaca cgcgcactaa catatttaca cctggagata    360
attcatcgcc tgcttcacga gtaaagatct tcacatcgtg aacgatcccg ccgccaccat    420
gcggtacacg aagagatgta tcacgaactt cacgagcctt tcaccaaag atcgcatgca    480
acaaacgttc ttcagctgat aattctgtta ccccttaggg agtgacttta ccaactaata    540
aatcaccatc atgaacttca gcaccaatac                                     570
```

<210> SEQ ID NO 32
<211> LENGTH: 732
<212> TYPE: DNA
<213> ORGANISM: Abiotrophia defectiva

<400> SEQUENCE: 32

```
gaagttgtca tcaaccatgt gggccaactt aatcatgtac ataaccccaa cagagacttt     60
acggtcaaat ggttcaccgg ttcgaccatc atataagata gtcttagcgt cagcttctaa    120
gccggcttcc ttaactgttt cccagacatc ttcttcacta gcaccgtcaa agacaggtgt    180
tgcaatcttg atgcccattt cgcgagcagc catccccaag tgtaactcta ggacttgccc    240
gatgttcata cgggatggaa cccctaatgg gttcaacatg atatcaactg gggtaccatc    300
tggtaagaat ggcatatctt cttccggcat gataagggag acaaccctt tgttaccgtg    360 acgaccggcc atcttatccc cttcattgat tttacgtttt tgtacgatgt agacgcggac    420
tagcttgttg acacctggtg ccaattcgtc gccagcttcg cgggtaaaga ttttaacgtc    480
gtggacaatc ccgcccccgc cgtgtggcac acgcaaggaa gtatcacgta cttcacgcgc    540
cttctcaccg aagatagcat ggagcaagcg ttcttccgca gacaactcgg tcacaccttt    600
tggtgttacc ttaccaacta agatatcgcc gtcttttact tccgccccga tacagataat    660
cccgtcttgg tctaagtact tgagggcatc ttcggacacg tttggaattt cgcgtgtaat    720
ttcttcaggt ca                                                        732
```

<210> SEQ ID NO 33
<211> LENGTH: 727

```
<212> TYPE: DNA
<213> ORGANISM: Gemella morbilorum

<400> SEQUENCE: 33
tgtcatcaac catgtgtgca agtttatcat gtacattacc cctacagata cacggctatc    60
aaatggctca cctgtacgtc cgtcataaag aactgtctta gcatctttag ccattccagc   120
ttccgcaact gtagaccaaa catcttcatc agtagcacca tcgaatactg gtgtagctac   180
gtggattcca agttgtttag cagccatacc taagtgtagc tctaatactt gtccaatgtt   240
catacgagat ggaaccccaa gtgggtttaa cattacgtca actggtgtac catctggtag   300
gtaaggcata tcttcttctg gtaagatatt tgagataacc cctttgttac cgtgacgacc   360
ggccatttta tctcctacac gaattttacg tttttggacg ataaatacac gaacaagttc   420
atttacaccg ttaggtaatt cagcaccatc ttcacgttta aagattttaa catcagcaac   480
tactccatca gcaccgtgag gtacacgtaa tgaagtatca cgtacttctt tagatttagc   540
tccaaagata gcatataata attttcttc tggagtttgt tcagttaatc ctttcggtgt   600
aactttacct actaaaatat ctccatcttt aacttcagcc ccaatacgaa tgattcctcg   660
tgcatctaag tttctaagtg cattttcacc ctacgtttgg aatctcacga gtaatttctt   720
caggtca                                                              727

<210> SEQ ID NO 34
<211> LENGTH: 726
<212> TYPE: DNA
<213> ORGANISM: Gemella haemolysans

<400> SEQUENCE: 34
tgtcatcaac catgtgtgca agtttaatca tgtacattac ccctacagat acacggctat    60
caaatggctc acctgtacgt ccgtcataaa gaactgtctt agcatcttta gccattccag   120
cttccgcaac tgtagaccaa acatcttcat cagtagcacc atcgaatact ggtgtagcta   180
cgtggattcc aagttgttta gcagccatac ctaagtgtag ctctaatact tgtccaatgt   240
tcatacgaga tggaaccccca gtgggtttta acattacgtc aactggtgta ccatctggta   300
ggtaaggcat atcttcttct ggtaagatat ttgagataac ccctttgtta ccgtgacgac   360
cggccatttt atctcctaca cgaattttac gtttttggac gataaataca cgaacaagtt   420
catttacacc gttaggtaat tcagcaccat cttcacgttt aaagatttta acatcagcaa   480
ctactccatc agcaccgtga ggtacacgta atgaagtatc acgtacttct ttagatttag   540
ctccaaagat agcatataat aattttcttc tggagtttg ttcagttaat cctttcggtg   600
taactttacc tactaaaata tctccatctt taacttcagc cccaatacga atgattcctc   660
gtgcatctaa gtttctaagt gcattttcac ctacgtttgg aatctcacga gtattcttca   720
ggtcca                                                               726

<210> SEQ ID NO 35
<211> LENGTH: 719
<212> TYPE: DNA
<213> ORGANISM: Granulicatella adjacens

<400> SEQUENCE: 35
catcaaccat gtgagcaagt tgatcatgt acataacccc tactgacaca cggttatcga    60
atggttcccc tgtacgtcca tcatatagaa ttgttttcgc atcacgagcc atacccgctt   120
ctgcaacagt tccccatacg tcttcatctt gcgcaccatc gaatactggt gttgcgatgt   180
```

-continued

```
aaatacctaa ttcacgagca gccatcccta agtgtaactc taacacttgt ccgatgttca      240
tacgtgaagg taccoctaat gggtttaaca tgatgtcaac tggtgttcca tctggtaaga      300
atggcatatc ttcttccggc ataatacggg aaacaacccc tttattaccg tgacgtccgg      360
ccatcttatc cccttcattg attttacgtt tttgtacaat atatacacga actaatttgt      420
ttacgccagg tgctaattca tcacctgctg cacgtgtgaa tacacgtaca tcacggacaa      480
taccgccacc gccgtgaggt acacgtagag atgtgtcacg aacttcacga gcttttcac       540 cgaagattgc gtgtaataaa cgttcctctg gtgattgttc tgttaaccct ttaggagtta      600
ctttaccaac taagatgtca ccatctttaa cttcggcacc gatacgaata attccgtctg      660
cgtctaggtt cttcaatgcg tcttcccaac gtttggaatc tcacgagtaa ttcttcagg      719
```

<210> SEQ ID NO 36
<211> LENGTH: 21
<212> TYPE: DNA
<213> ORGANISM: primer

<400> SEQUENCE: 36
agacggacct tctatggaaa a                                                21

<210> SEQ ID NO 37
<211> LENGTH: 20
<212> TYPE: DNA
<213> ORGANISM: primer

<400> SEQUENCE: 37
ggacacatac gaccatagtg                                                  20

<210> SEQ ID NO 38
<211> LENGTH: 21
<212> TYPE: DNA
<213> ORGANISM: primer

<400> SEQUENCE: 38
gttgtaacct tcccawgtca t                                                21

<210> SEQ ID NO 39
<211> LENGTH: 20
<212> TYPE: DNA
<213> ORGANISM: primer

<400> SEQUENCE: 39
gtcttcwtgg gygatttccc                                                  20

<210> SEQ ID NO 40
<211> LENGTH: 21
<212> TYPE: DNA
<213> ORGANISM: primer
<220> FEATURE:
<221> NAME/KEY: misc_feature
<222> LOCATION: (8)..(8)
<223> OTHER INFORMATION: n represents i

<400> SEQUENCE: 40
accgtggngc wtggttrgaa t                                                21

<210> SEQ ID NO 41
<211> LENGTH: 20
<212> TYPE: DNA
<213> ORGANISM: primer

<400> SEQUENCE: 41

-continued aaccaattcc gyatyggtyt                                              20

<210> SEQ ID NO 42
<211> LENGTH: 20
<212> TYPE: DNA
<213> ORGANISM: primer
<220> FEATURE:
<221> NAME/KEY: misc_feature
<222> LOCATION: (3)..(3)
<223> OTHER INFORMATION: n represents i

<400> SEQUENCE: 42
agngggttta acatgatgtc                                              20

<210> SEQ ID NO 43
<211> LENGTH: 20
<212> TYPE: DNA
<213> ORGANISM: primer
<220> FEATURE:
<221> NAME/KEY: misc_feature
<222> LOCATION: (3)..(3)
<223> OTHER INFORMATION: n represents i

<400> SEQUENCE: 43
agngcccaaa cctccatctc                                              20

<210> SEQ ID NO 44
<211> LENGTH: 21
<212> TYPE: DNA
<213> ORGANISM: primer

<400> SEQUENCE: 44
ctccaagtga acagatgtgt a                                            21

<210> SEQ ID NO 45
<211> LENGTH: 26
<212> TYPE: DNA
<213> ORGANISM: primer

<400> SEQUENCE: 45
ttaccaaact taattgagat tcaaac                                       26

<210> SEQ ID NO 46
<211> LENGTH: 22
<212> TYPE: DNA
<213> ORGANISM: primer

<400> SEQUENCE: 46
agtatttatg ggtgatttcc ca                                           22

<210> SEQ ID NO 47
<211> LENGTH: 26
<212> TYPE: DNA
<213> ORGANISM: primer

<400> SEQUENCE: 47
ggacgttata aaatcaacaa aaaatt                                       26

<210> SEQ ID NO 48
<211> LENGTH: 23
<212> TYPE: DNA
<213> ORGANISM: primer

<400> SEQUENCE: 48

```
agttataacc atcccaagtc atg                                              23

<210> SEQ ID NO 49
<211> LENGTH: 23
<212> TYPE: DNA
<213> ORGANISM: primer

<400> SEQUENCE: 49
tgaagtttat catcaaccat gtg                                              23

<210> SEQ ID NO 50
<211> LENGTH: 18
<212> TYPE: DNA
<213> ORGANISM: primer

<400> SEQUENCE: 50
cccaaaacgt tgtccacc                                                    18

<210> SEQ ID NO 51
<211> LENGTH: 20
<212> TYPE: DNA
<213> ORGANISM: primer

<400> SEQUENCE: 51
aaccaagcyc ggttaggrat                                                  20

<210> SEQ ID NO 52
<211> LENGTH: 25
<212> TYPE: DNA
<213> ORGANISM: primer
<220> FEATURE:
<221> NAME/KEY: misc_feature
<222> LOCATION: (15)..(15)
<223> OTHER INFORMATION: n represents i

<400> SEQUENCE: 52
atgttgaacc cactngggt gccat                                             25
```

MOLECULAR IDENTIFICATION OF BACTERIA OF GENUS *STREPTOCOCCUS* AND RELATED GENERA

Figure 1:

The present invention pertains to the area of diagnosis. More precisely, the invention concerns a method for the molecular identification of bacteria of genus *Streptococcus* and related genera *Enterococcus, Gemella, Abiotrophia* and *Granulicatella* using detection and/or amplifying and sequencing techniques with probes or oligonucleotide primers applied to strains of these bacterial genera.

Bacteria of the *Streptococcus* genus and of four related genera: *Enterococcus, Gemella, Abiotrophia* and *Granulicatella*, are Gram-positive and catalase-negative spherical bacteria of which more than around forty species are presently known. Bacteria of the genus *Lactococcus*, previously classified among the streptococci as Group N *Streptococcus*, do not come within the scope of this invention on account of their rare occurrence in human pathology, and because they can be easily distinguished from streptococci through their growth at +10° C. Genus *Streptococcus* officially comprises 55 species. Genus *Gemella* comprises 6 species, genus *Abiotrophia* comprises 1 species, genus *Granulicatella* comprises 3 species, and genus *Enterococcus* comprises 24 species [www.springer-ny.com/bergeysoutline/main.htm]. These species are easily and frequently cultured from environmental samples, veterinary clinical specimens and human clinical specimens [Ruoff Kl. (1999) in Manual of Clinical Microbiology, pp. 283-296, ASM Press]. In man, different species of the *Streptococcus* genus are responsible for community infections which may be severe due to the invasive nature of the streptococci under consideration or through the production of possibly serious toxins with clinical signs distant from the site of infection. For example, *Streptococcus pyogenes* (Group A *Streptococcus*) is responsible for throat infections and post-streptococcal syndromes including rheumatic fever during which damage to the heart valves through an inflammatory process is responsible for possibly fatal heart valve disease. Also, several species of genus *Streptococcus*, in particular Group A, Group C and Group C Streptococci are responsible for life-threatening invasive infections, myositis in particular, i.e. degenerative changes to skin, subcutaneous and muscle tissue as has been described for some years. Also, *Streptococcus pneumoniae*(*pneumococcus*) for example causes pneumonia, meningitis and septicaemia. Bacteria of the genera *Streptococcus, Enterococcus, Gemella, Abiotrophia* and *Granulicatella* can cause endocarditis i.e. infection of the heart valves in man, which come under life-threatening infectious diseases [Casalta J P et al., Journal Clinical Microbiology, 2002, 40: 1845-1847]. Also, some species of the genera under consideration can cause nosocomial infections, for example group A *Streptococcus* bacteria are responsible for bacteraemia subsequent to digestive endoscopy investigation. In addition, bacteria of the genus *Enterococcus* can cause nosocomial urinary infections after prophylactic antibiotic therapy with cephalosporins against which they are naturally resistant. These bacterial species also raise the problem of their increasing resistance to antibiotics, the resistance of *Streptococcus pneumoniae* to penicillin G [Garav J. Lancet Infect. Dis. 2002, 2: 404-415] and the resistance of *Enterococcus* spp. to vancomycin [Gold H. S., Clin. Infect. Dis. 2001, 33: 210-219; Bonten M. J. et al. Lancet Infect. Dis. 2001, 1: 314-325].

These different bacterial species raise the problem of their detection in human pathological specimens and of their identification when isolated from such samples. Conventional detection methods rely on the evidencing of Gram-positive cocciform bacteria on direct examination of the pathological specimen. It is known, however, that this microscopic detection of bacteria of the genus *Streptococcus* and related genera in clinical specimens has a sensitivity threshold of $10^4$ CFU/ml. It is therefore fully possible that a pathological specimen in man or animal contains one of the species under consideration which is not detected by direct microscopic examination of this pathological specimen. In addition, even though their structure is of Gram-positive bacterial type, they may give a false Gram-negative result after Gram staining of the pathological sample and give rise to erroneous or inconclusive identification. This is particularly frequent in bacteria of genus *Gemella*. In man, this is especially the case in anatomopathological and bacteriological investigation of the heart valves when diagnosing endocarditis.

When a bacterium of one of the species of the genera under consideration is isolated in the laboratory, conventional phenotype identification methods are the most commonly used to identify bacteria of species belonging to genus *Streptococcus* and related genera, and several identification kits and automated analysers have been developed to assist phenotype identification of bacteria of genus *Streptococcus* and related genera. In this respect, the extent of identification in routine practice is variable. In particular, one of the tests used for identifying Streptococci and bacteria of related genera is the detection of a haemolytic reaction, i.e. the destruction by the bacterium of red blood cells contained in a blood agar. However, this haemolytic reaction can be inhibited by the presence of oxygen or by the presence of a peroxide when Streptococci bacteria are cultured in the presence of a high carbon dioxide concentration. Moreover, it is recognized that there exists a certain extent of subjectivity in assessing haemolysis by colonies of Streptococci and hence inter-operator variability which is detrimental to the quality of identification of these bacteria. For alpha-haemolytic streptococci, a second test is the optochin sensitivity test which enables identification of *Streptococcus pneumoniae* which is sensitive to this compound. However, strains of *Streptococcus pneumoniae* resistant to optochin have been reported [Lund E. Acta Patho. Microbiol. Immunol. Scand. 1959, 47, 308-315]. A final phenotype test is serotyping, which may also give false positive results in particular for streptococci in serogroup D on account of cross antigenicity between group D streptococci, *Enterococcus* and *Pediococcus*.

Several molecular systems have been developed to identify some serogroups or some species of genus *Streptococcus*, in particular for group A streptococci (*Streptococcus pyogenes, Streptococcus aginosus, Streptococcus constellatus, Streptococcus intermedius*) and group B (*Streptococcus agalactiae*) [Daly J. A. et al. J. Clin. Microbiol. 1991, 29:80-82; Heelan J. S. et al., Diagn. Microbiol. Infect. Dis. 1996, 24: 65-69] and for *Streptococcus pneumoniae* [Denys G. A. & Carrey R. B., J. Clin. Microbiol. 1992, 30: 2725-2727] by hybridisation of specific probes targeting the gene encoding the 16S ribosomal RNA. Also, different systems based on PCR amplification of genes coding for toxins or virulence factors have been developed to discriminate *Streptococcus pneumoniae* from among α-haemolytic Streptococci [Salo P. et al., J. Infect. Dis. 1995, 171: 479-482; Morrisson K. et al. J. Clin. Microbiol. 2000, 38, 434-437; Kaijalainen T. et al. J. Microbiol. Meth. 2002, 51: 111-118], and for the detection of *Streptococcus agalactiae* [Mawn J. A. et al. J. Clin. Pathol. 1993, 46: 633-636]. These different systems, however, only allow the identification of one or of a few species of genus *Streptococcus*.

An identification system for three species of *streptococcus* has been developed, based on amplification of the 16S-23S spacer [Forstman P. et al. Microbiology, 1997, 143, 3491-3500] but in this work identification was limited to only a few species of animal interest: *Streptococcus agalactiae, Streptococcus dysgalactiae* and *Streptococcus uberis*. Also, at the present time it is essential for laboratories to have 2 separate molecular targets for the detection and identification of streptococci to overcome the risks of molecular contamination inherent in the use of a single target.

Finally, no detection and identification system for *Streptococcus*-related genera has been developed, and more particularly for bacteria of the genera *Enterococcus, Gemella, Abiotrophia* and *Granulicatella*.

The inventors have shown in the present invention that the rpoB gene forms a genetic marker which can be used for the detection and specific identification of the bacterium of each species in genus *Streptococcus* and in 4 related genera: *Enterococcus, Gemella, Abiotrophia* and *Granulicatella*.

Although this gene has previously been shown to have use as a tool in bacterial identification of different bacterial genera, no publication mentions its use for identifying bacteria of genus *Streptococcus* and the four related genera, and the advantage of this gene's sequence for the identification of the said bacteria has in no way been suggested. On the contrary, a few partial sequences of the rpoB gene in a few species, available in GenBank, showed slight heterogeneity placing in doubt the advantage of this gene as an identification tool for these bacteria. Finally, the inventors have developed a tool for the simultaneous identification of four bacterial genera, requiring the development of degenerate primers which could not be deduced from any of the rpoB sequences determined for each species.

More particularly, the present invention concerns nucleic acid sequences specific to the genus or to each species of genus *Streptococcus* and related genera whose nucleotide sequence is derived from the rpoB gene of the said bacteria.

According to Lazcano et al. [J. Mol. Evol. (1988) 27: 365-376] the polymerase RNAs are divided into two groups as per their origin, one consisting of the RNA- or DNA-dependent viral polymerase RNAs and the other consisting of the DNA-dependent polymerase RNAs of eukaryote or prokaryote origin (archaebacteria and eubacteria). The eubacterial DNA-dependent polymerase RNAs are characterized by a simple, conserved multimeric constitution denoted "core enzyme" represented by $\alpha\beta\beta'$, or "holoenzyme" represented by $\alpha\beta\beta'\sigma$ [Yura and Ishihama, Ann. Rev. Genet. (1979) 13: 59-57].

Numerous studies have evidenced the functional role, within the multimeric enzymatic complex, of the $\beta$ subunit of the eubacterial polymerase RNA. Archaebacterial and eukaryote polymerase RNAs have a more complex structure possibly reaching ten and even thirty subunits [Pühlet et al. Proc. Natl. Acad. Sci. USA (1989) 86: 4569-4573].

The genes encoding the different $\alpha\beta\beta'\sigma$ (subunits of the DNA-dependent polymerase RNA in eubacteria, the genes rpoA, rpoB, rpoC and rpoD respectively, are classified in different groups comprising the genes coding for constituent proteins of the ribosomal subunits or for enzymes involved in the replication and repair of the genome [Yura and Yshihma, Ann. Rev. Genet. (1979) 13: 59-97]. Some authors have shown that the sequences of the rpoB and rpoC genes could be used to construct phylogenetic trees [Rowland et al. Biochem. Soc. Trans. (1992) 21:40S] enabling separation of the different branches and sub-branches among the kingdoms of the living.

Before setting forth the invention in more detail, different terms used in the description and claims are defined below:

By "nucleic acid extracted from bacteria" is meant either the total nucleic acid, or the genomic DNA, or the messenger RNAs, or the DNA obtained from reverse transcription of the messenger RNAs.

A "nucleotide fragment" or an "oligonucleotide" are two synonymous terms designating a chain of nucleotide motifs characterized by an information sequence of the natural (or optionally modified) nucleic acids and able to hybridise, like natural nucleic acids, with a complementary or substantially complementary nucleotide fragment under predetermined conditions of high stringency. The chain may contain nucleotide motifs having a different structure to natural nucleic acids. A nucleotide fragment (or oligonucleotide) may for example contain up to 100 nucleotide motifs. It generally contains at least 8, and in particular at least 12 nucleotide motifs, further particularly 18 to 35, and may be obtained from a natural nucleic acid molecule and/or by genetic recombination and/or by chemical synthesis.

A nucleotide motif is derived from a monomer which may be a natural nucleotide of a nucleic acid whose constituent elements are a sugar, a phosphate group and a nitrogenous base chosen from among adenine (A), guanine (G), uracil (U), cytosine (C), thymine (T); or else the monomer is a nucleotide modified in at least one of the three preceding constituent elements; as an example, modification may occur either at the bases, with modified bases such as inosine which can hybridise with any base A, T, U, C or G, methyl-5-deoxycytidine, deoxyuridine, dimethylamino-5-deoxyuridine or any other modified base able to hybridise, or at the sugar, for example the replacement of at least one deoxyribose by a polyamide (Nielsen P E et al., Science (1991) 254: 1497-1500], or at the phosphate group, for example through replacement by esters chosen from among diphosphates, alkylphosphonates and phosphorothioates.

By "hybridisation" is meant the process during which, under suitable conditions, two nucleotide fragments having sufficiently complementary sequences are able to join together by stable, specific hydrogen bonds to form a double strand. Hybridisation conditions are determined by "stringency" i.e. the strictness of operating conditions. Hybridisation is more specific the higher the stringency. Stringency depends in particular upon the base composition of a probe/target duplex and on the extent of mismatch between two nucleic acids. Stringency may also be related to parameters of the hybridisation reaction, such as the concentration and type of ion species present in the hybridisation solution, the type and concentration of denaturing agents and/or the temperature of hybridisation. The stringency of the conditions in which a hybridisation reaction must be conducted depends in particular upon the probes used. All this data is well known and the suitable conditions may possibly be determined in each case by routine experiments. In general, depending upon the length of the probes used, the temperature for the hybridisation reaction lies between approximately 20 and 65° C., in particular between 35 and 65° C. in a saline solution at a concentration of around 0.8 to 1 M.

A "probe" is a nucleotide fragment having hybridisation specificity under determined conditions to form a hybridisation complex with a nucleic acid having, in this case, a nucleotide sequence included either in a messenger RNA or in a DNA obtained by reverse transcription of said messenger RNA, the transcription product; a probe may be used for diagnosis purposes (capture and detection probes in particular) or for therapeutic purposes.

A "capture probe" is a probe that is or may be immobilised on a solid support by any appropriate means, for example by covalency, adsorption, or direct synthesis on a solid. Examples of supports include microtitration wafers and DNA chips.

A "detection probe" is a probe labelled with a marking agent chosen for example from among radioactive isotopes, enzymes in particular enzymes able to act on a chromogenous, fluorigenous or luminescent substrate (in particular a peroxidase or an alkaline phosphatase), chromophorous chemical compounds, chromogenous, fluorigenous or luminescent compounds, analogues of nucleotide bases and ligands such as biotin.

A "species probe" is a probe enabling the specific identification of the species of a bacterium.

A "genus probe" is a probe enabling the specific identification of the genus of a bacterium.

A "primer" is a probe having 10 to 100 nucleotide motifs for example and having hybridisation specificity under determined conditions for enzymatic amplification reactions.

By "amplification reaction" is meant an enzymatic polymerisation reaction, for example in an amplification technique such as PCR, initiated by primer oligonucleotides and using a polymerase DNA.

By "sequencing reaction" is meant the obtaining of the sequence of a nucleic acid fragment or of a complete gene by means of an abortive polymerisation method using oligonucleotide primers and said dideoxynucleotides [Sanger F, Coulson A R (1975), J. Mol. Biol. 94: 441] or multiple hybridisations with multiple probes fixed on a solid support such as used in DNA chips for example.

The sequences of the rpoB genes of the bacteria *Streptococcus pneumoniae, Streptococcus pyogenes, Streptococcus mutans* and *Streptococcus agalactiae* have been described in the literature.

The inventors have determined the complete sequences of the rpoB genes of other bacterial species of genus *Streptococcus* and related genera: *Streptococcus anginosus* and *Streptococcus equinus, Abiotrophia defectiva*, and a very large portion of the gene for *Streptococcus mutans* and *Enterococcus faecalis*. These species were chosen by the inventors as representing the main genetic groups determined on the basis of the study on the 16S gene in bacteria of genus *Streptococcus* and related genera, encompassing all the species currently described in this genus, so that the alignment of the rpoB sequences obtained in these species would most probably encompass all the rpoB sequences of all the species of these bacterial genera, more precisely they are therefore the most divergent species from a phylogenetic viewpoint among all the species currently described in this genus, so that the alignment of the rpoB sequences obtained in these species would most probably from a phylogenetic viewpoint encompass all the rpoB sequences of all the species of this bacterial genus.

From these complete or almost complete sequences, and after numerous unsuccessful attempts such as reported in examples 1 and 2 below, the inventors have evidenced the following consensus and specific sequences SEQ ID no 6 and 7:

```
SEQ ID N° 6:    5'-AARYTNGGMCCTGAAGAAAT-3',
and

SEQ ID N° 7:    5'-TGNARTTTRTCATCAACCATGTG-3'
``` in which:
N represents inosine or one of the 4 nucleotides A, T, C or G,
R represents A or G,
M represents A or C, and
Y represents C or T, and the reverse sequences and complementary sequences.

The inventors have determined said sequences SEQ ID no 6 and 7 as being not only consensual between all the bacteria of genus *Streptococcus* and said 4 related genera, but also specific to the family of bacteria of genus *Streptococcus* and said 4 related genera.

At the position corresponding to a nucleotide N, Y, M or R in sequences SEQ ID no 6 and 7, variable nucleotides are found in the complementary target sequences in relation to the species of the bacterium under consideration, but all the other nucleotides are conserved in all the species of bacteria of genus *Streptococcus* and of said 4 related genera.

Sequences SEQ ID no 6 and 7 so defined are present in the rpoB genes of all bacteria of genus *Streptococcus* and said 4 related genera, and are specific to the bacteria of genus *Streptococcus* and said 4 related genera, and can therefore provide genus probes or amplification primers to detect any bacterium of genus *Streptococcus* and of said 4 related genera.

For this purpose, one subject of the present invention is therefore an oligonucleotide which comprises a sequence of at least 8, preferably at least 12, further preferably between 18 and 35 nucleotide motifs, of which at least one sequence of 8, preferably 12, further preferably 18 consecutive motifs is included in one of the following sequences SEQ ID no 6 and 7:

```
SEQ ID N° 6:    5'-AARYTNGGMCCTGAAGAAAT-3',
and

SEQ ID N° 7:    5'-TGNARTTTRTCATCAACCATGTG-3'
``` in which:
N represents inosine or one of the 4 nucleotides A, T, C or G,
R represents A or G,
M represents A or C, and
Y represents C or T and the reverse sequences and complementary sequences.

Another subject of the invention is a mixture of oligonucleotides characterized in that it consists of an equimolar mixture of oligonucleotides of the invention, all having a different sequence and all comprising a sequence included in SEQ ID no 6 or all comprising a sequence included in SEQ ID no 7.

More particularly, a further subject of the invention is a mixture of said oligonucleotides, consisting of an equimolar mixture of 32 oligonucleotides of different sequences each comprising at least 15, preferably at least 18 consecutive nucleotide motifs included in the following sequence:

```
SEQ ID n° 6:    5' AARYTNGGMCCTGAAGAAAT-3'
``` in which:
R represents A or G,
Y represents C or T
M represents A or C, and
N represents A, T, C or G and the reverse sequences and complementary sequences.

A further subject of the invention is a mixture of said oligonucleotides consisting of an equimolar mixture of 8 oligonucleotides having different sequences and each comprising at least 15, preferably at least 18 consecutive nucleotide motifs included in the following sequence:

SEQ ID n° 6:       5' AARYTNGGMCCTGAAGAAAT-3' in which:
R represents A or G,
Y represents C or T
M represents A or C, and
N represents inosine and the reverse sequences and complementary sequences.

A further subject of the invention is a mixture of said oligonucleotides, consisting of an equimolar mixture of 16 oligonucleotides having different sequences and each comprising at least 15, preferably at least 21 consecutive nucleotide motifs included in the following sequence:

SEQ ID n° 7:       5' TGNARTTTRTCATCAACCATGTG-3' in which:
R represents A or G, and
N represents A, T, C or G and the reverse sequences and complementary sequences.

A further subject of the present invention is a mixture of said oligonucleotides, consisting of an equimolar mixture of 4 oligonucleotides having different sequences and each comprising at least 15, preferably at least 21 consecutive nucleotide motifs included in the following sequence:

SEQ ID n° 7:       5'-TGNARTTTRTCATCAACCATGTG-3' in which:
R represents A or G, and
N represents inosine, and the reverse sequences and complementary sequences.

Said mixtures of oligonucleotides are able to hybridise with a complementary sequence included in the rpoB gene of all the bacteria of genus *Streptococcus* and said 4 related genera, and can therefore be used as a genus probe or as amplification primers for the detection or respectively the amplification of an rpoB gene fragment of said bacterium.

To prepare said equimolar mixture of oligonucleotides using oligonucleotide synthesis methods known to persons skilled in the art, an equimolar mixture is used of 4 or 2 nucleotides for the nucleotides corresponding to N or respectively K, N, R or Y, namely:
- an equimolar mixture of the 4 nucleotides A, T, C and G for the nucleotides corresponding to N in which N represents A, T, C or G, and
- an equimolar mixture of the 2 nucleotides T and G for the nucleotides corresponding to K,
- an equimolar mixture of the 2 nucleotides A and C for the nucleotides corresponding to N,
- an equimolar mixture of the 2 nucleotides A and G for the nucleotides corresponding to R, and
- an equimolar mixture of the 2 nucleotides C and T for a nucleotide represented by Y.

Hence an equimolar mixture is obtained of 32 ($2^3 \times 4$) and 16($2^2 \times 4$) nucleotides of different sequences for the 2 sequences SEQ ID no 6 and 7 respectively.

In said equimolar mixtures of oligonucleotides according to the invention, since "N" represents inosine which is able to hybridise with any base or an equimolar mixture of the 4 bases A, T, C, G, the sequences SEQ ID no 6 and 7 are able to hybridise with the complementary sequence included in the rpoB gene of all bacteria of the *Streptococcus* genus and of the said 4 related genera.

In addition, these consensus sequences SEQ ID no 6 and no 7 flank hyper-variable sequences whose sequence is specific to each bacterium species of genus *Streptococcus*. These sequences flanked by SEQ ID no 6 and 7 may therefore be used as species probe for the bacteria of genus *Streptococcus* and said 4 related genera.

In addition, the sequences SEQ ID no 6 and 7 were determined as flanking an rpoB gene fragment comprising a zone whose variable length is approximately 720 bp and as comprising the shortest sequences specific to each bacterium species of the *Streptococcus* genus and said 4 related genera.

The inventors were therefore able to evidence species probes for each of the examined 28 bacterial species of genus *Streptococcus* and said 4 related genera, corresponding to sequences SEQ ID no 8 to 35 described in example 2 below, flanked by the consensus sequences SEQ ID no 6 and 7.

A further subject of the present invention is a rpob gene or gene fragment of a bacterium of genus *Streptococcus* or of one of said 4 related genera, except sequences SEQ ID no 11, 12, 14, and of the bacteria *Streptococcus pyogenes, Streptococcus pneumoniae, Streptococcus mutans* and *Streptococcus agalactiae*, the reverse sequences and complementary sequences, characterized in that it comprises a sequence such as described in sequences SEQ ID no 8 to 35 described in example 2.

A further subject of the invention is the complete sequence of the rpob gene of the bacteria *Streptococcus anginosus, Streptococcus equinus* and *Abiotrophia defectiva* such as described in sequences SEQ ID no 1 to 3, which can be used in particular for a method of the invention.

A further subject of the present invention is the almost complete sequence of the rpob gene of the bacterium *Enterococcus faecalis* such as described in SEQ ID no 5, which can be used in particular for a method of the invention.

In sequences SEQ ID no 1 to 3 and 5 and 8 to 35 described in the sequence listing at the end of the description:
nucleotide M represents A or C,
nucleotide K represents T or G,
nucleotide R represents A or G,
nucleotide W represents A or T,
nucleotide Y represents C or T,
nucleotide N represents A, T, C, G or I
nucleotide S represents C or G,
nucleotide V represents A, C or G The consensus sequences derived from SEQ ID no 6 and 7 evidenced according to the present invention, may be used as genus probe, as amplification or sequencing reaction primer in detection methods for bacteria of genus *Streptococcus* and said 4 related genera, by molecular identification.

With the sequences derived from sequences SEQ. ID no 6 and 7 it is therefore not only possible to prepare genus probes for bacteria of genus *Streptococcus* and said 4 related genera, but also to detect and identify the species of said bacteria through amplification and sequencing using said sequences as primers.

The complete sequence of the rpoB gene may be used to identify the bacterium not only through the study of its primary sequence, but also through the study of the secondary and tertiary structures of the messenger RNA derived from transcription of the complete DNA sequence.

A further subject of the invention is an oligonucleotide or an rpoB gene fragment having a sequence included in or consisting of sequences SEQ ID no 8 to 35, hence including sequences SEQ ID no 11, 12, 14 and 22 of the bacteria *Streptococcus pyogenes, Streptococcus pneumoniae, Streptococcus mutans* and *Streptococcus agalactiae* respectively, and also among the oligonucleotides or fragments of reverse or complementary sequences such as defined above.

The inventors, after analysing the different sequences and comparing pair by pair all sequences SEQ. ID no 8 to 35, determined that the homology rate between two different sequences among said sequences SEQ ID no 8 to 35 is a maximum rate 99.3%. Below 99.3% homology between the sequences, they identify bacteria of different species. Consequently, a further subject of the invention is oligonucleotides or rpoB gene fragments having sequences included in or consisting of said sequences SEQ ID no 8 to 35, the reverse sequences, the complementary sequences and sequences showing at least 99.3% homology (i.e. a similarity rate of at least 99.3% between the sequences) with respect to said sequences SEQ ID no 8 to 35, the reverse sequences and complementary sequences respectively.

The oligonucleotides, gene fragments and genes subject of the present invention have been described as comprising DNA sequences i.e. with nucleotides A, T, C and G. However, a further subject of the present invention is oligonucleotides comprising corresponding RNA sequences, i.e. in which T is replaced by U.

In the present description, by "reverse sequences and complementary sequences" is meant the following sequences:
the reverse sequence of said sequence,
the complementary sequence of said sequence, and
the complementary sequence of the reverse sequence of said sequence.

Sequences SEQ ID no 1 to 35 may be prepared by genetic engineering and/or chemical synthesis, in particular by automatic synthesis, using techniques well known to persons skilled in the art.

One first application of an oligonucleotide of the invention is its use a probe for the detection, in a biological specimen, of bacteria of one of the species of genus *Streptococcus* and said 4 related genera, which comprises a nucleotide sequence in one of the sequences SEQ ID no 6 to 35 and their reverse or complementary sequences.

An oligonucleotide comprising sequences SEQ ID no 6 and 7 will be used as genus probe, and an oligonucleotide comprising a sequence included in or comprising one of sequences SEQ ID no 8 to 35 will be used as species probe.

More particularly, the subject of the present invention is an oligonucleotide comprising a sequence specific to a bacterium species of genus *Streptococcus* and said related genera, preferably having at least 20 consecutive nucleotides, further preferably at least 30 consecutive nucleotides included in one of said sequences SEQ ID no 8 to 35, or optionally an equimolar mixture of said oligonucleotides having different sequences.

Preferably, said sequences included in one of sequences SEQ ID no 8 to 35, preferably having at least 20, further preferably at least 30 consecutive nucleotides included in one of said sequences SEQ ID no 8 to 35, form the shortest sequences specific to the different respective species which can be used as species probe for *Streptococcus* bacteria and for said 4 related genera under consideration.

The probes of the invention may be used for diagnostic purposes, as mentioned previously, by determining the formation or non-formation of a hybridisation complex between the probe and a target nucleic acid in the specimen, using all known hybridisation techniques in particular "DOT-BLOT" techniques [Maniatis et al. (1982) Molecular Cloning, Cold Spring Harbor] DNA transfer techniques called "SOUTHERN BLOT" [Southern E. M., J. Mol. Biol. (1975) 98: 503], RNA transfer techniques called "NORTHERN BLOT", or so-called "sandwich" techniques in particular using a capture probe and/or a detection probe, said probes being able to hybridise with two different regions of the target nucleic acid, and at least one of said probes (generally the detection probe) being able to hybridise with a target region that is specific to the species, the capture probe and the detection probe evidently having nucleotide sequences that are at least partly different.

The nucleic acid to be detected (target) may be DNA or RNA (the first obtained after PCR amplification). When detecting a target of double strand nucleic acid type, the latter must first be denatured before starting detection. The target nucleic acid may be obtained using known methods for its extraction from a specimen to be examined. Denaturing of a double strand nucleic acid may be conducted using known chemical, physical or enzymatic methods, in particular by heating to an appropriate temperature, of over 80° C.

To implement the above-mentioned hybridisation techniques, in particular the "sandwich" techniques, a probe of the invention called a capture probe is immobilised on a solid support, and another probe of the invention called a detection probe is labelled with a marking agent. Examples of supports and marking agents are those previously given.

Advantageously, a species probe is immobilised on a solid support, and another species probe is labelled with a marking agent.

Another application of an oligonucleotide of the invention is its use as nucleotide primer comprising a monocatenary oligonucleotide chosen from among oligonucleotides having a sequence of at least 12 nucleotide motifs included in one of sequences SEQ ID no 6 to 35, which can be used in the synthesis of a nucleic acid in the presence of a polymerase using a known method, in particular by amplification methods using said synthesis in the presence of a polymerase (PCR, RT-PCR, etc). In particular, a primer of the invention may be used for the specific reverse transcription of a messenger RNA sequence of a bacterial species of genus *Streptococcus* and said 4 related genera to obtain a corresponding complementary DNA sequence. Said reverse transcription may form the first stage of the RT-PCR technique, the following stage being PCR amplification of the complementary DNA obtained. Primers of the invention may also be used for specific amplification, by chain polymerisation reaction, of the total DNA sequence of the rpoB gene of a species of genus *Streptococcus* and said 4 related genera.

In one particular case, said primer comprising an oligonucleotide of the invention also comprises the sense or antisense sequence of a promoter recognized by a polymerase RNA (promoters T7, T3, SP6 for example [Studier F W, B A Moffatt (1986) J. Mol. Biol. 189:113]: said primers can be used in nucleic acid amplification methods using a transcription step such as, for example, NASBA or 3SR techniques [Van Gemen B et al. Abstract MA 1091, 7th International Conference on AIDS (1991) Florence, Italy].

A further subject of the invention is a nucleotide primer comprising an oligonucleotide chosen from among oligonucleotides having a sequence comprising one of sequences SEQ ID no 6 to 35 or a sequence included in SEQ ID no 6 to 35 which can be used for full or partial sequencing of the rpoB gene of any strain of a bacterial species of genus *Streptococcus* and said 4 related genera.

Full or partial sequencing of the rpoB gene in any bacterium of genus *Streptococcus* and related genera enables the identification of all bacteria of genus *Streptococcus* and of said 4 related genera by bio-computerized analysis of this sequence, and enables the recognition of new unknown bacterial species of *Streptococcus* and of said 4 related bacteria.

Preferably, for use as a primer or for sequencing rpoB genes, said mixture of oligonucleotides of the invention is used, and further preferably said mixtures of oligonucleotides consisting of sequences SEQ ID no 6 and SEQ ID no 7.

More precisely, the present invention provides a detection method by identification to detect a bacterium of one of the species of genus *Streptococcus* and of said 4 related genera, characterized in that the following are used:

- a complete or almost complete rpoB gene of said bacterium according to the present invention and an rpoB gene or gene fragment of a bacterium *Streptococcus pyogenes*, *Streptococcus pneumoniae*, *Streptococcus mutans* and *Streptococcus agalactiae* comprising a sequence such as described in sequences SEQ ID no 11, 12, 14 and 22 respectively, the reverse sequences and complementary sequences, which may be used in particular as species probe, and/or
- a said fragment of said rpoB gene of said bacterium according to the present invention, comprising a nucleotide sequence chosen from among one of sequences SEQ ID no 8 to 35, the reverse sequences and complementary sequences, which may be used in particular as species probe, and/or
- an oligonucleotide of the present invention comprising a sequence included in one of sequences SEQ ID no 8 to 35, the reverse sequences and complementary sequences, which may be used in particular as species probe, and/or
- an oligonucloetide or said mixture of oligonucleotides of the present invention comprising a sequence consisting of consecutive nucleotide motifs, included in one of sequences SEQ ID no 6 and 7, which may be used in particular as genus probe or amplification primer.

Preferably, in said detection method of the invention, the following are used:

- a said rpoB gene fragment of said bacterium comprising a sequence chosen from among one of sequences SEQ ID no 8 to 35 or an oligonucleotide having a sequence included in one of said sequences SEQ ID no 8 to 35, the reverse sequences and complementary sequences, and/or
- at least one said mixture of oligonucleotides according to the present invention whose preferable sequences consist of sequences SEQ ID no 6 and 7, and their reverse sequences and complementary sequences in which further preferably N represents inosine.

In a first embodiment of a detection method of the invention, it is sought to evidence the presence of a bacterium of genus *Streptococcus* and said 4 related genera, and the following steps are performed in which:

1. at least one genus probe comprising a said mixture of oligonucleotides having sequences comprising or included in one of sequences SEQ ID no 6 and 7, the reverse sequences and complementary sequences according to the invention, is contacted with a specimen containing or possibly containing nucleic acids of at least one said bacterium of genus *Streptococcus* and of said 4 related genera, and
2. the formation or non-formation is determined of a hybridisation complex between said genus probe and the nucleic acids of the specimen, and the presence is determined of said bacterium of genus *Streptococcus* or of said 4 related genera if a hybridisation complex is formed.

In a second embodiment of a detection method for a bacterium of genus *Streptococcus* and said 4 related genera, the steps are performed in which:

1. Amplification primers, comprising said mixtures of oligonucleotides containing a sequence included in said sequences SEQ ID no 6 and 7 reverse sequences and complementary sequences of the invention, are contacted with a sample containing or possibly containing nucleic acids of at least one said bacterium of genus *Streptococcus* and of said 4 related genera, using:
   - as 5' primer: a said mixture of oligonucleotides containing a sequence included in sequence SEQ ID no 6 or preferably consisting of said complete sequence SEQ ID no 6, or a complementary sequence of the invention,
   - as 3' primer: a said mixture of oligonucleotides containing a sequence included in sequence SEQ ID no 7 or preferably consisting of said complete sequence SEQ ID no 7, or respectively a complementary sequence of the invention.
2. The nucleic acids are amplified by enzymatic polymerisation reaction, and the occurrence or non-occurrence of an amplification product is determined, and in this way the presence is determined of said bacterium in the specimen if an amplification product is produced.

This second embodiment may be used to specifically detect the genus of a *Streptococcus* bacterium or said 4 related genera.

However, at step 2 of this second embodiment, it may be sought to specifically detect a given bacterium species of genus *Streptococcus* chosen from among the species *Streptococcus mutans, Streptococcus oralis, Streptococcus pneumoniae, Streptococcus pyogenes, Streptococcus salivarius, Streptococcus sanguinis, Streptococcus suis, Streptococcus acidominimus, Streptococcus agalactiae, Streptococcus anginosus, Streptococcus constellatus, Streptococcus difficilis, Streptococcus dysgalactiae, Streptococcus equi, Streptococcus equinus, Streptococcus intermedius, Streptococcus mitis, Streptococcus bovis, Granulicatella adjacens, Abiotrophia defectiva, Enterococcus avium, Enterococcus casseliflavus, Enterococcus faecalis, Enterococcus faecium, Enterococcus gallinarum, Enterococcus sacharolyticus, Gemella haemolysins* and *Gemella morbillorum*, as described in the variant of embodiment of a detection method specific to a species of said bacteria, given in the description below.

As previously set forth in the introduction, the genera *Streptococcus, Enterococcus, Granulicatella, Abiotrophia* and *Gemella* comprise more bacterial species than those effectively sequenced in this work. However, the sequenced species were chosen so that they encompass all known species in these bacterial genera and are sufficient in number to demonstrate the application of the rpoB sequence to the identification of the species of these genera.

In a variant of embodiment of a method of the invention for specifically detecting a species of said bacteria, the steps are performed in which:

1. a specimen containing or possibly containing nucleic acids of at least one said bacterium is contacted with at least one species probe consisting of said gene, said gene fragment or said oligonucleotide containing a sequence included in one of sequences SEQ ID no 8 to 35, preferably an oligonucleotide consisting of one of said sequences SEQ ID no 8 to 35, the reverse sequences and complementary sequences according to the invention, and 2. the formation or non-formation of a hybridisation complex is determined between said probe and the nucleic acids in the specimen, thereby determining the presence of said bacterium in the specimen if a hybridisation complex is formed.

In another variant of embodiment of the method of the invention, in which it is sought to specifically detect a given species of a bacterium of genus *Streptococcus* and of said 4 related genera, chosen from among the 28 species cited above, the method comprises the steps in which, in a specimen containing or possibly containing nucleic acids of at least one said bacterium:

a) a sequencing reaction is conducted of an amplified rpoB gene fragment of said given bacterium using nucleotide primers consisting of said mixtures of oligonucleotides containing sequences included in sequence SEQ ID no 6 as 5' primer, and in SEQ ID no 7 as 3' primer, the sequences preferably consisting of said sequences SEQ ID no 6 and 7, and their complementary sequences, and b) the presence or absence of the given species of said bacterium is determined by comparing the obtained sequence of said fragment with the sequence of the complete rpoB gene of said bacterium or the sequence of a rpoB gene fragment of said bacterium containing said sequences no 8 to 35 and complementary sequences of the invention, thereby determining the presence of said bacterium in the specimen if the obtained fragment sequence is identical to the known sequence of the genus or of the rpoB gene fragment of said bacterium.

A further subject of the present invention is a diagnosis kit which can be used for a method of the invention, containing at least one said gene fragment or said oligonucleotide having a sequence included in or consisting of sequences SEQ ID no 8 to 35, or a said oligonucleotide or mixture of oligonucleotides containing a sequence included in one of sequences SEQ ID no 6 and 7, and/or at least one said rpoB gene fragment of said bacterium comprising sequences SEQ ID no 8 to 35 and complementary sequences of the invention.

Advantageously, a kit of the present invention contains said oligonucleotides in the form of "biochips", i.e. fixed to solid supports, glass in particular, according to the method described in U.S. Pat. No. 5,744,305 (Affymetrix, Fodor et al) using the resequencing strategy described in application WO 95/11995 (Affymax, Chee et al) or according to the method described by A. Troesch et al. in J. Clin. Microbiol., vol. 37(1), p 49-55, 1999. The oligonucleotides synthesized on the "biochip" carry out re-sequencing of the hyper variable region of the rpoB gene. This method offers considerable advantage in terms of production costs with no detriment to quality of identification of the different species through the choice of these identification sequences. Preferably, these oligonucleotides fixed onto the "biochip" solid support comprise 10 to 30 bases, e.g. 20 bases, with an interrogation position located in the central region for example at position 12 with respect to the 3' end of the sequence for oligonucleotides with 20 bases. Another example consists of using oligonucleotides having 17 bases with 2 interrogation positions: one at position 10 and one at position 8. Other oligonucleotides have lengths of between 10 and 25 nucleotides. The interrogation positions then vary according to the length of the oligonucleotide.

Analysis is conducted on the complete GeneChip® system (reference 900228, Affymetrix, Santa Clara, Calif.) which comprises the GeneArray® reader, the GeneChip® hybridisation oven, GeneChip® fluid station and GeneChip® analysis software.

An oligonucleotide of the invention may also be used as a gene therapy probe to treat infections caused by a strain belonging to a species of genus *Streptococcus* and said 4 related genera, said probe comprising an oligonucleotide such as defined previously. This gene therapy probe, able to hybridise on the messenger RNA and/or on the genomic DNA of said bacteria, may block translation and/or transcription and/or replication phenomena.

The principle of gene therapy methods is known and is based in particular on the use of a probe corresponding to an antisense strand: the formation of a hybrid between the probe and the sense strand is able to disrupt at least one of the genetic information decoding steps. Gene therapy probes can therefore be used as anti-bacterial medicines, making it possible to fight against infections caused by bacteria belonging to the species of genus *Streptococcus* and said 4 related genera.

The invention will be more readily understood with the help of the description given below, divided into examples relating to experiments conducted with a view to implementing the invention and which are given solely for illustrative purposes.

FIG. 1 shows the visualisation of the amplification products through ethidium bromide staining after electrophoresis on an agarose gel obtained in example 3.

EXAMPLE 1

Sequence of the rpoB Gene of Three Species of Genus *Streptococcus* and Related Genera: *Abiotrophia defectiva*, *Streptococcus anginosus* and *Streptococcus equinus*

The complete sequence of the rpoB gene of bacteria belonging to the species of *Abiotrophia defectiva*, *Streptococcus anginosus* and *Streptococcus equinus* was determined by enzymatic amplification and automatic sequencing available for Streptococci. The choice of these species was based on analysis of the 16S tree which shows genetic divergence covering the entire phylogenetic tree for streptococci.

Strategy and Sequencing:

Several partial 510-bp sequences of rpoB genes are available from GenBank for the 10 following *streptococcus* species: *Streptococcus intermedius*, *Streptococcus sanguinis*, *Streptococcus penumoniae*, *Streptococcus parasanguinis*, *Streptococcus oralis*, *Streptococcus mitis*, *Streptococcus cristalus*, *Streptococcus constellatus*, *Streptococcus anginosus*, and *Granulicatell adjacens* [Majewski J., Zawadzki P., Pickerill P., Cohan F. M. and Dowson C. G. Barriers to genetic exchange between bacterial species: *Streptococcus pneumoniae* transformation. J. Bacteriol. 182, 1016-1023 (2000)], but the primers used by these authors only amplify a fraction of the species of genus *Streptococcus*, and it was therefore not possible to carry out our work on the basis of this data alone. It was therefore necessary to determine primers able to amplify all strains of streptococci, enterococci, *Abiotrophia*, *Gemella* and *Granulicatella*. These primers also had to flank a region showing sufficient genetic diversity so as to be able to distinguish between two species. However, the alignment of these published partial sequences made it possible to determine the following common primers: (the numbering refers to the complete sequence of *Streptococcus pyogenes*)

```
SEQ ID n° 36:  5'-AGACGGACCTTCTATGGAAAA-3'    (primer 748F)

SEQ ID n° 37:  5'-GGACACATACGACCATAGTG-3'    (primer 116R),
and

SEQ ID n° 38:  5'-GTTGTAACCTTCCCAWGTCAT -3'  (primer 830R).
```

These primers allowed the sequencing of the central part of the rpoB gene with 714 bp for the five chosen species (*Streptococcus equinus, Streptococcus mutans, Streptococcus anginosus, Enterococcus faecalis*, and *Abiotrophia defectiva*. From this central fragment, sequencing was continued using the so-called genome Walker technique.

Outside this published zone [Majewski J. et al, J. Bacteriol. 2002, 182, 1016-1023], the alignment of the two complete sequences available from GenBank (*Streptococcus pneumoniae* [GenBank access number AE008542] and *Streptococcus pyogenes* [GenBank access number AE006480] made it possible to choose the following primers:

for the sequencing of the end C- and N-zones by Genome Walker.

Sequencing was then complete as displayed by the determination of the encoding region and the alignment of the translated proteins of the nucleotide sequences with the two published rpoB proteins of *Streptococcus pneumoniae* and *Streptococcus pyogenes*.

Several potential consensus primers were investigated to obtain a fragment able to lead to the complete sequence of the rpoB genes by successive elongations from a series of specific primers.

In each of the above steps, a large number of attempts with theoretically or potentially suitable primers failed before the

```
SEQ ID n° 39:  5'-GTCTTCWTGGGYGATTTCCC-3'     (primer 2215R)

SEQ ID n° 40:  5'-ACCGTGCIGCWTGGTTRGAAT-3'    (primer 2057R)

SEQ ID n° 41:  5'-AACCAATTCCGYATYGGTYT-3'     (primer 1252R)

SEQ ID n° 42:  5'-AGIGGGTTTAACATGATGTC-3'     (primer 371F)

SEQ ID n° 43:  5'-AGIGCCCAAACCTCCATCTC-3'     (primer 730F),
and

SEQ ID n° 44:  5'-CTCCAAGTGAACAGATGTGTA-3'    (primer 585R)
```

With these primers, it was possible to extend the sequenced region for some of the five chosen strains. In fully unexpected manner, *E. Faecalis* is not amplified by these primers; but it was observed that the sequenced partial zone showed homology with the rpob gene of *Listeria monocytogenes*, i.e. with a bacterium belonging to a different bacterial genus which could in no way be inferred from existing data, and we therefore chose primers in the rpoB gene of *Listeria* to amplify the rpoB gene of *Enterococcus faecalis*.

above-mentioned primers were determined enabling the amplification and sequencing in successive steps of the entirety of the rpoB genes described below.

The sequencing reactions were conducted using reagents from the kit: ABI Prism dRhodamine Dye Terminator Cycle Sequencing Ready Reaction Kit (Perkin Elmer Applied Biosystems) in accordance with the manufacturer's recommendations and following the programme: 30 cycles comprising a denaturing step at 94° C. for 10 sec., a hybridisation step of

```
SEQ ID n° 45:  5'-TTACCAAACTTAATTGAGATTCAAAC-3'  (primer 180F)

SEQ ID n° 46:  5'-AGTATTTATGGGTGATTTCCCA-3'      (primer 410F)

SEQ ID n° 47:  5'-GGACGTTATAAAATCAACAAAAAATT-3'  (primer 910F)

SEQ ID n° 48:  5'-AGTTATAACCATCCCAAGTCATG-3'     (primer 2430R)

SEQ ID n° 49:  5'-TGAAGTTTATCATCAACCATGTG-3'     (primer 3280R)

SEQ ID n° 50:  5'-CCCAAAACGTTGTCCACC-3'          (primer 3360R)
```

The partial sequences so obtained for the five chosen strains (*Streptococus equinus, Streptococcus mutans, Streptcoccus anginosus, Enterococcus faecalis, Abiotrophia defectiva*) made it possible to choose the following primers:

the primer at 50° C. for 10 sec. and an extension step at 60° C. for 2 minutes. The sequencing products were separated by electrophoresis on a polyacrylamide gel and 377 DNA sequencer (Perkin) and analysed to form consensus

```
SEQ ID n° 51:  5'-AACCAAGCYCGGTTAGGRAT-3'      (primer 520R)

SEQ ID n° 52:  5'-ATGTTGAACCCACTIGCGGTGCCAT-3' (primer 2881F)
``` sequences using Sequence Assembler software (Applied Biosystems).

With this approach we were able to determine the complete sequence of the rpoB gene in two species of genus *Streptococcus* and in *Abiotrophia defectiva*:

SEQ ID no 1: Sequence of the rpoB gene of *Streptococcus anginosus*. This sequence measures 4523 base pairs, has a guanosine plus cytosine content of 41% and is deposited in GenBank under accession number AF 535183:

```
5'-TCATACTTTTAGAGTCAGATTTAGCTGCTCTTTTTGTGCCTGTTTTGGGATTTTTGTCGTTTGT
CATCAAAATTAAAGATTCTGAAAATTACTCAAAAAGGATAAATGAAAATTGCTACTCTATTCCA
TTAATAGACAATGTAGAAAGAAGAAGGAGTAAAAAACTTGGCAGGACATGAAGTTCAATACGGG
AAACACCGTACTCGTCGTAGTTTTTCAAGAATCAAGGAAGTTCTTGATTTACCAAATTTGATTG
AAATCCAGAGGATTCGTTCAAAGATTTTCTTGACCATGGTTTGAAAGAAGTATTTGAAGATGTA
CTTCCTATCTCAAACTTTACAGATACAATGGAGCTAGAGTTTGTTGGTTATGAAATTAAAGGAT
CTAAATACACTTTAGAAGAAGCACGTATCCATGATGCCAGCTATTCTGCACCTATTTTTGTGAC
TTTCCGTTTGATTAATAAAGAAACTGGTGAAATCAAAACCCAAGAAGTGTTCTTTGGCGATTTC
CCAATCATGACAGAAATGGGAACTTTCATTATCAATGGTGGTGAGCGGATTATCGTATCTCAGC
TCGTTCGTTCTCCAGGTGTTTACTTCAACGATAAAGTAGACAAAAATGGTAAAGTTGGTTATGG
TTCAACTGTCATTCCTAACCGTGGAGCTTGGTTAGAGCTGGAAACAGACTCAAAAGATATTGCT
TATACTCGGATTGACCGTACTCGTAAGATTCCGTTTACGACACTTGTTCGTGCGCTTGGTTTTT
CTGGCGATGATGAAATCTTTGACATTTTCGGCGACAGCGATCTCGTTCGCAACACGATTGAAAA
GGATATTCATAAAAATCCAATGGATTCACGTACGGATGAAGCGCTTAAAGAAATCTATGAACGT
CTTCGTCCAGGTGAGCCTAAAACAGCTGATAGTTCACGTAGTCTATTGGTCGCTCGTTTCTTTG
ATCCACATCGTTACGACTTGGCGGCAGTTGGTCGTTATAAAATCAATAAAAAATTAAACATTAA
AACACGTTTGTTAAATCAAACGATTGCAGAGCCTTTGGTAGATCCAGAAACAGGTGAAATCTTG
GTTGAAGCTGGAACGGTTATGACGCGTAGTGTCATTGATAGCATTGCAGAATACTTGGACGGTG
ATTTGAATAAAATCACTTATATTCCAAATGATGCAGCTGTGTTAACAGAGCCAGTTGTTCTTCA
AAAATTCAAAGTGGTGGCGCCAACTGATCCAGATCGTGTGGTGACTATTATTGGTAATGCCAAC
CCAGGAGATCGAGTTCATACGATTACGCCAGCAGATATTTTGGCTGAGATGAATTACTTCTTGA
ACCTCGCTGAAGGACTTGGTCGTGTGGACGATATTGACCACTTGGGAAATCGTCGGATTCGTGC
CGTTGGTGAATTGCTTGCTAACCAAGTACGTCTTGGCTTGTCTCGTATGGAGCGAAACGTTCGG
GAGCGCATGAGTGTGCAAGATAATGAAGTGTTGACACCGCAACAAATCATTAACATCCGCCCAG
TCACAGCAGCTATCAAAGAATTCTTTGGTTCATCTCAATTGTCTCAATTTATGGACCAACATAA
TCCACTGTCTGAATTGTCTCACAAACGCCGTTTGTCAGCCTTGGGACCTGGTGGTTTGACTCGT
GATCGTGCTGGATATGAAGTGCGTGACGTGCACTATACCCACTATGGTCGTATGTGTCCGATTG
AAACGCCTGAAGGACCAAACATCGGTTTGATCAATAACTTGTCTTCTTATGGACACTTGAATAA
ATATGGCTTTATCCAAACGCCGTATCGTAAAGTGGATCGTGAAACAGGTCTGGTCACCAATGAA
ATCGTTTGGCTGACAGCGGACGAAGAAGATGAATTTATCGTAGCGCAAGCAAATTCTAAATTAA
CAGAAGATGGTCGTTTTGCAGAAGCGATTGTCATGGGACGTCACCAAGGGAACAACCAAGAATT
TCCTTCAGATCAAGTAGACTTCATGGATGTATCGCCTAAGCAGGTAGTTGCGGTTGCGACAGCA
TGTATTCCTTTCCTTGAAAACGACGACTCAAACCGTGCTCTCATGGGTGCCAACATGCAACGTC
AGGCGGTACCGTTGATTGATCCGCATGCACCATATGTTGGTACTGGTATGGAATACCAAGCAGC
TCATGACTCTGGTGCGGCGATTATTGCCCAACACGACGGTAAAGTTGTATATTCTGATGCAGCC
AAAGTTGAAGTTCGTCGTGAAGATGGCTCACTTGATGTCTATCATATTACGAAATTCCGCCGTT
CAAACTCTGGTACTTCTTACAACCAACGTACGCTGGTAAAAGTTGGCGATACAGTTGAAAAAGG
```

-continued

```
TGACTTTATCGCAGACGGACCTTCTATGGAAAAAGGTGAAATGGCACTTGGACAAAATCCAATC

GTTGCTTATATGACATGGGAAGGTTACAACTTTGAAGATGCCGTTATCATGAGTGAGCGTTTAG

TGAAAGACGATGTTTACACATCTGTTCACTTGGAGGAATTTGAATCAGAAACACGTGATACAAA  STRF
GCTTGGACCTGAAGAAATCACGCGCGAAATTCCAAACGTCGGTGAAGATGCTTTGAGAGACCTT

GACGAAACGGGAATTATCCGCATTGGTGCTGAGGTAAAAGAAGGCGACATTCTTGTCGGTAAAG

TAACACCGAAAGGTGAAAAAGACTTATCTGCTGAAGAACGCCTGCTTCATGCAATTTTCGGTGA

TAAATCTCGTGAAGTACGTGATACTTCCCTTCGTGTACCACATGGTGGTGCAGGGGTTGTCCGT

GATGTGAAAATCTTTACTCGTGCGAACGGTGATGAATTGCAATCTGGTGTCAACATGTTGGTAC

GTGTTTACATCGCTCAAAAACGGAAAATCCGTGTTGGGGATAAGATGGCTGGACGTCACGGAAA

CAAAGGGGTTGTTTCCCGCATTGTTCCAGTTGAGGATATGCCGTATCTTCCAGATGGAACACCA

GTTGATATTATGTTGAACCCACTTGGGGTGCCATCTCGTATGAATATTGGTCAAGTTATGGAGC

TTCACCTCGGTATGGCTGCTCGCAACCTTGGCATTCACATTGCAACACCAGTATTTGACGGGGC

TAGCTCAGATGATCTTTGGGAAACCGTTCGTGAAGCTGGCATGGATAGCGATGCTAAGACAATC

CTTTATGATGGCCGTACTGGTGAGCCATTTGATAATCGTGTATCCGTTGGTGTCATGTACATGA

TCAAACTCCACCATATGGTTGATGATAAGCTCCATGCCCGTTCCGTTGGTCCTTATTCAACCGT  STRR
TACGCAACAACCTCTTGGTGGTAAAGCGCAGTTTGGTGGACAACGTTTTGGAGAAATGGAAGTT

TGGGCTCTTGAAGCCTACGGTGCTTCTAACGTCCTTCAAGAAATCTTGACTTACAAGTCAGATG

ACATCAATGGTCGTTTGAGAGCTTATGAAGCCATTACCAAAGGTAAGCCAATTCCAAAACCAGG

TGTTCCAGAATCCTTCCGTGTCCTTGTAAAAGAATTGCAATCACTTGGTCTTGACATGCGTGTC

CTTGATGAAGACGACAATGAAGTCGAACTTCGTGACTTGGACGAAGGCATGGATGATGATGTGA

TTCATGTAGACGATCTTGAAAAAGCACGTGAAAAAGCAGCACAAGAAGCAAAAGCCGCTTTTGA

TGCTGAAGGGAAAGAATAAGAACTGATTCAATAGATAATAAAGAAAGGTAAGAAATAGTGGTTG

ATGTAAATCGTTTTCAAAGTATGCAAATCACCCTAGCTTCTCCTAGTAAAGTCCGCTCTTGGTC

TTATGGAGAAGTGAAGAAACCTGAAACAATTAACTACCGCACACTAAAACCAGAACGCGAAGGG

CTTTTTGATGAAGTCATCTTTGGTCCTACGAAAGACTGGGAATGTGCGTGTGGAAAATATAAAC

GGATTCGTTATAAAGGAATCATTTGTGACCGTTGTGGTGTTGAAGTAACTCGTACTAAAGTTCG

TCGTGAACGTATGGGACATATTGAGTTGAAAGCCCCAGTCTCCTCATATTTGGTATTTTAAAGG

AATTCCAANTCGCATGGGCTTGACCTTGGACATGAGCCCTCGTGCTCTTGAAGAAGTCATNTAN

TTTGCAGCTTATGTGGTGANTGACCCTAAAGATACNCCACTTGAGCACAAATCCATTATGACAG

AGCGGGATGGTTNGTGAACGCTGACNTGAATATGGCCAAGGCTCTTTTGTTGCAAAAATGGGTG

YTGAAGCAATCCAAGATCTNNTGAAACANGTAGACCTGGAAAAAGAAATTGCAGAGCTCAAAGA

TGAATTAAAAACGGCAAGTGGGCAAAAGCGCGTAAANGCTAANTTCGTCGNTNNGACTCTTTTC

GATNCTTTCCAAAAATCATGGTACACAAAACCAGAACTGGATGGTCTTAACCCATCNTNTCACC

GCTCATTCCAGACAC  -3'
```

SEQ ID no 2: Sequence of the rpoB gene of *Streptococcus equinus*. This sequence measures 4118 base pairs, has a guanosine plus cytosine content of 41% and is deposited in GenBank under number GenBank accession AF 535187:

```
5'-CACGCGTGGTCGACGGCCCGGGCTGGTGAATTGTCATAAGTTGTGTAGTAGTAAATTCCCTTAT

CAGTGTTGATGCATGAGCTATAAATAGTGTACTCATATTTGCCACTTTCATCGACATAGCAAAG
```

-continued

```
TCCTTTTTCTTGTTCAACGGATTTTAAAATGTGGAAGAATTGATTAACACTGCTTTCTTCTGTT
TCTTCAGCCACAGAATTTAATTTTGTAAAAGTAACTTTTACATAACGTGACATTGATGATAAAT
CACCAGGCAAGCCAAGTCCACCCATGCCACGGCTATAAGTTTCAAGTTCTAACTCTTTAGCAAA
ACGATTTTCTGAAACCTTTGGAGATAGATGACGATAGTTATTCAAATTGAATAATTGTTTATCA
AAAGTTGGATTATTAGTCAAAACACCTGTTGAGTTATTCGTAAACTTATAGGGCACGCGTGGTC
GACGGCCCGGGCTGGTAAAGACTTCTTGGATAACGGATTAAMAGAAGTTTTTGAAGATGTACTT
CCGATTACAAACTTTACGGATACTATGGAGCTTGAATTTGTTGGTTACGAATTGAAAGAGCCTA
AGTATACGCTTGAAGAAGCTCGTATCCACGATGCATCTTATTCAGCACCTATTTTTGTAACCTT
CCGTTTGATTAATAAAGAAACAGGAGAAATCAAAACTCAAGAAGTTTTCTTCGGTGATTTCCCA
ATTATGACTGAAATGGGTACATTCATCATCAACGGTGGTGAACGTATTATCGTTTCTCAGTTGG
TTCGTTCTCCTGGTGTTTATTTCAACGATAAAGTTGATAAAAACGGTAAAGTTGGTTACGGTTC
AACTGTAATCCCTAACCGTGGAGCATGGCTTGAATTAGAAACAGATTCAAAAGATATTGCTTAC
ACACGTATCGACCGTACACGTAAAATTCCATTTACAACTCTTGTACGTGCGCTTGGTTTCTCAG
GTGATGATGAAATCATGGATATCTTTGGTGATAGCGAACTTGTTCGTAACACAATCGAAAAAGA
TATTCACAAAAACCCAGCAGACTCACGTACTGACGAAGCTCTTAAAGAAATTTACGAACGCCTT
CGTCCAGGTGAACCAAAAACAGCTGATAGCTCACGTAGCTTGCTTGTAGCTCGTTTCTTTGACC
CACGTCGTTATGACTTGGCAGCTGTTGGTCGTTACAAAATCAACAAAAAACTTAACATCAAGAC
TCGTCTTTTGAACCAAACAATCGCTGAAAACTTGGTTGATGCTGAAACTGGTGAAATCCTTGTT
GAAGCTGGTACAGTAATGACACGTGACGTGATTGATTCAATCGCTGATCAATTGGATGGTGACC
TTAACAAATTTGTTTACACACCAAATGATTACGCTGTTGTCACTGAACCTGTTGTTCTTCAAAA
ATTCAAAGTTGTTGCACCAAACGATCCAGACCGCGTTGTTACAATCGTTGGTAACGCAAATCCT
GATGACAAAGCGCGTGCGCTTACACCAGCTCATATCTTGGCAGAAATGTCTTACTTCCTTAACC
TTGCTGAAGGTCTAGGTAAAGTTGATGATATCGACCACCTTGGGAATCGTCGTATTCGTGCCGT
TGGTGAATTCCTTGCTAACCAATTCCGTATTGGTCTTGCTCGTATGGAACGTAACGTTCGGGAA
CGTATGTCAGTTCAAGACAACGAAGTGTTGACACCACAACAAATCATCAACATTCGTCCTGTTA
CTGCAGCCGTTAAAGAATTCTTCGGTTCATCTCAATTGTCACAGTTCATGGACCAACACAACCC
ACTTTCTGAGTTGTCTCACAAACGTCGTTTGTCAGCCTTAGGACCTGGTGGTTTGACTCGTGAC
CGTGCTGGTTATGAAGTTCGTGACGTGCACTACACTCACTATGGTCGTATGTGTCCGATTGAAA
CTCCTGAAGGACCTAACATCGGTTTGATCAATAACTTGTCAACATACGGACACCTTAATAAATA
TGGTTTCATCCAAACACCATATCGTAAAGTTGACCGCGCTACAGGTGTGATTACAAACGAAATC
GTTTGGTTGACTGCCGATGAAGAAGATGAATACACAGTAGCACAGGCTAACTCAAAACTTAACG
AAGATGGAACATTTGCTGAAGACATCGTTATGGGACGTCACCAAGGTAATAACCAAGAGTTCCC
AGCAAGCGTTGTTGACTTCGTAGACGTTTCACCTAAACAAGTAGTTGCCGTTGCGACAGCATGT
ATTCCTTTCCTTGAAAACGATGACTCTAACCGTGCCCTTATGGGTGCCAACATGCAACGTCAAG
CGGTGCCATTGATTGATCCACACGCACCATATGTTGGTACTGGTATGGAATATCAAGCAGCCCA
CGACTCAGGTGCTGCAGTTATCGCTAAACACGATGGACGCGTTATCTTCTCTGATGCTGAAAAA
GTTGAAGTTCGTCGCGAAGATGGTTCACTTGATGTTTACCACATTACTAAATTCCGTCGTTCTA
ACTCAGGTACAGCTTATAACCAACATACACTTGTTAAAGTTGGCGATATCGTTGAAAAAGGTGA
CTTCATCGCTGATGGTCCTTCAATGGAAAAAGGTGAAATGGCCCTTGGTCAAAACCCAATCGTC
GCTTACATGACTTGGGATGGTTATAACTATGAAGATGCCATCATCTTGAGTGAACGTCTTGTTA
```

```
                                                                        -continued
AAGAAGATGTTTATACATCAGTTCACTTGGAAGAATTTGAATCAGAAACACGTGATACTAAGTT STRF
AGGCCCTGAAGAAATCACTCGCGAAATTCCAAACGTTGGTGAAGAAGCTCTTAAAGACCTTGAC
GAAATGGGTATTATCCGTATCGGTGCTGAAGTTAAAGAAGGTGACATCCTTGTAGGTAAAGTAA
CACCTAAAGGTGAAAAAGACCTTTCTGCTGAACAGCGCCTTCTTCACGCAATCTTCGGTGATAA
ATCACGTGAAGTTCGTGATACATCACTTCGTGTACCACACGGTGGAGATCGTGTCGTTCGTGAC
GTTAAAATCTTTACACGTGCAAACGGTGATGAATTACAATCAGGTGTTAACATGCTCGTTCGTG
TTTATATCGCACAAAAACGTAAAATCAAAGTCGGAGATAAAATGGCCGGTCGTCACGGTAACAA
AGGGGTTGTTTCTCGTGTTGTTCCAGTTGAAGACATGCCTTATCTTCCAGACGGAACTCCAGTC
GATATCATGTTGAACCCACTTGGGGTGCCATCTCGTATGAACATCGGACAAGTTATGGAGCTTC
ACCTTGGTATGGCTGCTCGTAACCTTGGTATTCACATTGCAACACCAGTCTTTGATGGGGCAAC
TTCTGAAGACCTTTGGGATACAGTTAACGAAGCTGGTATGGCTAGCGACGCTAAGACAGTTCTT
TACGATGGACGTACTGGTGAACCATTTGATAACCGTGTGTCAGTTGGTGTCATCTACATGATTA
AACTTCACCACATGGTTGATGATAAACTTCACGCACGTTCAGTTGGTCCTTACTCACTTGTTAC STRR
GCAACAACCTCTTGGTGGTAAAGCACAATTTGGTGGACAACGTTTCGGTGAAATGGAAGTTTGG
GCTTTGGAAGCTTACGGTGCATCAAATGTTCTTCAAGAAATCTTGACTTACAAAACAGATGATG
TCAACGGTCGTCTTAAAGCTTATGAAGCCATCACTAAAGGTAAACCAATTCCAAAACCAGGTGT
TCCAGAATCATTCCGAGTTCTTGTAAAAGAATTGCAATCACTTGGTCTTGACATGCGCGTGCTT
GATGAAGATGACAATGAAGTAGAACTTCGTGATCTTGATGAAGGTGAAGATGACGATGTTATGC
ACGTTGATGATCTTGAAAAAGCTCGTCAAAAACAAGAAGCAGAAGAAGCGGAAAAAGCAGAAGT
TTCTGCAGAAGAAACAAATAATAGGAAAGAACATTCAGACATGAGAGAGGCAAGACCTGCTTC
TCTTGGTCAGATTGTTTGATTGAGTCCTATAACGATAAATGATGTCTTACGAATCATGAATTTG
TAAGTCATGACAGTTAGAAAGTAGCGCAGCTATTTCAAAGTCATAAGAAGGTATCATGGTGACG
TAATCGTTACAGCCGGCCTC -3'
```

SEQ ID no 3: Sequence of the rpoB gene of *Abiotrophia defectiva*. This sequence measures 4325 base pairs, has a guanosine plus cytosine content of 47%, and is deposited in GenBank under number AF 535173:

```
5'-ATATAGGGCACGCGTGGTCGACGGCCCGGGCTGGTCCTAAACAACATGTAACGTCACTCCGATG
AGTTGGTTCTGTTGTCTTTTTTTTGCGCTTCAAAGACCGAAAAATGTCATTTGTCAACAATTAT
TAATAATTGTAACCTTAATGTAAAGTGGTGTTCTTAGATTATATTATAGGGGTGAATCGCTTGA
GTCATATCGTGAAATACGGTAAAAAAGCTGAGCGTCGAAGCTATGCGCGTATCGACGAAGTCTT
AGAGTTGCCGAACTTGATTGAAATCCAAACGGATTCCTACAAATGGTTCTTGGATGAAGGGCTA
AAAGTGATGTTCGAGGACATTTCGCCGATTGTCGACCATTCGGAGAACTTGGAACTTCATTTTG
TAGACTATGAGTTCAAGGAAGCTAAGTATAGCTTAGAAGAAGCTCGTAGCCATGACGCTAACTA
CTCAAAACCAATCTATGTAACCTTGCGCCTGTTCAACAAAGAGACAGGTGAAGTCAAAGAACAA
GAAGTCTTCTTCGGGGACTTCCCAATCATGACCGAAATGGGGACCTTCATTATCAACGGGGCGG
AACGGGTTATCGTTTCCCAGTTGGTACGTTCTCCAGGTGTCTACTTCCACGACCGTATGGACAA
GAAAGGCCGCCACAGCTATACTTCTACGCTTATTCCTAACCGTGGGGCTTGGTTGGAATTTGAA
TCAGATGCTAAGGGGATTGCCTACGTCCGCATTGACCGGACCCGGAAGATTCCATTGACTGTCT
TGATGCGTGCCTTAGGTTTTGGTTCAGATGACGAGATTTATGATATCTTCGGCCAATCTGAGCT
CTTAGACTTAACTATCGAGAAGGATGTTCACAAAAACATTCAAGACTCTCGTACGGAAGAAGCC
```

-continued

```
TTGAAGGACATTTACGAGCGTCTCCGTCCAGGTGAACCTAAGACCGCAGAAAGCTCACGTAACC
TCTTGGTTGCGCGCTTCTTCGACCCACGTCGCTATGACTTAGCACCTGTAGGTCGTTATAAGAT
CAATAAAAAGCTCCACCTCAAGAACCGTTTGGTTGGCTTGACTTTGGCTGAAACCTTGGTTAAC
CCAGAAACAGGCGAAGTGCTCTTTGAAGAAGGAACGGTCTTGGATCAAGAACGTGTTCAAGCCC
TGATTCCATACTTAGAGGCTGGCTTGAATAAGGTAACCCTCTATCCTTCTGAAGATACTGTGGT
AGCTCAACCAATTGATTTACAAATCATCAAAGTTTATTCACCTAAGAACGCCGAGCAAGTGATT
AACATCATCGGTAACGGGAACATTGAGAAGATTAAGTGCTTGACGCCAGCTGACATTATTGCGT
CAATGAACTACTATCTCTATTTAGACCAAGGAATTGGTGTGACAGATGATATCGACCACTTGGC
TAACCGTCGTATTCGTTCAGTCGGTGAATTATTGCAAAACCAATTCCGTATCGGGCTATCCCGG
ATGGAACGGGTAGTGCGTGAACGTATGTCGCTCCAAGATGTTGCGACCATCACACCGCAACAAT
TGATTAACATTCGTCCAGTAGTGGCGGCTATTAAGGAATTCTTCGGTTCATCCCAGTTGTCACA
ATTCATGGACCAAGTTAACCCACTCGGGGAATTGACCCACAAACGTCGTCTGTCAGCCTTAGGG
CCTGGTGGTTTGACGCGGGACCGTGCCGGCTATGAAGTGCGGGACGTTCACTACTCTCACTACG
GCCGTATGTGTCCAATCGAGACGCCAGAAGGTCCTAACATCGGGTTGATTAACAGCTTGTCTTC
TTATGCCAAGATTAACAAGTATGGTTTTATTGAGACGCCTTACCGTAAAGTGGACAAATCGGTT
ACGCCACACCGTGTCACGACCGAAATTGACTACCTAGCAGCGGACGAGGAAGACTTGTACGTAG
TAGCCCAAGCCAACTCTAAACTCAACGAAGACGGGACCTTCGCCAATGACCTAGTTATGGCGCG
TTTCCGTTCACAAAACATTGAGGTTAACGTTGACCAAGTAGACTACATGGACGTATCGCCAAAA
CAGGTTGTCGCTGTCGCGACTGCTAGCATTCCGTTCTTGGAAAACGACGACTCCAACCGGGGCT
TGATGGGTGCCAACATGCAACGTCAAGCTGTGCCACTTATTAATCCACAATCCCCACTGATTGG
GACTGGGATGGAATATAAGGCAGCACACGACTCTGGGGCTGCGCTCTTATGTAAGCGCGCCGGT
GAAGTGGTTTATGTCGATGCTAACAAGGTGCGCGTGCGCACTCCAGAAGGTGAAGTTGACGAAT
ACCGTTTAACCAAGTTTGCACGTTCTAACGCTGGGACCTGTTACAACCAACGTCCAATCGTAGA
ATTAGGCGACCAAGTTGATGCCTTGGAAATCTTAGCAGATGGTCCATCTATGCAAAATGGGGAG
ATGGCCCTCGGTCAAAACCCACTGGTAGCCTTCATGACTTGGGAAGGGTATAACTATGAGGACG
CGGTTATCATGTCTGAACGTCTGGTCAAAGACGATGTTTATACCTCTATCCACATTGAAGAATA
TGAATCAGAGTCCCGTGAYACYAAGTTAGGCCCTGAAGAAATTACACGCGAAATTCCAAACGTG STRF
TCCGAAGATGCCCTCAAGTACTTAGACAAAGACGGGATTATCTGTATCGGGGCGGAAGTAAAAG
ACGGCGATATCTTAGTTGGTAAGGTAACACCAAAAGGTGTGACCGAGTTGTCTGCGGAAGAACG
CTTGCTCCATGCTATCTTCGGTGAGAAGGCGCGTGAAGTACGTGATACTTCCTTGCGTGTGCCA
CACGGCGGGGCGGGATTGTCCACGACGTTAAAATCTTTACCCGCGAAGCTGGCGACGAATTGG
CACCAGGTGTCAACAAGCTAGTCCGCGTCTACATCGTACAAAAACGTAAAATCAATGAAGGGGA
TAAGATGGCCGGTCGTCACGGTAACAAAGGGGTTGTCTCCCTTATCATGCCGGAAGAAGATATG
CCATTCTTACCAGATGGTACCCCAGTTGATATCATGTTGAACCCATTAGGGGTTCCATCCCGTA
TGAACATCGGGCAAGTCCTAGAGTTACACTTGGGGATGGCTGCTCGCGAAATGGGCATCAAGAT
TGCAACACCTGTCTTTGACGGTGCTAGTGAAGAAGATGTCTGGGAAACAGTTAAGGAAGCCGGC
TTAGAAGCTGACGCTAAGACTATCTTATATGATGGTCGAACCGGTGAACCATTTGACCGTAAAG
TCTCTGTTGGGGTTATGTACATGATTAAGTTGGCCCACATGGTCGATGACAAGTTGCACGCCCG STRR
TTCAACAGGTCCATACTCTCTGGTTACCCAACAACCATTGGGTGGTAAAGCTCAATTTGGTGGG
CAACGTTTCGGGGAGATGGAGGTTTGGGCCCTA -3'
```

SEQ ID no 4: Partial sequence of the rpoB gene of *Streptococcus mutans*. This sequence measures 3198 base pairs, has a guanosine plus cytosine content of 42%, and is deposited with GenBank under number AF 535167.

```
5'-GGACCCTTTTATGACTTCTTGGATACAGGTCTGAAGGAAGTTTTTGAAGATGTGCTTCCAATTT
CCAATTTCACAGACACTATGGAATTAGAGTTTGTGGGTTATGAGTTGAAAGAGCCTAAGTATAC
ATTGGAAGAAGCACGTGCTCATGATGCACATTATTCTGCCCCCATCTTTGTTACTTTCCGTCTC
ATCAATAAAGAAACTGGTGAAATTAAGACACAAGAAGTATTTTTTGGTGATTTTCCCTTGATGA
CTGAAATGGGTACTTTTATTATTAATGGTGCTGAACGTATTATCGTTTCTCAGTTGGTACGTTC
ACCAGGTGTTTATTTTAATGATAAAGTGGATAAAAATGGGAAAATTGGCTATGGTTCAACTGTT
ATCCCTAACCGCGGTGCTTGGCTTGAGCTTGAAACGGACTCTAAGGATATTGCTTATACTCGTA
TTGATCGTACTCGTAAAATTCCTTTTACGACGCTGGTTCGTGCACTCGGTTTTTCCGGGGATGA
TGAGATTATTGATATTTTTGGTGATAGCGAATTGGTTCGTAATACCATTGAAAAAGATATCCAT
AAAAATCCTAATGACTCTCGTACAGATGAAGCTCTCAAGGAANTTATGAACGTCTTCGTCCGGG
TGAACCTAAAACGGCAGATTCNTCACGCAGTCTTCTGATTGCACGTTTCTTTGATGCGCGCCGT
TATGATTAGCAGCTGTTGGCCGCTATAGATAATAAGAAGTTAAACGTCAAAACGGGTCTTTGAA
TCAAGTCATTGGCTGAAAANNAGTAGATCTGAAACAGGCGAAATTCTTGTTGAAAGCTGGGACT
GAAATGACACGCAGTGTAATTGATTCGATTGCAGATTATCTTGATGGAGATCTCAATAAAATTG
TTTATACGCCAAATGAATACGCTGTTTTGACAGAACCTGTTGTTCTTCAAAAATTCAAAGTTAT
GGCTCCAAATGATCCAGACCGCACGGTTACTGTTATTGGTAATGCCAGTCCAAGATGACAAAGT
ACGTCACTTGACACCAGCCGATACGTATTAGCTGAAATGTCTTATTTCCTTAACTTGGCTGAGG
GTNTAGGTAAAGTTGATGATATTGACCATTTAGGCAACCGACGTATTCGTGCTGTTGGTGAATT
GCTTGCTAATCAATTTCGTATTGGTTTGGCACGTATGGAACCCAATGTTCGTGAACGCATGTCC
GTTCAAGATAATGAAGTCTTAACGCCACAACAGATTATTAACATTCGCCCTGTAACAGCGGCAA
TTAAAGAGTTTTTTGGTTCTTCTCAATTGTCACAGTTCATGGACCAACACAATCCACTGTCTGA
ATTGTCTCATAAACGCCGTTTGTCAGCTTTAGGTCCTGGTGGTTTAACACGCGACCGTGCTGGT
TATGAAGTCCGTGATGTGCACTATACGCATTATGGTCGTATGTGTCCAATTGAAACGCCTGAAG
GACCAAATATTGGATTGATTAATAACTTGTCTTCCTATGGTCATCTTAATAAATATGGATTTAT
CCAAACACCATACCGTAAAGTTGACCGTGAGACAGGTAAAGTAACCAATGAAATCGAATGGCTT
ACTGCTGATGAAGAAGATGAATTCACTGTAGCTCAGGCTAACTCAAAACTCAATGAAGATGGAA_STRF
GCTTTGCTGAAGAAATCGTCATGGGACGTCATCAAGGGAATAACCAAGAGTTTCCAGCAAGTTC
TGTTGAATATATGGATGTTTCTCCTAAGCAGGTAGTTGCGGTAGCGACAGCATGTATTCCTTTC
CTTGAAAATGATGACTCCAACCGTGCCCTTATGGGAGCTAACATGCAGCGCCAAGCTGTGCCAT
TGATTGATCCTAAAGCACCTTTTGTTGGAACTGGTATGGAATATCAAGCAGCCCATGATTCTGG
AGCCGCTATTATCGCTCAACATAATGGGAAAGTGGTTTATTCCOATGCAGATAAGATTGAAGTT
CGCCGTGAAGATGGCTCACTAGATGTTTATCATGTTACCAAATTCCGTCGTTCTAACTCTGGAA
CTGCCTACAATCAACGTACTCTTGTTAGGGTAGGCGATAGTGTTGAGAAGGGGGACTTTATTGC
AGATGGTCCTTCTATGGAAAAGGGTGAGATGGCTCTTGGACAAAATCCAGTGGTTGCTTACATG
ACTTGGGAGGGTTACAACTTTGAAGATGCTGTTATCATGAGCGAGCGTCTTGTCAAGGATGATG
TTTATACTTCTGTCCATTTAGAAGAATTTGAATCTGAAACTCGTGATACAAAGCTTGGACCTGA
AGAAATTACGCGTGAAATCCCAAATGTTGGTGAAGATGCCCTGAAAGACCTTGATGAAATGGGA
ATTATTCGCATTGGTGCTGAGGTTAAAGAAGGTGATATTCTAGTTGGTAAAGTGACTCCTAAAG
```

-continued
```
GAGAAAAAGATCTTTCTGCAGAAGAACGCCTCTTGCATGCCATTTTTGGTGACAAATCACGTGA

AGTTCGTGATACTTCTCTTCGTGTACCTCATGGTGGCGACGGTGTTGTTTGTGATGTGAAAATC

TTTACACGTGCTAATGGAGATGAACTTCAATCAGGTGTTAACATGCTGGTTCGTGTTTATATCG

CTCAAAAACGTAAAATCAAGGTCGGAGATAAGATGGCCGGACGTCATGGTAACAAGGGTGTCGT

TTCCCCTATTGTACCAGTGGAAGATATGCCATATCTTCCAGATGGAACACCTGTTGATATCATG

CTTAATCCACTTGGGGTGCCATCACGGATGAACATTGGGCAAGTTATGGAACTCCATCTTGGTA

TGGCTGCTCGTAATTTGGGCATTCATATTGCAACGCCTGTCTTTGACGGAGCAACTTCTGATGA

TCTTTGGGAAACAGTPAAAGAAGCCGGTATGGATTCTGATGCTAAAACTGTTCTTTATGATGGT

CGCACAGGGGAGCCGTTTGATAATCGTGTATCAGTTGGTGTTATGTATATGATTAAACTTCACC_STRR

ACATGGTTGATGAYAACCATTTTGTCTATGCAMAGWTCAGTTGGCCCTTAKTCAAYGAWTAMTC

AGASGARTTCCTGCTWGGTGTAAAGGCTNCAATTGTCTTTAGAGGTTAAGGCTGGTGAAATAAC

GGTATGCTGGTATTGATGGCAATGGGCAAGTGAATANTCAACACCGGCCGTCTACANCGTGC- 3'
```

SEQ ID no 5: Partial sequence of the rpoB gene of *Enterococcus faecalis*. This sequence measures 3096 base pairs, has a guanosine plus cytosine content of 42%, and is deposited with GenBank under number AF 535175.

```
5'-GACCCTTATCAATTGGTTTTTAGATGAGGGACTTCGTGAAATGTTTGAAGACATTTTACCAATT

GATGATTTCCAAGGAAACTTATCCTTAGAATTTGTTGACTATGAATTAAAAGAACCAAAGTACA

CAGTAGAAGAAGCCCGCGCACATGATGCCAACTATTCTGCGCCATTACATGTAACATTACGTTT

AACCAACCGTGAAACAGGTGAAATTAAATCCCAAGAAGTCTTCTTCGGCGATTTCCCATTAATG

ACAGAAATGGGTACCTTCATCATCAACGGGGCAGAACGTGTTATCGTTTCCCAATTAGTTCGTT

CTCCAGGTGTTTACTTCCATGGAAAAGTGGACAAAAACGGCAAAGAAGGTTTTGGCTCAACAGT

CATTCCTAACCGTGGTGCATGGTTAGAAATGGAAACAGATGCGAAAGACATTTCTTATGTTCGG

ATTGACCGCACACGTAAAATTCCTTTAACTGTGTTAGTTCGTGCTTTAGGTTTCGGTTCAGATG

ATACCATCTTCGAAATTTTCGGCGACAGCGAAAGCTTACGCAACACAATTGAAAAGATTTACA

CAAAAACGCAAGTGATTCTCGTACAGAAGAAGGCTTGAAAGACATTTATGAACGTCTTCGCCCA

GGCGAACCAAAAACAGCAGATAGCTCACGTAGCTTGTTAACTTGCACGTTTCTTTGATCCAAAA

CGTTATGATTTGGCAAACGTTGGTCGCTACAAAGTTAACAAAAAATTAGACTTAAAAACACGTC

TATTAAACTTAACCTTAGCTGAAACGCTAGTTGATCCAGAAACTGGTGTAAATCATTGTCGAAA

AAGGCACAGTTTTAACACACTACATCATGGAAACATTAAGGCPATACATTGACAAACGGCTTAA

ACAGCGTAACTTACTATCCAAGTGAAGATGCGGTAGTAACTGAACCAATGACGATCCAAGTGAT

TCAAGTTCTTTCACCAAAAGATCCTGAACGTATCGTAAATGTGATTGGTAACGGCTATCCAGAC

GACAGCGTAAAAACAGTTCCTCCAGCAGATATCGTTQCTTCAATGAGCTACTTCTTCAACTTAA

TGGAAGATATCGGTAATGTCGATGACATCGACCACTTAGGTAATCGTCGTATCCGTTCAGTAGG

CGAATTATTACAAAACCAATTCCGTATTGGTTTAGCCCGTATGGAACGTGTGGTTCGTGAAAGA

ATGTCTATTCAAGACACAGAAACATTGACACCACAACAATTAATTAACATCCGTCCAGTGGTAG

CAAGTATCAAAGAATTCTTTGGTTCTTCACAGTTATCACAGTTCATGGACCAAACAAACCCATT

AGGTGAGTTAACCCATAAACGTCGTCTATCAGCCTTAGGGCCTGGTGGTTTGACTCGTGATCGT

GCCGGTTATGAAGTTCGTGACGTTCACTACTCTCACTATGGTCGTATGTGTCCAATTGAAACGC

CTGAGGGACCAAATATCGGGTTGATCAATAGCTTATCTAGTTATGCGAAAGTGAATAAATTTGG

TTTCATCGAAACGCCTTATCGCCGTGTTGATCGTGCGACAGGCCGTGTTACTGATCAAGTAGAT
```

-continued

```
TACTTAACAGCAGACATCGAAGACCATTATATCGTAGCGCAAGCGAACTCACTTTTAAATGAAG

ATGGCACATTTGCCAATGATGTTGTTATGGCGCGTCTACAAAGTGAAAACTTAGAAGTTGCCGT

AGACAAAGTTGACTACATGGACGTTTCACCAAAACAAGTAGTCGCAGTCGCAACAGCATGTATT

CCTTTCTTAGAAAACGATGACTCCAACCGTGCCTTGATGGGTGCCAACATGCAGCGTCAAGCGG

TGCCGTTAATTCAACCACGCTCTCCGTGGGTAGGTACAGGTATGGAATATAAATCAGCCCATGA

CTCAGGTGCTGCTTTACTATGTAAACATGACGGTGTCGTAGAATTCGTCGATGCAAAAGAAATT  STRF

CGCGTTCGTCGCGACAATGGCGCATTAGACAAATATATGGTTACAAAATTCCGTCGTTCTAACT

CAGGAACAAGCTACAACCAACCCCCAATTGTTCACTTAGGTGAAAAGTTGAAAAGGCGATACTT

TACCGGATGGACCTTCTATGGAAGAAGCGAAATGGCTTTATGGCAAAACGTCTTAGTTGCCTTC

ATGACATGGGAAGGTTACAACTACGAGGATGCCATTATCATGAGCCGTCGTTTAGTTAAAGACG

ATGTCTACACTTCTGTGCATATTGAAGAATATGAATCAGAAGCACGTGATACAAAATTAGGACC

TGAAGAAATTACCCGTGAAATTCCAAACGTTGGGGAAGACGCGTTGAAAGACTTAGACGAAATG

GGGATTATCCGCATTGGTGCTGAAGTTCAAGATGGCGACTTACTAGTTGGGAAAGTCACACCTA

AAGGGGTCACAGAATTATCTGCAGAAGAACGTTTATTACACGCAATCTTCGGGGAAAAAGCCCG

CGAAGTTCGTGATACGTCTCTCCGTGTACCTCACGGTGGCGGCGGTATCGTTCATGATGTGAAA

ATCTTTACTCGTGAAGCTGGCGATGAATTATCACCAGGTGTCAACATGTTAGTTCGTGTCTATA

TCGTTCAAAAACGTAAAATTCACGAAGGAGATAAAATGGCGGGACGTCACGGAAATAAAGGGGT

TGTTTCCCGTATTATGCCGGAAGAAGATATGCCATTCTTACCTGACGGAACACCTGTTGATATC

ATGTTGAACCCATTAGGGGTACCTTCTCGTATGAATATCGGACAAGTACTTGAATTACACTTAG

GTATGGCTGCTCGCCAATTAGGTATTCACGTCGCAACACCTGTTTTCGATGGGGCAACCGATGA

AGACGTTTGGGAAACTGTTCGTGAAGCTGGTATGGCTAGCGATGCTAAAACAGTTCTTTACGAT

GGACGTACAGGTGAACCATTTGATAACCGTATTTCCGTTGGTGTCATGTATATGATTAAATTAG

CCCACATGGTTGATGACAAATTGCATGCTCGTTCAATCGGACCTTACTCTCTTGTTACGCAACA  STRR

ACCGTTGGGTGTAAAGCTCAATTC-3'
```

In the preceding sequences, the K nucleotide designates T or G, the M nucleotide designates A or C, the R nucleotide designates A or G, the W nucleotide designates A or T, the Y nucleotide designates C or T and the N nucleotide designates A, T, C or G.

EXAMPLE 2

Partial Sequencing of the rpoB Gene of 28 Species of Genus *Streptococcus* and Related Genera From the alignment of the complete sequences of the rpoB gene in *Streptococcus* spp. and *Abiotrophia defectiva* in example 1 and those known in GenBank (*Streptococcus pneumoniae* AE008542 and *Streptococcus pyogenes* AE006480) a set of primers was chosen for the amplification and sequencing of a 709 to 740 bp fragment of this gene in 28 type strains of these bacterial genera. The sequences of these primers were:

```
SEQ ID n° 6:    5'-AARYTIGMCCTGAAGAAAT-3'

SEQ ID n° 7:    5'-TGIARTTTRTCATCAACCATGTG-3'
```

Sequence SEQ ID no 7 was used as 3' primer and therefore represents the complementary reverse sequence of the direct strand represented in preceding sequences SEQ ID no 1 to 5.

These primers are incorporated with the DNA extracted from the bacteria during PCR under the following conditions: denaturing at 95° C. for 1 min followed by 35 cycles comprising a denaturing step at 94° C. for 10 sec, a hybridisation step at 52° C. for 10 sec and an elongation step at 72° C. for 30 sec.

The amplified products are sequenced with the same primers SEQ ID no 6 and SEQ ID no 7 under the following conditions: denaturing at 95° C. for 1 min followed by 30 cycles comprising a denaturing step at 95° C. for 30 sec. a hybridisation step at 52° C. for 30 sec and a hybridisation step at 62° C. for 1 min. The sequencing products are analysed on a ABI PRISM 3100 sequencer.

The inventors determined the position of these two primers SEQ ID no 6 and SEQ ID no 7, so as to observe the following criteria:

1—sequence flanked by these two primers specific to the species of the bacterium. This condition is verified after alignment of the fragments of around 720 bp with all the sequences of the rpoB bacterial genes available in computerized data banks, 2—search for the shortest possible identification region to achieve the best possible increase in the sensitivity of molecular detection,
3—primer length of 18 to 22 bp,
4—sequence of primers showing a close melting temperature,
5—sequence of primers not enabling auto-hybridisation or complementarity The obtained rpoB gene fragments of the bacterial species of genus *Streptococcus* and said related genera have approximately 720 (709 to 732) base pairs and their sequence is specific to each species of this genus therefore permitting molecular identification of the bacteria of the 28 species tested, i.e.:

SEQ ID no 8: partial sequence of the rpoB gene in *Streptococcus suis* CIP 1032 17$^T$ measuring 709 base pairs:

```
5'-CGCGAAATTCCAAACGTTGGTGAAGATGCCCTTCGCAACTTGGACGAAA
TGGGGATTATCCGTATTGGTGCCGAAGTTAAAGAGGGCGACATTCTTGTTGG
TAAAGTCACACCAAAAGGTGAAAAAGATCTTTCTGCTGAAGAGCGTCTCTTGC
ACGCAATCTTCGGTGACAAGTCACGTGAAGTACGTGATACCTCTCTTCGTGTA
CCTCACGGTGCCGATGGTGTCGTTCGTGATGTGAAAATCTTTACTCGTGCCAA
CGGTGATGAATTGCAATCAGGTGTTAACATGTTGGTTCGTGTTTACATCGCTC
AAAAACGTAAGATCAAGGTCGGAGATAAGATGGCCGGTCGTCACGGTAACAA
GGGTGTCGTTTCACGTATTGTACCTGTTGAGGATATGCCATATCTTCCAGATG
GAACACCAGTTGACATCATGTTGAACCCACTCGGGGTGCGATCACGTATGAAC
ATCGGTCAGGTTATGGAACTTCACTTGGGTATGGCGGCTCGCAACTTGGGCA
TCCATATCGCAACACCAGTTTTCGATGGTGCAAGTTCAGAAGACCTCTGGTCA
ACTGTTAAAGAAGCAGGTATGGACTCAGATGCCAAGACCATTCTTTACGATGG
ACGTACAGGTGAACCATTTGACAACCGTGTATGTGTTGGTGTCATGTACATGA
TCAAGCTTCACGACATGGTTGATGACA-3'
```

SEQ ID no 9: partial sequence of the rpoB gene in *Streptococcus sanguinis* CIP 55.128$^T$ measuring 725 base pairs:

```
5'-TGTCATCAACCATGTGGTGAGCTTAATCATGTACATGACACCGACAGATA
CACGGTTGTCAAACGGCTCACCGGTACGTCCATCGTAAAGAATAGTCTTGGCA
TCGCTATCCATACCAGCTTCACGGACAGTATCCCAGAGGTCTTCTGAGCTTGC
TCCATCAAAGACCGGTGTCGCAATATGGATGCCCAAGTTACGTGCTGCCATAC
CAAGGTGAAGCTCCATAACCTGACCAATGTTCATACGTGATGGTACCCCGAGT
GGGTTCAGCATGATATCAACTGGTGTTCCGTCTGGCAAATAAGGCATGTCTTC
CACAGGAACGATACGGGATACAACCCCCTTGTTTCCGTGACGACCAGCCATCT
TATCTCCGACCTTGATCTTACGTTTTTGAGCGATGTAGACACGAACCAACATAT
TAACGCCAGATTGCAACTCATCACCATTAGCACGGGTAAAGATCTTCACGTCA
CGAACCACTCCATCAGCACCGTGCGGCACACGCAGAGAGGTATCACGGACTTC
ACGAGACTTGTCTCCGAAGATAGCGTGCAAGAGGCGCTCTTCAGCAGAAAGA
TCTTTTTCACCCTTAGGGGTAACTTTACCTACAAGGATATCGCCTTCCTTGACT
TCCGCCCCGATGCGGATAATACCCATTTCGTCCAAATTGCGTAGGGCATCTTC
CCCTACGTTTGGAATTTCGCGGGTAATTCTTCAGGTCA-3'
```

SEQ ID no 10: partial sequence of the rpoB gene in *Streptococcus salivarius* CIP 102503$^T$ measuring 728 base pairs:

```
5'-TTGTCATCAACCATGTGTGAAGTTTGATCATGTACATGACACCAACTGAT

ACACGGTTATCAAATGGTTCACCTGTACGTCCATCGTAAAGGATTGTCTTAGC

ATCACTATCGATACCTGCTTCACGAACAGTATCCCAGAGGTCTTCTGAGCTTGC

CCCGTCAAAGACTGGTGTTGCGATGTGGATACCCAAGTTACGAGCAGCCATA

CCAAGGTGAAGTTCCATAACCTGACCGATGTTCATACGTGATGGCACCCCAAG

AGGGTTCAACATGATATCAACTGGTGTACCGTCTGGAAGGTAAGGCATGTCT

TCAACAGGAACAATACGAGAAACAACCCCTTTGTTACCGTGACGACCGGCCAT

CTTATCTCCGACCTTAATCTTACGTTTTTGAGCGATGTAAACACGAACAAGCAT

GTTAACACCTGATTGCAATTCATCACCGTTTGCACGTGTGAAGATTTTAACATC

ACGAACGACACCATCACCACCGTGAGGTACACGGAGTGAGGTATCACGTACT

TCACGAGATTTATCACCAAAGATAGCATGGAGAAGACGTTCTTCAGCAGAAA

GGTCTTTTTCACCCTTAGGTGTTACCTTACCAACAAGAATGTCACCTTCTTTAA

CCTCAGCACCGATACGGATAATACCCATTTCGTCAAGGTCTTTGAGAGCTTCTT

CACCAACGTTTGGCAATTCACGTGTAATTTCTTCAGGTCCA-3'
```

SEQ ID no 11: partial sequence of the rpoB gene in *Streptococcus pyogenes* CIP 56.41[T] measuring 725 base pairs:

```
5'-TGTCATCAACCATGTGGTGAAGTTTGATCATATACATGACACCAACGGAT

ACACGGTTGTCAAATGGTTCACCGGTGCGACCATCATAAAGGACCGTCTTAGC

ATCGCTATCCATACCAGCTTCACGAACAGTGTCCCAAAGGTCTTCTGATGAAG

CCCCGTCAAAGACAGGTGTTGCAATGTGAATACCAAGATTACGAGCAGCCATA

CCAAGGTGAAGTTCCATAACCTGACCAATATTCATCCGTGATGGCACCCCAAG

AGGGTTCAACATGATGTCAACTGGTGTTCCGTCTGGAAGGTATGGCATGTCT

TCAACTGGTACAATACGTGAAACGACACCCTTGTTTCCGTGACGACCGGCCAT

TTTATCTCCGACCTTGATTTTACGTTTTTGAGCGATGTAAACACGCACAAGCAT

ATTAACACCTGATTGCAATTCATCGCCGTTAGCGCGTGTAAAGATTTTCACATC

ACGAACGATACCATCACCACCGTGAGGGACACGAAGTGAGGTATCACGCACT

TCACGCGATTTATCCCCAAAGATGGCGTGAAGTAAACGTTCTTCAGCAGAAAG

GTCTTTTTCACCTTTAGGTGTGACTTTACCTACTAAGATGTCGCCTTCTTTAAC

CTCAGCACCGATACGGATAATGCCCATTTCGTCAAGGTCTTTGAGGGCTTCTT

CACCAACATTTGGGATTTCCGAGTGATTCTTCAGGGCA-3'
```

SEQ ID no 12: partial sequence of the rpoB gene in *Streptococcus pneumoniae* CIP 102911[T] measuring 724 base pairs:

```
5'-CAACCATGTGGTGGAGTTTGATCATGTACATGACTCCGACAGAAAACACG

GTTATCAAACGGTTCACCAGTACGTCCATCGTAAAGGATCGTTTTGGCATCGC

TATCCATACCTGCTTCTTTAACAGTTGACCAAAGATCTTCAGAACTTGCTCCAT

CAAAGACTGGTGTCGCGATGTGAATACCAAGAGTACGAGCTGCCATACCAAG

GTGAAGCTCCATAACCTGACGGATATTCATACGTGATGGTACCCCAAGTGGGT

TCAACATGATGTCGAGTGGAGTTCCGTCTGGAAGGTAAGGCATGTCTTCTACA
```

```
GGAACGATACGAGAGACAACCCCTTTGTTTCCGTGACGTCCGGCCATTTTATC

TCCGACCTTAATCTTACGTTTTTGAGCGATGTAAACACGAACCAACATGTTAAC

ACCTGATTGCAACTCATCTCCATTTACACGTGTAAAGATCTTAACATCACGAAC

GACACCATCGGCACCGTGTGGTACACGAAGAGAAGTATCACGCACTTCACGA

GACTTGTCTCCAAAGATAGCGTGCAAGAGACGTTCTTCAGCTGAAAGATCTTT

CTCACCCTTAGGTGTTACTTTACCTACAAGAATATCACCTTCTTTAACCTCAGCA

CCAATACGGATAATCCCATTTCGTCAAGGTCTTTGAGGGCATCTTCACCAACG

TTTTGGAATTTCGCGAGTGATTTCTTCAGGTCCAA-3'
```

SEQ ID no 13: partial sequence of the rpoB gene in *Streptococcus oralis* CIP 102922$^T$ measuring 694 base pairs:

```
5'-ACTCGTGAAATTCCAAACGTTGGTGAAGATGCCCTTAAAGACCTTGACGAAAT

GGGTATTATCCGTATTGGTGCTGAGGTTAAAGAAGGAGATATCCTTGTAGGT

AAAGTCAGACCTAAGGGTGAAAAAGACCTTTCTGCTGAAGAACGTCTCTTGCA

CGCTATCTTCGGAGACAAGTCTCGTGAAGTGCGTGATACTTCTCTTCGAGTAC

CTCACGGTGCCGATGGTGTCGTTCGTGATGTTAAGATCTTTACACGTGCAAAT

GGTGATGAGTTGCAATCTGGTGTGAATATGCTGGTTCGTGTCTACATCGCTCA

AAAACGTAAGATCAAGTCGGAGATAAGATGGCCGGACGTCACGGAAACAAAG

GGGTTGTCTCTCGTATCGTTCCTGTAGAAGACATGCCTTACCTTCCAGATGGA

ACTCCAGTCGATATCATGTTGAACCCACTTGGGGTGCCATCACGTATGAATAT

CGGTCAGGTTATGGAACTCCACCTTGGTATGGCAGCCCGTACTCTTGGTATCC

ACATCGCAACACCAGTCTTTGACGGAGCAAGTTCGGAAGACCTTTGGGACACT

GTTAAAGAAGCAGGTATGGATAGCGATGGCAAAACAATCCTTTACGATGGAC

GTACAGGTGAGCCGTTTGACAACCGTGTATCAGTTGGTGTCATGTACATGATC

AAACTCCA-3'
```

SEQ ID no 14: partial sequence of the rpoB gene in *Streptococcus mutans* CIP 103220$^T$ measuring 728 base pairs:

```
5'-TGTCATCAACCATGTGGTGAAGTTTAATCATATACATAACACCAACTGATA

CACGATTATCAAACGGCTCCCCTGTGCGACCATCATAAAGAACAGTTTTAGCA

TCAGAATCCATACCGGCTTCTTTTACTGTTTCCCAAAGATCATCAGAAGTTGCT

CCGTCAAAGACAGGCGTTGCAATATGAATGCCCAAATTACGAGCAGCCATACC

AAGATGGAGTTCCATAACTTGCCCAATGTTCATCCGTGATGGCACCCCAAGTG

GATAAGCATGATATCAACAGGTGTTCCATCTGGAAGATATGGCATATCTTCC

ACTGGTACAATACGGGAAACGACACCCTTGTTACCATGACGTCCGGGCATCTT

ATCTCCGACCTTGATTTTACGTTTTTGAGCGATATAAACACGAACCAGCATGTT

AACACCTGATTGAAGTTCATCTCCATTAGCACGTGTAAAGATTTTCACATCACA

AACAACACCGTCGCCACCATGAGGTACACGAAGAGAAGTATCACGAACTTCAC

GTGATTTGTCACCAAAAATGGCATGCAAGAGGCGTTCTTCTGCAGAAAGATCT
```

-continued

```
TTTTCTCCTTTAGGAGTCACTTTACCAACTAGAATATCACCTTCTTTAACCTCAG

CACAATGCGAATAATTCCCATTTCATCAAGGTCTTTCAGGGCATCTTCACCAA

CATTTGGGATTTCACGCGTAATTTCTTCAGGTCCA-3'
```

SEQ ID no 15: partial sequence of the rpoB gene in *Streptococcus mitis* CIP 103335$^T$ measuring 730 base pairs:

```
5'-TGTCATCAACCATGTGGTGGAGTTTGATCATGTAACATGACTCCGACAGA

AAACACGGTTATCAAATGGTTCACCTGTACGTCCATCGTAAAGGATTGTTTTG

GCATCGCTATCCATACCAGCTTCTTTAACAGTTGACCAAAGATCTTCAGAACTT

GCTCCGTCAAAGACTGGTGTTGCGATGTGAATACCAAGAGTACGAGCTGCCA

TCCCAAGGTGGAGTTCCATAACCTGACCGATATTGATACGTGATGGCACCCCA

AGTGGGTTCAACATGATATCGACTGGAGTTCCATCTGGAAGGTAAGGCATAT

CTTCTACAGGAACGATACGAGAGACAACCCCTTTATTCCGTGACGTCCGGCC

ATCTTATCTCCGACCTTGATCTTACGTTTTTGAGCGATGTAGAGGCGAACCAG

CATGTTGACACCTGATTGCAATCATGTCCATTTGCACGTGTAAAGATCTTAAC

ATCACGAAGCACACCATCAGCTCCGTGTGGTACACGAAGAGAAGTGTCACGTA

CTTCACGAGATTTATCTCCGAAGATAGCGTGCAAGAGCCGTTCTTCAGCTGAA

AGGTCTTTCTCACCCTTAGGTGTTACTTTACCTACAAGGATATCCCCTTCTTTA

ACCTCAGCACCGATACGGATAATACCCATTTCGTCAAGATCTTTAAGGGCATC

TTCCCCAACGTTTGGGATTTCACGAGTAATTTCTTCAGGTCCA-3'
```

SEQ ID no 16: partial sequence of the rpoB gene in *Streptococcus equinus* CIP 102504$^T$ measuring 697 base pairs:

```
5'-CACTCGCGAAATTCCAAACGTTGGTGAAGAAGCTCTTAAAGACCTTGACGAAA

TGGGTATTATCCGTATCGGTGGTGAAGTTAAAGAAGGTGACATCCTTGTAGG

TAAAGTAACACCTAAAGGTGAAAAAGACCTTTCTGCTGAAGAGCGCCTTCTTC

ACGCAATCTTCGGTGATAAATCACGTGAAGTTCGTGATACATCACTTCGTGTA

CCACACGGTGGAGATGGTGTCGTTCGTGACGTTAAAATCTTTACACGTGCAAA

CGGTGATGAATACAATCAGGTGTTAACATGCTCGTTCGTGTTTATATCGCAC

AAAAACGTAAAATCAAAGTCGGAGATAAAATGGCCGGTCGTCACGGTAACAA

AGGGGTTGTTTCTCGTGTTGTTCCAGTTGAAGACATGCCTTATCTTCCAGACG

GAACTCCAGTCGATATCATGTTGAACCCACTTGGGGTGGCATCTCGTATGAAC

ATCGGACAAGTTATGGAGCTTCACCTTGGTATGGCTGCTCGTAACCTTGGTAT

TCACATTGCAACACCAGTCTTTGATGGGCAACTTCTGAAGACCTTTGGGATA

CAGTTAACGAAGCTGGTATGGCTAGCGACGCTAAGACAGTTCTTTACGATGG

ACGTACTGGTGAACCATTTGATAACCGTGTGTCAGTTGGTGTCATGTACATGA

TTAAACTTCAC-3'
```

SEQ ID no 17: partial sequence of the rpoB gene in *Streptococcus constellatus* CIP 103247$^T$ measuring 731 base pairs:

```
5'-AGTTGTCATCAACCATGTGTGCAATTTAATCATATACATGACACCGACAGA
TAGACGGTTGTCAAACGGCTCGCCCGTACGACCATCATAAAGAATCGTCTTGG
CATCGCTATCCATGCCTGCTTCACGAACAGTATCCCAAAGGTCATCTGAGCTT
GCTCCGTCAAATACTGGCGTTGCTATGTGGATACCAAGGTTGCGAGCAGCCA
TACCAAGGTGAAGCTCCATAACCTGTCCGATATTCATACGTGATGGCACCCCA
AGTGGGTTCAACATGATGTCTACTGGTGTTCCGTCTGGAAGATAAGGCATAT
CCTCAACTGGAACGATACGGGAAACAACCCCTTTATTTCCGTGGCGTCCGGCC
ATCTTATCCCCAACGCGGATCTTTCGTTTTTGAGCAATGTAAACACGCAGCAAC
ATGTTGACACCAGATTGCAATTCATCACCGTTCGCACGAGTAAAGATTTTCAC
ATCACGGACAACCCCAGCACCACCATGTGGTACACGAAGAGATGTGTCACGTA
CTTCACGAGATTTATCACCGAAAATTGCATGAAGCAGGCGTTCTTCAGCGGAT
AAGTCTTTTTCACCTTTCGGCGTTACTTTACCGACAAGAATGTCGCCCTCTTTC
ACCTCAGCACCAATGCGGATAATTCCCATTTCGTCAAGGTCTCTTAGCGCATCT
TCCCCAACGTTTGGAATTTCGCGCGTAATTTCTTCAGGTCCAA-3'
```

SEQ ID no 18: partial sequence of the rpoB gene in *Streptococcus anginosus* CIP 102921$^T$ measuring 697 base pairs:

```
5'-CACGCGCGAAATTCCAAACGTCGGTGAAGATGCTTTGAGAGACCTTGACGAA
ACGGGAATTATCCGCATTGGTGCTGAGGTAAAAGAAGGCGACATTCTTGTCG
GTAAAGTAACACCGAAAGGTGAAAAGACTTATCTGCTGAAGAACGCCTGCT
TCATGCAATTTTCGGTGATAAATCTCGTGAAGTACGTGATACTTCCCTTCGTGT
ACCACATGGTGGTGCAGGGGTTGTCCGTGATGTGAAAATCTTTACTCGTGCG
AACGGTGATGAATTGCAATCTGGTGTCAACATGTTGGTACGTGTTTACATCGC
TCAAAAACGGAAAATCCGTGTTGGGGATAAGATGGCTGGACGTCACGGAAAC
AAAGGGGTTGTTTCCCGCATTGTTCCAGTTGAGGATATGCCGTATCTTCCAGA
TGGAACACCAGTTGATATTATGTTGAACCCACTTGGGGTGCCATCTCGTATGA
ATATTGGTCAAGTTATGGAGCTTCACCTCGGTATGGCTGCTCGCAACCTTGGC
ATTCACATTGCAACACCAGTATTTGACGGGGCTAGCTCAGATGATGTTTGGGA
AACCGTTCGTGAAGCTGGCATGGATAGCGATGCTAAGACAATCCTTTATGAT
GGCCGTACTGGTGAGCCATTTGATAATCGTGTATCCGTTGGTGTCATGTACAT
GATCAAACTCCAC-3'
```

SEQ ID no 19: partial sequence of the rpoB gene in *Streptococcus dysgalactiae* CIP 102914$^T$ measuring 728 base pairs:

```
5'-TGTCATCAACCATGTGGTGGAGTTTAATCATGTACATGACACCAACGGAT
ACACGGTTGTCAAATGGTTCGCCAGTACGTCCATCATAAAGGACCGTCTTAGC
ATCGCTATCCATACCAGCTTCACGAACAGTGTCCCAAAGGTCTTCTGATGAAG
CCCCGTCAAAGACAGGTGTTGCAATGTGAATACGAAGATTACGAGCAGCCATA
CCAAGGTGAAGTTCCATAACCTGACCAATGTTCATCCGTGATGGCACCCCAAG
AGGGTTCAACATGATGTCAACTGGTGTTCCATCTGGAAGGTATGGCATGTCTT
```

-continued

```
CAACTGGTACAATACGTGAAACGACACCCTTGTTTCCGTGACGACCAGCCATT

TTATCTCCGACTTTGATCTTACGTTTTTGAGCAATGTAAACACGCACAAGCATA

TTAACACCTGATTGCAATTCATCGCCGTTAGCGCGTGTAAAGATTTTCACATCA

CGAACGATACCATCACCACCGTGAGGTACACGAAGGGACGTATCACGAACTTC

ACGTGATTTATCTCCAAAGATGGCATGCAAGAGACGCTCTTCAGCAGAAAGGT

CTTTTTCACCTTTAGGTGTGACTTTACCTACTAAGATGTCGCCTTCTTTAACCTC

AGCAACCGATACGGATAATTCCCATTTCGTCAAGGTCTTTGAGCGCTTCTTCACC

AACGTTTGGAATTTCGCGGGTGATTTCTTCAGGTCAA-3'
```

SEQ ID no 20: partial sequence of the rpoB gene in *Streptococcus bovis* CIP 102302[T] measuring 728 base pairs:

```
5'-TGTCATCAACCATGTGGTGAAGTTTGATCATGTACATGATACCAACAGAG

ACACGATTATCAAATGGTTCACCTGTACGACCGTCATAAAGAACTGTCTTAGC

GTCGCTATCCATACCAGCTTCACGAACAGTATCCCAAAGGTCTTCTGAAGTTG

CCCCGTCAAAGACTGGAGTTGCAATGTGAATACCGAGGTTACGAGCTGCCAT

ACCAAGGTGAAGTTCCATAACTTGTCGGATATTCATACGAGATGGCACCCCAA

GAGGGTTCAACATGATATCAACTGGAGTTCCGTCTGGAAGATATGGCATGTC

TTCAACAGGAACGATACGAGAAACAACCCCTTTGTTTCCGTGACGACCGGCCA

TTTTATCTCCGACTTTGATTTTACGTTTTTGTGCAATGTAAACACGAACGAGCA

TGTTGACACCTGATTGCAATTCATCACCGTTAGCACGTGTGAAGATTTTAACA

TCACGAACAACACCGTCTCCACCGTGTGGCACACGAAGTGATGTATCACGTAC

TTCACGAGATTTATCACCGAAGATTGCGTGAAGAAGGCGTTCTTCAGCAGAAA

GGTCTTTTTCACCTTTAGGTGTTACTTTACCTACAAGGATATCACCTTCTTTAA

CTTCAGCACCGATACGGATAATACCCATTTCGTCAAGGTCTTTAAGAGCTTCTT

CACCAACGTTTGGAATTTCGCGAGTGATTTCTTCAGGTCAA-3'
```

SEQ ID no 21: partial sequence of the rpoB gene in *Streptococcus acidominimus* CIP 82.4[T] measuring 728 base pairs:

```
5'-TTGTCATCAACCATGTGGTGGAGCTTAATCATGTACATGACACCAACAG

ACACACGGTTATCAAATGGTTCACCAGTACGACCATCATAAAGAATCGTTTTA

GCATCGCTGTCCATTCCTGCCTCTTTAACAGTTGACCAGAGATCCTCTGAGCTC

GCACCATCGAAAACCGGTGTTGCGATATGGATACCCAAGTTACGAGCAGCCAT

ACCCAAGTGCAGTTCCATAACCTGACCAATATTCATACGAGATGGCACCCCAA

GTGGGTTCAACATGATGTCAACTGGTGTTCCATCTGGAAGATATGGCATGTCT

TCAACTGGTACAATACGAGAAACGACACCCTTGTTACCGTGACGACCGGCCAT

CTTATCTCCGACCTTAATCTTGCGTTTTTGAGCGATATACACACGTACCAGCAT

ATTAACACCAGACTGTAGCTCATCACCATTAGCACGCGTAAAGATTTTCACATC

ACGAACAACACCATCTGCACCGTGTGGCACACGTAGAGAGGTATCACGTACTT

CACGTGATTTGTCACCGAAGATAGCATGCAAGAGACGCTCCTCAGCAGAAAG
```

```
                         -continued
ATCTTTTTCACCTTTTGGTGCACCTTACCAACAAGAATATCGCCTTCTTTAACT

TCTGCACCGATACGGATAATACCCATTTCGTCAAGGTCTTTGAGGGCTTCTTC

ACCAACGTTTGGAATTTCACGAGTAATTTCTTCAGGTCA-3'
```

SEQ ID no 22: partial sequence of the rpoB gene in *Streptococcus agalactiae* CIP 103227[T] measuring 733 base pairs:

```
5'-TGAGTTGTCATCAACCATGTGGTGAAGTTTGATCATGTACATGACACCAA

CTGACACACGGTTATCGAATGGTTCACCAGTACGACCATCATAAAGAACAGTC

TTAGCATCTGAATCCATACCTGCTTCTTGAACAGTTTCCCAAAGGTCTTCTGAA

GAAGCCCCATCAAAGACTGGCGTTGCAATATGAATACCTAAATTACGAGCAGC

CATACCTAAATGAAGCTCCATAACTTGTCCGATATTCATACGTGATGGCACCCC

AAGTGGGTTCAACATGATATCAACTGGCGTTCCATCTGGTAAGTAAGGCATAT

CTTCAACAGGAACAATACGTGAGACGACACCTTTGTTTCCGTGACGACCGGCC

ATCTTATCACCGACTTTGATTTTACGTTTTTGAGCGATATAAACGCGGACAAG

CATATTAACACGTGATTGCAATTCATCACCATTTGCACGAGTAAAGATTTTAAC

GTCACGAACTACTCCATCGCCACCGTGAGGTACACGTAGTGAAGTATCACGAA

CTTCACGTGATTTATCACCAAAAATGGCATGCAAGAGACGTTCTTCAGCAGAT

AAGTCCTTTTCACCCTTAGGTGTTACCTTACCAACAAGAATGTCACCTTCTTTT

ACCTCAGCACCAATGCGGATAATTCCCATTTGATCGAGATCACGTAGTGAATC

TTCACCAACATTTTGGATTTCACGAGTAATTTCTTCAGGTCCA-3'
```

SEQ ID no 23: partial sequence of the rpoB gene in *Streptococcus difficilis* CIP 103768[T] measuring 714 base pairs:

```
5'-TTGTCATCAACCATGTGGTGAAGTTTGATCATGTACATGACACCAACTGAC

ACACGGTCATCGAATGGTTCACCAGTATGACCATCATAAAGAACAGTCTTAGCAT

CTGAATCCATACCTGCTTCTTGAACAGTTTCCCAAAGGTCTTCTGAAGAAGCCCC

ATCAAAGACTGGCGTTGCAATATGAATACCTAAATTACGAGCAGCCATACCTAAA

TGAAGCTCCATAACTTGTCCGATATTCATACGTGATGGCACCCCAAGTGGGTTCA

ACATGATATCAACTGGCGTTCCATCTGGTAAATAAGGCATATCTTCAACAGGAAC

AATACGTGAGACGACACCTTTGTTTCCGTGACGACCGGCCATGTTATCACCGACT

TTGATTTTACGTTTTTGAGCGATATAAACGCGGACAAGCATATTAACACCTGATT

GCAATTCATCACCATTTGCACGAGTAAAGATTTTAACGTCACGAACTACTCCATC

GCCACCGTGAGGTACACGTAGTGAAGTATCACGAACTTCACGTGATTTATCACCA

AAAATGGCATGCAAGAGACGTTCTTCAGCAGATAAGTCCTTTTCACCCTTAGGCG

TTACCTTACCAACAAGAATGTCACCTTCTTTTACCTCAGCACCAATGCGGATAATT

CCCATTTCATCGAGATCACGTAGTGAATCTTCACCAACATTTGGAATTTCACGAG

TA-3'
```

SEQ ID no 24: partial sequence of the rpoB gene in *Streptococcus intermedius* CIP 103248[T] measuring 728 base pairs:

```
5'-TGTCATCAACCATGTGGTGAAGCTTAATCATGTACATGACACCAACGGAC
ACACGGTTATCAAACGGTTCGCCAGTAGGTCCATCATAAAGGATTGTCTTAGC
ATCGCTATCCATACCTGCTTCACGAACGGTTCCCAAAGATCATCTGAGCTAGC
TCCGTCAAAGACTGGCGTTGCAATGTGGATACCAAGTTGCGAGCAGCCATAC
CGAGGTGCAATTCCATAACTTGTCCGATATTCATACGTGACGGCACCCCAAGA
GGATTCAACATGATATCAACTGGTGTCCCGTCTGGAAGATACGGCATATCCTC
AACTGGAACAATGCGGGAAACAACCCCTTTGTTTCCGTGGCGTCCGGCCATCT
TATCTCCAACGCGGATTTTCCGTTTTTGAGCGATATAAACACGTACCAACATGT
TGACACCGGATTGCAATTCATCACCGTTCGCACGAGTAAAGATTTTTACATCAC
GGACAACACCTGCACCACCGTGTGGTACACGAAGGGAGGTATCACGCACTTC
ACGAGACTTATCACCAAAAATTGCATGAAGCAGGCGTTCTTCAGCGGATAAAT
CTTTTTCACCTTTCGGCGTTACTTTACCGACAAGAATGTCGCCTTCTTTTACCTC
AGCACCAATGCGGATAATTCCCATCTCGTCAAGGTCTCTCAAAGCATCTTCCCC
GACGTTTGGAATTTCGCGCGTGATTTCTTGAGGTCCA-3'
```

SEQ ID no 25: partial sequence of the rpoB gene in *Streptococcus equi* CIP 102910ᵀ measuring 728 base pairs:

```
5'-TGTCATCAACCATGTGGTGAAGCTTAATCATATACATGACACCAACTGAC
ACACGATTATCAAACGGCTCACCAGTACGGCCATCATAAAGAACAGTCTTAGC
ATCGCTATCCATACCTGCTTCACGAACAGTTTCCCAAAGGTCCTCAGACGTAGC
TCCGTCAAAGACCGGTGTTGCGATATGGATACCCAAATTACGAGCAGCCATAC
CTAGGTGAAGCTCCATAACCTGTCCAATGTTCATACGAGACGGCACCCCAAGA
GGGTTCAGCATGATGTCAACAGGGGTTCCGTCTGGCAGATATGGCATATCCT
CAACCGGTACAATACGTGAGACGACACCCTTGTTACCATGACGCCCGGCCATT
TTATCTCCGACCTTGATTTTACGCTTTTGAGCAATGTAAACACGCACCAGCATA
TTAACACCTGATTGAAGCTCATCACCATTTGCGCGTGTAAAGATCTTCACATCA
CGTACAATCCCGTCACCACCATGAGGAACACGTAACGAGGTATCACGAACCTC
ACGTGATTTATCACCAAAGATAGCATGCAGGAGACGTTCTTCAGCAGAAAGG
TCTTTTTTCACCGTTAGGAGTTACCTTACCAACAAGAATATCGCCTTCCTTGACC
TCTGCACCGATACGGATAATACCCATTTCATCAAGGTCCTTCGAGGGCTTCTTCA
CCAACGTTTGGCACTTCACGTGTGATTTCTTCAGGTCCA-3'
```

SEQ ID no 26: partial sequence of the rpoB gene in *Enterococcus gallinarum* CIP 103013ᵀ measuring 694 base pairs:

```
5'-CACTCGTGAAATCCCGAATGTCGGGAAGACGCATTGAAAGATCTAGACGAA
ATGGGTATCATCCGCATTGGTGCGGAAGTCAAAGATGGCGATCTGTTGGTTG
GTAAAGTAACGCCTAAAGGGGTAACGGAACTATCTGCAGAAGAACGCTTGCT
TCATGCAATCTTTGGTGAAAAAGCCCGCGAAGTCCGCGATACTTCTCTGCGCG
TACCTCACGGTGGTGGCGGAATCGTCGATGATGTGAAAATCTTTACCCGCGAA
GCTGGCGATGAATTGTCACCAGGTGTCAATATGCTCGTTCGCGTGTATATCGT
```

-continued

```
TCAAAAACGGAAAATCCATGAAGGGGATAAAATGGCCGGCCGTCACGGAAAT

AAAGGGGTCGTTTCTCGCATTATGCGAGAAGAAGACATGCCTTTCTTACCAGA

CGGTACACCAGTTGATATCATGTTGAACCCATTAGGGGTGCCTTCACGGATGA

ACATTGGACAAGTATTGGAATTACACTTAGGAATGGCTGCCCGCCAATTAGGA

ATCCACGTGGCTACACCAGTCTTTGATGGTGCCAGCGATGAAGATGTCTGGG

CAACAGTTGGAGAAGCCGGCATGGCTAGCGACGCCAAAACCGTTTTGTATGA

TGGCCGTACTGGAGAACCATTTGATGGTCGAATCTCCGTAGGTGTCATGTATA

TGATCAAATTGGCC-3'
```

SEQ ID no 27: partial sequence of the rpoB gene in *Enterococcus casseliflavus* CIP 103018$^T$ measuring 727 base pairs:

```
5'-TGTCATCAACCATGTGGGCCAATTTGATCATGTACATGACACCAACGGAG

ATGCGGCCATCAAATGGTTCGCCGGTACGTCCGTCGTAAAGCACTGTTTTGGC

ATCGCTGGCCATTCCTGCTTCAGCAACCGTTGCCCAAACATCTTCATCGCTGGC

TCCATCAAAGACTGGTGTTGCCACGTGAATGCCTAATTGACGCGCAGCCATTC

CTAAGTGTAACTCTAATACTTGTCCAATGTTCATCCGAGAAGGTACCCCTAATG

GGTTCAGCATGATATCGACTGGTGTGCCATCTGGTAAGAAAGGCATGTCTTCT

TCTGGCATAATGCGAGAAACGACCCCTTTGTTTCCGTGACGTCCGGCCATTTT

ATCCCCTTCATGGATTTTCCGTTTTTGAACGATATAAACGCGAACCAGCATGTT

CACACCTGGTGACAATTCATCGCCAGCTTCGCGGGTAAAGATTTTGACATCGT

GGACGATTCCGCCGCCGCCGTGAGGCACGCGTAGAGAAGTGTCACGCACTTC

GCGGGCTTTTTCACCAAAGATTGCGTGCAACAAACGCTCTTCTGCTGAAAGTT

CCGTTACCCCTTTTGGCGTGACTTTCCCACAAGCAGATCGCCATCTTTGACTT

CCGCACCAATGCGGATAATGCCCATTTCGTCTAGGTCTTTCAACGCGTCTTCCC

AACGTTCGGGATTTCGCGAGTGATTTCTTCAGGTCCA-3'
```

SEQ ID no 28: partial sequence of the rpoB gene in *Enterococcus saccharolyticus* CIP 103246$^T$ measuring 721 base pairs:

```
5'-TGTCATCAACCATGTGGGCAAGTTTAATCATGTACATTACCCCAACAGAG

ATACGACCATCGAATGGTTCACCCGTACGTCCGTCATAAAGAACAGTTTTCGC

ATCGCGCGCCATGCCCGCTTCCGCGAACTGTTTCCCATACGTCATCATCTGATGC

ACCATCAAATACTGGTGTAGCTACATGGATGCCTAACTGACGTGCAGCCATCC

CTAAGTGTAATTCCAATACTTCGTCCGATGTTCATACGAGATGGTACTCCTAGT

GGGTTCAACATGATATCAACTGGTGTGCCGTCTGGTAAGAATGGCATGTCTTC

TTCTGGCATAATGCGAGAGACAACCCCTTTGTTACCATGACGTCCCGCCATTTT

ATCTCCTTCGTGAATCTTACGTTTTGCACGATATAAACACGAACTAAGATGTT

CACACCTGGAGATAATTCGTCGCCTGCTTCACGGGTAAAGATTTTAACATCGT

GAACGATACCGCCACCGCCGTGAGGAACACGTAATGATGTATCACGTACTTCA
```

-continued
CGTGCTTTTTGACCGAAGATTGCGTGCAATAGACGTTCTTCTGCAGATAATTC

GGTTACCCCTTTAGGAGTGACTTTACCTACTAATAAGTCGCCATCTTGTACTTC

GGCACCGATACGGATAATACCCATTTCGTCTAAGTCTTTTAATGCGTCTTCCCC

AACGTTAGGAATTTCGCGTGTATTCTTCAG-3'

SEQ ID no 29: partial sequence of the rpoB gene in *Enterococcus faecium* CIP 103014$^T$ measuring 727 base pairs:

5'-TGTCATCAACCATGTGAGCAAGTTTGATCATGTACATCACACCGACAGAC

ACACGTCCATCAAATGGTTCACCTGTACGTCCGTCGTACAGAACAGTTTTCGC

ATCGCTGGCCATACCGGCTCACGACTGTTTCCCATACGTCTTCATCACTTGC

ACCATCAAATACTGGCGTTGCTACGTGGATACCTAACTGACGTGCAGCCATAC

CCAAGTGTAATTCCAATACTTGCCCGATGTTCATACGTGAAGGCACCCCTAAA

GGATTCAGCATGATATCGATTGGTGTTCCATCAGGTAGGAATGGCATATCTTC

TTCCGGCATAATACGGGATACAACCCCTTTATTTCCGTGACGACCGGCCATTTT

ATCCCCTTCATGGATTTTACGTTTTTGAACGATATAAACACGAACTAACATGTT

TACGCCTGGTGACAATTCATCTCCAGCTTGACGAGTAAAGATTTTCACATCGT

GAACGATACCGCCGCCGCCATGTGGTACACGTAATGATGTATCGCGGACTTCA

CGAGCTTTTTCGCCAAAGATCGCATGCAATAGACGTTCTTCTGCAGATAATTCT

GTTACCCCTTTTGGCGTGACTTTCCCTACAAGCAAATCGCCATCTTGGACTTCT

GCACCAATACGGATGATACCCATTTCGTCTAAATCTTTTAATGCGTCTTCCCGA

CATTAGGGATTTCGCGTGTGATTTCTTCAGGTCCA-3'

SEQ ID no 30: partial sequence of the rpoB gene in *Enterococcus faecalis* CIP 103015$^T$ measuring 724 base pairs:

5'-TGTCATCAACCATGTGGGCTAATTTAATCATATACATGACACCAACGGAA

ATACGGTTATCAAATGGTTCACCTGTACGTCCATCGTAAAGAACTGTTTTAGC

ATCGCTAGCCATACCAGCTTCACGAACAGTTTCCCAAACGTCTTCATCGGTTGC

CCCATCGAAAACAGGTGTTGCGACGTGAATACCTAATTGGCGAGCAGCCATAC

CTAAGTGTAATTCAAGTACTTGTCCGATATTCATACGAGAAGGTACCCCTAAT

GGGTTCAACATGATATCAACAGGTGTTCCGTCAGGTAAGAATGGCATATCTTC

TTCCGGCATAATACGGGAAACAACCCCTTTATTTCCGTGACGTCCCGCCATTTT

ATCTCCTTCGTGAATTTTACGTTTTTGAACGATATAGACACGAACTAACATGTT

GACAGCTGGTGATAATTCATCGCCAGCTTCACGAGTAAAGATTTCACATCAT

GAACGATACCGCCGCCACCGTGAGGTACACGGAGAGACGTATCACGAACTTC

GCGGGCTTTTTCCCCGAAGATTGCGTGTAATAAACGTTCTTCTGCAGATAATT

CTGTGACCCCTTTAGGTGTGACTTTCCCAAGTAGTAAGTCGCCATCTTGAACTT

CAGCACCAATGCGGATAATCCCCATTTCGTCTAAGTCTTTCAACGCGTCTTCCC

AACGTTTGGAATTTCACGGGTATTTCTTCAGGTCA-3'

SEQ ID no 31: partial sequence of the rpoB gene in *Enterococcus avium* CIP 103019$^T$ measuring 570 base pairs:

```
5'-GTCCATCATAAAGAACGGTCTTAGCATCTGCTGCCATACGAGCTTCACGA

ACTGTTTCCCAAACATCGCTATCTTGCGCACCATCGAAGACTGGTGTCGCAAC

ATGGATACCTAGTTGGCGAGCCGCCATTCCCAAGTGTAATTCCAACACTTGTC

CGATGTTCATCCGAGATGGCACACCTAATGGGTTCAACATGATATCAACTGGC

GTACCGTCTGGTAAGAAAGGCATGTCTTCTTCTGGCATAATGCGAGAAACGA

CCCCTTTATTTCCGTGACGGCCGGCCATTTTATCCCCTTCATGAATCTTACGTT

TTTGCACGATGTACACGCGCACTAACATATTTACACCTGGAGATAATTCATCGC

CTGCTTCACGAGTAAAGATCTTCACATCGTGAACGATCCCGCCGCCACCATGC

GGTACACGAAGAGATGTATCACGAACTTCACGAGCCTTTTCACCAAAGATCGC

ATGCAACAAACGTTCTTCAGCTGATAATTCTGTTACCCCTTTAGGAGTGACTTT

ACCAACTAATAAATCACCATCATGAACTTCAGCACCAATAC-3'
```
20

SEQ ID no 32: partial sequence of the rpoB gene in *Abiotrophia defectiva* CIP 103242$^T$ measuring 732 base pairs:

```
5'-GAAGTTGTCATCAACCATGTGGGCCAACTTAATCATGTACATAACCCCAA

GAGAGACTTTACGGTCAAATGGTTCACCGGTTCGACCATCATATAAGATAGTC

TTAGGGTCAGCTTCTAAGCCGGCTTCCTTAACTGTTTCCCAGACATCTTCTTCA

CTAGCACCGTCAAAGACAGGTGTTGCAATCTTGATGCCCATTTCGCGAGCAGC

CATCCCCAAGTGTAACTCTAGGACTTGCCCGATGTTCATACGGGATGGAACCC

CTAATGGGTTCAACATGATATCAACTGGGGTACCATCTGGTAAGAATGGCATA

TCTTCTTCCGGCATGATAAGGGAGACAACCCCTTTGTTACCGTGACGACCGGC

CATCTTATCCCCTTCATTGATTTTACGTTTTGTACGATGTAGACGCGGACTAG

CTTGTTGACACCTGGTGCCAATTCGTCGCCAGCTTCGCGGGTAAAGATTTTAA

CGTCGTGGACAATCCCGCCCCCGCCGTGTGGCACACGCAAGGAAGTATCACG

TACTTCACGCGCCTTCTCACCGAAGATAGCATGGAGCAAGCGTTCTTCCGCAG

ACAACTCGGTCACACCTTTTGGTGTTACCTTACCAACTAAGATATCGCCGTCTT

TTACTTCCGCCCCGATACAGATAATCCCGTCTTGGTCTAAGTACTTGAGGGCA

TCTTCGGACACGTTTGGAATTTCGCGTGTAATTTCTTCAGGTCA-3'
```

SEQ ID no 33: partial sequence of the rpoB gene in *Gemella morbilorum* CIP 81.10$^T$ measuring 727 base pairs:

```
5'-TGTCATCAACCATGTGTGCAAGTTTATCATGTACATTACCCCTACAGATAC

ACGGCTATCAAATGGCTCACCTGTACGTCCGTCATAAAGAACTGTCTTAGCAT

CTTTAGCCATTCCAGCTTCCGCAACTGTAGACCAAACATCTTCATCAGTAGCAC

CATCGAATACTGGTGTAGCTACGTGGATTCCAAGTTGTTTAGCAGCCATACCT

AAGTGTAGCTCTAATACTTGTCCAATGTTCATACGAGATGGAACCCCAAGTGG

GTTTAACATTACGTCAACTGGTGTACCATCTGGTAGGTAAGGCATATCTTCTT

CTGGTAAGATATTTGAGATAACCCCTTTGTTACCGTGACGACCGGCCATTTTA

TCTCCTACACGAATTTTACGTTTTTGGACGATAAATACACGAACAAGTTCATTT

ACACCGTTAGGTAATTCAGCACCATCTTCACGTTTAAAGATTTTAACATCAGCA
```

-continued

```
ACTACTCCATCAGCACCGTGAGGTACACGTAATGAAGTATCACGTACTTCTTTA

GATTTAGCTCCAAAGATAGCATATAATAATTTTTCTTCTGGAGTTTGTTCAGTT

AATCCTTTCGGTGTAACTTTACCTACTAAAATATCTCCATCTTTAACTTCAGCC

CCAATACGAATGATTCCTCGTGCATCTAAGTTTCTAAGTGCATTTTCACCCTAC

GTTTGGAATCTCACGAGTAATTTCTTCAGGTCA-3'
```

SEQ ID no 34: partial sequence of the rpoB gene in *Gemella haemolysans* CIP 101126$^T$ measuring 726 base pairs:

```
5'-TGTCATCAACCATGTGTGCAAGTTTAATCATGTACATTACCCCTACAGATA

CACGGCTATCAAATGGCTCACCTGTACGTCGGTCATAAAGAACTGTCTTAGCA

TCTTTAGCCATTCCAGCTTCCGCAACTGTAGACCAAACATCTTCATCAGTAGCA

CCATCGAATACTGGTGTAGCTACGTGGATTCCAAGTTGTTTAGCAGCCATACC

TAAGTGTAGCTCTAATACTTGTCCAATGTTCATACGAGATGGAACCCCAAGTG

GGTTTAACATTACGTCAACTGGTGTACCATCTGGTAGGTAAGGCATATCTTCT

TCTGGTAAGATATTTGAGATAACCCCTTTGTTACCGTGACGACCGGCCATTTT

ATCTCCTACACGAATTTTACGTTTTTGGACGATAAATACACGAACAAGTTCATT

TACACCGTTAGGTAATTCAGCACCATCTTCACGTTTAAAGATTTTAACATCAGC

AACTACTCCATCAGCACCGTGAGGTACACGTAATGAAGTATCACGTACTTCTTT

AGATTTAGCTCCAAAGATAGCATATAATAATTTTTCTTCTGGAGTTTGTTCAGT

TAATCCTTTCGGTGTAACTTTACCTACTAAAATATCTCCATCTTTAACTTCAGC

CCCAATACGAATGATTCCTCGTGCATCTAAGTTTCTAAGTGCATTTTCACCTAC

GTTTGGAATCTCACGAGTATTCTTCAGGTCCA-3'
```

SEQ ID no 35: partial sequence of the rpoB gene in *Granulicatella adjacens* CIP 103243$^T$ measuring 719 base pairs:

```
5'-CATCAACGATGTGAGCAAGTTTGATCATGTACATAACCCCTACTGACACA

CGGTTATCGAATGGTTCCCCTGTACGTCCATCATATAGAATTGTTTTCCGCATCA

CGAGCCATACCCGCTTCTGCAACAGTTCCCCATACGTCTTCATCTTGCGCACCA

TCGAATACTGGTGTTGCGATGTAAATACCTAATTCACGAGCAGCCATCCCTAA

GTGTAACTCTAACACTTGTCCGATGTTCATACGTGAAGGTACCCCTAATGGGT

TTAACATGATGTCAACTGGTGTTCCATCTGGTAAGAATGGCATATCTTCTTCC

GGCATAATACGGGAAACAACCCCTTTATTACCGTGACGTCCGGCCATCTTATC

CCCTTCATTGATTTTACGTTTTTGTACAATATATACACGAACTAATTTGTTTACG

CCAGGTGCTAATTCATCACCTGCTGCACGTGTGAATACACGTACATCACGGAC

AATACCGCCACCGCCGTGAGGTACACGTAGAGATGTGTCACGAACTTCACGA

GCTTTTTCACCGAAGATTGCGTGTAATAAACGTTCCTCTGGTGATTGTTCTGTT

AACCCTTTAGGAGTTACTTTACCAACTAAGATGTCACCATCTTTAACTTCGGCA

CCGATACGAATAATTCCGTCTGCGTCTAGGTTCTTCAATGCGTCTTCCCAACGT

TTGGAATCTCACGAGTAATTCTTCAGG-3'
```

In the above sequences, the M nucleotide designates A or C, the R nucleotide designates A or G, the W nucleotide designates A or T, the Y nucleotide designates C or T and the N nucleotide designates A, T, C or G.

In the above sequences, the CIP references relate to deposits with the national collection of microorganism cultures: Collection Nationale de Culture des Microorganismes (CNCM) at Institut Pasteur in Paris (France).

EXAMPLE 3

Blind Identification of a Collection of 20 Bacterial Strains Comprising 10 Strains of Bacteria Belonging to Genus *Streptococcus* and Related Genera A collection of twenty strains belonging to the following bacterial species: *Streptococcus pyogenes, Streptococcus sanguis, Granulicatella adjacens, Abiotrophia defectiva, Enterococcus avium, Enterococcus faecalis, Gemella haemolysans, Gemella morbilorum, Streptococcus equi, Streptococcus anginosus, Staphylococcus aureus, Pseudomonas oleovorans, Mycobacterium avium, Bacillus cereus, Acinetobacter anitratus, Corynebacterium amycolatum, Klebsiella terrigena, Pasteurella, Lactobacillus rhamnosus, Staphylococcus* was coded so as to conduct blind molecular identification of strains (the experimenter not having any a priori knowledge of strain identity) using the method described in the present patent application. Extraction of the nucleic acids and amplification of the rpoB gene fragment were performed as described in example 2 incorporating primers consisting of mixtures of 4 oligonucleotides which have sequences consisting of sequences SEQ ID no 6 (as 5' primer) and SEQ ID no 7 (as 3' primer) where N represents inosine, in a PCR amplification (FIG. 1). The sequencing of these 10 amplificates was conducted by incorporating into the sequencing reaction the primers SEQ ID no 6 and SEQ ID no 7 as described in example 2, and comparison of the sequences obtained with sequences SEQ ID no 1 to 5 and 8 to 35 enabled the 10 ten amplified strains to be identified as being *Streptococcus pyogenes, Streptococcus sanguis, Granulicatella adjacens, Abiotrophia defectiva, Enterococcus avium, Enterococcus faecalis, Gemella haemolysans, Gemella morbilorum, Streptococcus equi, Streptococcus anginosus*. The decoding of these 10 strains showed 100% agreement between molecular identification using the method that is the subject of the invention and the identification previously established by standard phenotype methods. This result illustrates the specificity of the set of primers SEQ ID no 6/SEQ ID no 7.

The other bacteria chosen because they are frequently isolated in human or animal clinical specimens and also possibly contain bacteria of genus *Streptococcus* were not amplified, thereby exhibiting the specificity of the primers used for the *Streptococcus* genus and said 4 related genera under the conditions of use of the invention for detecting bacteria of genus *Streptococcus* and said 4 related genera in comparison with bacteria of another genus.

FIG. 1 shows the PCR amplification products obtained from ten coded bacterial strains, comprising 7 strains belonging to genus *Streptococcus* and said 4 related genera (columns 2,3,4,7-11) and 3 bacterial strains of bacterial genera other than *Streptococcus* and said 4 related genera (columns 5, 6 and 12). Columns 1 and 13 show the molecular weight marker. The amplification products are obtained after incorporating primers SEQ ID no 6 and SEQ ID no 7 described above, and are visualized by staining with ethidium bromide after electrophoresis on agarose gel.

The invention claimed is:

1. An isolated rpoB gene or gene fragment of a bacterium of the genus *Streptococcus* or the related genus *Enterococcus*, comprising a nucleic acid sequence selected from the group consisting of:
   a. SEQ ID NOs: 8-10, 13, 15, 16, 20, 24, 29, and 30; and
   b. the full-length complementary sequences of the nucleic acid sequences of (a).

2. An isolated rpoB gene of claim 1 wherein the bacterium is of the bacteria *Streptococcus anginosus*, comprising a nucleic acid sequence selected from the group consisting of:
   a. SEQ ID NO:1 wherein:
      K nucleotide represents T or G,
      M nucleotide represents A or C,
      R nucleotide represents A or G,
      W nucleotide represents A or T,
      Y nucleotide represents C or T, and
      N nucleotide represents A, T, C, G or I; and
   b. the full-length complementary sequences of the nucleic acid sequences of (a).

3. A mixture of oligonucleotides, comprising:
   an equimolar mixture of oligonucleotides, wherein each oligonucleotide in the equimolar mixture of oligonucleotides has a different sequence and comprises at least 15 consecutive nucleotides of the full-length sequence set forth in SEQ ID NO:6 or SEQ ID NO:7, or at least 15 consecutive nucleotides of the full-length complementary sequences thereof, where:
      N represents, for the equimolar mixture, inosine or N represents, for the equimolar mixture, equimolar amounts of A, T, C, and G,
      R represents A or G,
      M represents A or C, and
      Y represents C or T.

4. A mixture of oligonucleotides according to claim 3, wherein the equimolar mixture of oligonucleotides comprises 32 different oligonucleotides, wherein each oligonucleotide in the equimolar mixture of oligonucleotides comprises at least 15 consecutive nucleotides of the sequence set forth in SEQ ID NO:6, or at least 15 consecutive nucleotides of the full-length complementary sequence thereof, where:
   R represents A or G,
   Y represents C or T,
   M represents A or C, and
   N represents A, T, C or G.

5. A mixture of oligonucleotides according to claim 3, wherein the equimolar mixture of oligonucleotides comprises 8 different oligonucleotides, wherein each oligonucleotide in the equimolar mixture of oligonucleotides comprises at least 15 consecutive nucleotides of the sequence set forth in SEQ ID NO:6, or at least 15 consecutive nucleotides of the full-length complementary sequence thereof, where:
R represents A or G,
Y represents C or T,
M represents A or C, and
N represents inosine.

6. A mixture of oligonucleotides according to claim 3, wherein the equimolar mixture of oligonucleotides comprises 16 different oligonucleotides, wherein each oligonucleotide in the equimolar mixture of oligonucleotides comprises at least 15 consecutive nucleotides of the sequence set forth in SEQ ID NO:7, or at least 15 consecutive nucleotides of the full-length complementary sequence thereof, where:
R represents A or G, and
N represents A, T, C or G.

7. A mixture of oligonucleotides according to claim 3, wherein the equimolar mixture of oligonucleotides comprises 4 different oligonucleotides, wherein each oligonucleotide in the equimolar mixture of oligonucleotides comprises at least 15 consecutive nucleotides of the sequence set forth in SEQ ID NO:7, or at least 15 consecutive nucleotides of the full-length complementary sequence thereof, where:
R represents A or G, and
N represents inosine.

8. A mixture of oligonucleotides according to claim 3, wherein each oligonucleotide in the equimolar mixture of oligonucleotides consists of the sequence set forth in SEQ ID NO:6, SEQ ID NO:7, or the full-length complementary sequences thereof.

9. A method for detecting the presence of a bacterium of genus *Streptococcus* or of 4 related genera *Enterococcus*, *Gemella*, *Abiotrophia* and *Granulicatella*, comprising:
 1. contacting at least one genus probe comprising a mixture of oligonucleotides as in claim 3, with a sample containing or possibly containing nucleic acids of at least one said bacterium, and
 2. determining the formation or non-formation of a hybridization complex between said genus probe and nucleic acids of the specimen, wherein the presence of said bacterium in the specimen is indicated by formation of a hybridization complex.

10. A method for detecting the presence of a bacterium of genus *Streptococcus* or of 4 related genera *Enterococcus*, *Gemella*, *Abiotrophia* and *Granulicatella*, comprising:
 1. contacting amplification primers comprising mixtures of oligonucleotides as in claim 7, with a sample containing or possibly containing nucleic acids of at least one said bacterium, wherein:
   a 5' primer comprises an equimolar mixture of oligonucleotides, wherein each oligonucleotide in the equimolar mixture of oligonucleotides has a different sequence and comprises at least 15 consecutive nucleotides of the sequence set forth in SEQ ID NO:6, or at least 15 consecutive nucleotides of the full-length complementary sequence thereof, and
   a 3' primer comprises an equimolar mixture of oligonucleotides, wherein each oligonucleotide in the equimolar mixture of oligonucleotides has a different sequence and comprises at least 15 consecutive nucleotides of the sequence set forth in SEQ ID NO:7, or at least 15 consecutive nucleotides of the full-length complementary sequence thereof; and
 2. amplifying nucleic acids by enzymatic polymerization reaction to determine the presence or absence of an amplification product, wherein occurrence of an amplification product indicates the presence of said bacterium in the sample.

11. A method for detecting whether a given species of a bacterium of genus *Streptococcus* or related genera is present in a sample, said given species of a bacterium selected from the group of species consisting of:
 *Streptococcus mutans, Streptococcus oralis, Streptococcus pneumoniae, Streptococcus pyogenes, Streptococcus salivarius, Streptococcus sanguinis, Streptococcus suis, Streptococcus acidominicus, Streptococcus agalactiae, Streptococcus anginosus, Streptococcus constellatus, Streptococcus difficilis, Streptococcus dysgalactiae, Streptococcus equi, Streptococcus equinus, Streptococcus intermedius, Streptococcus mitis, Streptococcus bovis, Streptococcus alactolyticus, Streptococcus gallolyticus, Streptococcus macedonicus, Streptococcus infantarius, Streptococcus hominis, Granulicatella adjacens, Abiotrophia defectiva, Enterococcus avium, Enterococcus casselliflavus, Enterococcus faecalis, Enterococcus faecium, Enterococcus gallinarum, Enterococcus sacharolyticus, Gemella haemolysans*, and *Gemella morbillorum*, the method comprising:
a) sequencing an amplified rpoB gene fragment of a bacterium using nucleotide primers comprising said oligonucleotide mixtures as in claim 3, wherein:
   a 5' primer comprises an equimolar mixture of oligonucleotides, wherein each oligonucleotide in the equimolar mixture of oligonucleotides has a different sequence and comprises at least 15 consecutive nucleotides of the sequence set forth in SEQ ID NO:6, or at least 15 consecutive nucleotides of the full-length complementary sequence thereof, and
   a 3' primer comprises an equimolar mixture of oligonucleotides, wherein each oligonucleotide in the equimolar mixture of oligonucleotides has a different sequence and comprises at least 15 consecutive nucleotides of the sequence set forth in SEQ ID NO:7, or at least 15 consecutive nucleotides of the full-length complementary sequence thereof; and
b) determining the presence or absence of the given species of said bacterium by comparing the sequence obtained of said fragment with the sequence of the complete rpoB gene of said bacterium or the sequence of a rpoB gene fragment of said bacterium respectively comprising said sequences selected from the group consisting of:
   i) SEQ ID NOs:8-35; and
   ii) the full-length complementary sequences of the nucleic acid sequences of (i);
wherein the presence of said bacterium in the sample is determined if the obtained sequence of said fragment is identical to the known sequence of the rpoB gene or gene fragment of said bacterium.

12. The method according to claim 10, further comprising:
 3. determining whether at least one species selected from the group consisting of *Streptococcus mutans, Streptococcus oralis, Streptococcus pneumoniae, Streptococcus pyogenes, Streptococcus salivarius, Streptococcus sanguinis, Streptococcus suis, Streptococcus acidominimus, Streptococcus agalactiae, Streptococcus anginosus, Streptococcus constellatus, Streptococcus difficilis, Streptococcus dysgalactiae, Streptococcus equi, Streptococcus equinus, Streptococcus intermedius, Streptococcus mitis, Streptococcus bovis, Streptococcus alactolyticus, Streptococcus gallolyticus, Streptococcus macedonicus, Streptococcus infantarius, Streptococcus hominis, Granulicatella adjacens, Abiotrophia defectiva, Enterococcus avium, Enterococcus casselliflavus, Enterococcus faecalis, Enterococcus faecium, Entero-*

*coccus gallinarum, Enterococcus sacharolyticus, Gemella haemolysans,* and *Gemella morbillorum,* is present in the sample by contacting the amplification product with at least one species probe comprising a nucleic acid sequence selected from the group consisting of:
  (a) the sequences set forth in SEQ ID NOs:8-35; and
  (b) the full-length complementary sequences of the nucleic acid sequences of (a); and
4. determining formation or non-formation of a hybridization complex between said species probe and the amplification product, wherein the formation of a hybridization complex indicates the presence of said at least one species in the sample.

13. A set of isolated rpoB gene or gene fragments comprising different rpoB gene or gene fragments respectively comprising:
  (a) the full-length sequences set forth in SEQ ID NOs:8-35; or
  (b) the full-length complementary sequences of the sequences of (a).

14. A set of isolated rpoB gene or gene fragments comprising different rpoB gene or gene fragments respectively comprising:
  (a) the full-length sequences set forth in SEQ ID NOs:8-35; and
  (b) the full-length complementary sequences of the sequences of (a).

* * * * *